United States Patent
Leach et al.

(10) Patent No.: US 8,425,417 B2
(45) Date of Patent: Apr. 23, 2013

(54) INTEGRATED DEVICE FOR CONTINUOUS IN VIVO ANALYTE DETECTION AND SIMULTANEOUS CONTROL OF AN INFUSION DEVICE

(75) Inventors: Jacob S. Leach, San Diego, CA (US); Peter C. Simpson, Encinitas, CA (US)

(73) Assignee: Dexcom, Inc., San Diego, CA (US)

( * ) Notice: Subject to any disclaimer, the term of this patent is extended or adjusted under 35 U.S.C. 154(b) by 1110 days.

(21) Appl. No.: 12/267,494

(22) Filed: Nov. 7, 2008

(65) Prior Publication Data

US 2009/0124964 A1     May 14, 2009

Related U.S. Application Data

(63) Continuation-in-part of application No. 12/055,114, filed on Mar. 25, 2008, now Pat. No. 8,364,231, and a continuation-in-part of application No. 12/055,078, filed on Mar. 25, 2008, and a continuation-in-part of application No. 12/055,149, filed on Mar. 25, 2008, now abandoned, and a continuation-in-part of application No. 12/055,203, filed on Mar. 25, 2008, and a continuation-in-part of application No. 12/055,227, filed on Mar. 25, 2008, now Pat. No. 8,364,230, which is a continuation-in-part of application No.

(Continued)

(51) Int. Cl.
*A61B 5/00* (2006.01)

(52) U.S. Cl.
USPC .................................... 600/365; 600/347

(58) Field of Classification Search ........... 600/347, 600/365
See application file for complete search history.

(56) References Cited

U.S. PATENT DOCUMENTS

| 3,506,032 A | 4/1970 | Eveleigh et al. |
| 3,556,950 A | 1/1971 | Dahms |

(Continued)

FOREIGN PATENT DOCUMENTS

| EP | 0 098 592 | 1/1984 |
| EP | 0 127 958 | 12/1984 |

(Continued)

OTHER PUBLICATIONS

Abel et al. 2002. Biosensors for in vivo glucose measurement: can we cross the experimental stage. Biosens Bioelectron 17:1059-1070.

(Continued)

*Primary Examiner* — Patricia Mallari
*Assistant Examiner* — Karen Toth

(57) ABSTRACT

Systems and methods of use for continuous analyte measurement of a host's vascular system and the simultaneous control of a flow control device are provided. In some embodiments, an integrated system includes a vascular access device, a continuous analyte sensor, system electronics and an electronic cable for communication with a third-party infusion device, the system being configured for insertion into fluid communication with a host's circulatory system.

24 Claims, 7 Drawing Sheets

Related U.S. Application Data

11/691,466, filed on Mar. 26, 2007, now Pat. No. 7,615,007, and a continuation-in-part of application No. 11/691,424, filed on Mar. 26, 2007, and a continuation-in-part of application No. 11/691,432, filed on Mar. 26, 2007, now Pat. No. 7,775,975, and a continuation-in-part of application No. 11/691,426, filed on Mar. 26, 2007, said application No. 12/055,203 is a continuation-in-part of application No. 11/691,466, and a continuation-in-part of application No. 11/691,424, and a continuation-in-part of application No. 11/691,432, and a continuation-in-part of application No. 11/691,426, said application No. 12/055,149 is a continuation-in-part of application No. 11/691,466, and a continuation-in-part of application No. 11/691,424, and a continuation-in-part of application No. 11/691,432, and a continuation-in-part of application No. 11/691,426, said application No. 12/055,114 is a continuation-in-part of application No. 11/691,466, and a continuation-in-part of application No. 11/691,424, and a continuation-in-part of application No. 11/691,432, and a continuation-in-part of application No. 11/691,426, said application No. 12/055,078 is a continuation-in-part of application No. 11/691,466, and a continuation-in-part of application No. 11/691,424, and a continuation-in-part of application No. 11/691,432, and a continuation-in-part of application No. 11/691,426, said application No. 12/055,078 is a continuation-in-part of application No. 11/543,683, filed on Oct. 4, 2006, now Pat. No. 7,366,556, which is a continuation-in-part of application No. 11/004,561, filed on Dec. 3, 2004, now Pat. No. 7,715,893, said application No. 12/055,078 is a continuation-in-part of application No. 11/865,572, filed on Oct. 1, 2007, which is a continuation-in-part of application No. 11/543,683, said application No. 11/691,466 is a continuation-in-part of application No. 11/543,396, filed on Oct. 4, 2006, and a continuation-in-part of application No. 11/543,490, filed on Oct. 4, 2006, and a continuation-in-part of application No. 11/543,404, filed on Oct. 4, 2006, said application No. 11/691,432 is a continuation-in-part of application No. 11/543,396, and a continuation-in-part of application No. 11/543,490, and a continuation-in-part of application No. 11/543,404, said application No. 11/691,426 is a continuation-in-part of application No. 11/543,396, and a continuation-in-part of application No. 11/543,490, and a continuation-in-part of application No. 11/543,404, said application No. 11/691,424 is a continuation-in-part of application No. 11/543,396, and a continuation-in-part of application No. 11/543,490, and a continuation-in-part of application No. 11/543,404.

(60) Provisional application No. 60/527,323, filed on Dec. 5, 2003, provisional application No. 60/587,787, filed on Jul. 13, 2004, provisional application No. 60/614,683, filed on Sep. 30, 2004.

(56) References Cited

U.S. PATENT DOCUMENTS

| | | |
|---|---|---|
| 3,610,226 A | 10/1971 | Albisser |
| 3,610,230 A | 10/1971 | Andersen |
| 3,837,339 A | 9/1974 | Aisenberg |
| 3,838,682 A | 10/1974 | Clark et al. |
| 3,874,850 A | 4/1975 | Sorensen et al. |
| 3,898,984 A | 8/1975 | Mandel et al. |
| 3,910,256 A | 10/1975 | Clark et al. |
| 3,933,593 A | 1/1976 | Sternberg |
| 3,943,918 A | 3/1976 | Lewis |
| 4,008,717 A | 2/1977 | Kowarski |
| 4,016,866 A | 4/1977 | Lawton |
| 4,030,640 A | 6/1977 | Citrin et al. |
| 4,055,175 A | 10/1977 | Clemens et al. |
| 4,109,505 A | 8/1978 | Clark et al. |
| 4,119,406 A | 10/1978 | Clemens |
| 4,151,845 A | 5/1979 | Clemens |
| 4,176,659 A | 12/1979 | Rolfe |
| 4,197,852 A | 4/1980 | Schindler et al. |
| 4,206,755 A | 6/1980 | Klein |
| 4,240,438 A | 12/1980 | Updike et al. |
| 4,253,469 A | 3/1981 | Aslan |
| 4,265,249 A | 5/1981 | Schindler et al. |
| 4,300,572 A | 11/1981 | Knighton |
| 4,366,040 A | 12/1982 | Marsoner et al. |
| 4,369,785 A | 1/1983 | Rehkopf et al. |
| 4,403,984 A | 9/1983 | Ash et al. |
| 4,407,298 A | 10/1983 | Lentz et al. |
| 4,432,366 A | 2/1984 | Margules |
| 4,448,188 A | 5/1984 | Loeb |
| 4,457,339 A | 7/1984 | Juan et al. |
| 4,478,222 A | 10/1984 | Koning et al. |
| 4,486,290 A | 12/1984 | Cahalan et al. |
| 4,492,575 A | 1/1985 | Mabille |
| 4,494,950 A | 1/1985 | Fischell |
| 4,496,454 A | 1/1985 | Berger |
| 4,519,973 A | 5/1985 | Cahalan et al. |
| 4,526,569 A | 7/1985 | Bernardi |
| 4,534,825 A | 8/1985 | Koning et al. |
| 4,535,786 A | 8/1985 | Kater |
| 4,554,927 A | 11/1985 | Fussell |
| 4,565,665 A | 1/1986 | Fogt |
| 4,565,666 A | 1/1986 | Cahalan et al. |
| 4,568,444 A | 2/1986 | Nakamura et al. |
| 4,571,292 A | 2/1986 | Liu et al. |
| 4,573,968 A | 3/1986 | Parker |
| 4,592,824 A | 6/1986 | Smith et al. |
| 4,600,495 A | 7/1986 | Fogt |
| 4,613,328 A * | 9/1986 | Boyd ............................ 604/156 |
| 4,614,514 A | 9/1986 | Carr et al. |
| 4,626,104 A | 12/1986 | Pointon et al. |
| 4,655,880 A | 4/1987 | Liu |
| 4,670,007 A | 6/1987 | Wheeldon et al. |
| 4,671,288 A | 6/1987 | Gough |
| 4,672,970 A | 6/1987 | Uchida et al. |
| 4,685,463 A | 8/1987 | Williams |
| 4,694,861 A | 9/1987 | Goodale et al. |
| 4,703,756 A | 11/1987 | Gough et al. |
| 4,705,503 A | 11/1987 | Dorman et al. |
| 4,731,726 A | 3/1988 | Allen |
| 4,736,748 A * | 4/1988 | Nakamura et al. ............ 600/352 |
| 4,747,822 A | 5/1988 | Peabody |
| 4,755,168 A | 7/1988 | Romanelli et al. |
| 4,757,022 A | 7/1988 | Shults et al. |
| 4,763,648 A | 8/1988 | Wyatt |
| 4,777,953 A | 10/1988 | Ash et al. |
| 4,784,157 A | 11/1988 | Halls et al. |
| 4,786,394 A | 11/1988 | Enzer et al. |
| 4,789,467 A | 12/1988 | Lindsay et al. |
| 4,791,932 A | 12/1988 | Margules |
| 4,800,495 A | 1/1989 | Smith |
| 4,805,625 A | 2/1989 | Wyler |
| 4,808,089 A | 2/1989 | Buchholtz et al. |
| 4,808,292 A | 2/1989 | Kessler et al. |
| 4,809,704 A | 3/1989 | Sogawa et al. |
| 4,810,243 A | 3/1989 | Howson |
| 4,813,423 A | 3/1989 | Miyasaka et al. |
| 4,815,471 A | 3/1989 | Stobie |
| 4,820,281 A | 4/1989 | Lawler |
| 4,822,336 A | 4/1989 | DiTraglia |
| 4,828,544 A | 5/1989 | Lane et al. |
| 4,830,013 A | 5/1989 | Maxwell |
| 4,832,005 A | 5/1989 | Takamiya et al. |
| 4,834,101 A | 5/1989 | Collison et al. |
| 4,838,281 A | 6/1989 | Rogers et al. |

| Patent No. | Date | Inventor(s) |
|---|---|---|
| 4,841,974 A | 6/1989 | Gumbrecht et al. |
| 4,852,573 A | 8/1989 | Kennedy |
| 4,854,322 A | 8/1989 | Ash et al. |
| 4,867,741 A | 9/1989 | Portnoy |
| 4,874,363 A | 10/1989 | Abell |
| 4,883,467 A | 11/1989 | Franetzki et al. |
| 4,889,528 A | 12/1989 | Nadai et al. |
| 4,900,305 A | 2/1990 | Smith et al. |
| 4,907,857 A | 3/1990 | Giuliani et al. |
| 4,909,786 A | 3/1990 | Gijselhart et al. |
| 4,919,649 A | 4/1990 | Timothy et al. |
| 4,921,477 A | 5/1990 | Davis |
| 4,921,480 A | 5/1990 | Sealfon |
| 4,923,819 A | 5/1990 | Fernandez et al. |
| 4,925,444 A | 5/1990 | Orkin et al. |
| 4,928,694 A | 5/1990 | Maxwell |
| 4,934,369 A | 6/1990 | Maxwell |
| 4,934,375 A | 6/1990 | Cole et al. |
| 4,946,439 A | 8/1990 | Eggers |
| 4,951,669 A | 8/1990 | Maxwell et al. |
| 4,953,552 A | 9/1990 | DeMarzo |
| 4,957,483 A | 9/1990 | Gonser et al. |
| 4,963,131 A | 10/1990 | Wortrich |
| 4,966,579 A | 10/1990 | Polaschegg |
| 4,967,940 A | 11/1990 | Blette |
| 4,974,592 A | 12/1990 | Branco |
| 4,976,687 A | 12/1990 | Martin |
| 4,979,509 A | 12/1990 | Hakky |
| 4,994,026 A | 2/1991 | Fecondini |
| 4,997,627 A | 3/1991 | Bergkuist et al. |
| 5,002,055 A | 3/1991 | Merki et al. |
| 5,006,050 A | 4/1991 | Cooke et al. |
| 5,006,111 A | 4/1991 | Inokuchi et al. |
| 5,009,251 A | 4/1991 | Pike et al. |
| 5,026,348 A | 6/1991 | Venegas |
| 5,030,199 A | 7/1991 | Barwick et al. |
| 5,034,112 A | 7/1991 | Murase et al. |
| 5,041,092 A | 8/1991 | Barwick |
| 5,045,057 A | 9/1991 | Van et al. |
| 5,046,496 A | 9/1991 | Betts et al. |
| 5,048,525 A | 9/1991 | Maxwell |
| 5,050,612 A | 9/1991 | Matsumura |
| 5,055,198 A | 10/1991 | Shettigar |
| 5,088,981 A | 2/1992 | Howson et al. |
| 5,089,421 A | 2/1992 | Dieffenbach |
| 5,096,669 A | 3/1992 | Lauks et al. |
| 5,098,377 A | 3/1992 | Borsanyi et al. |
| 5,109,850 A * | 5/1992 | Blanco et al. .................. 600/368 |
| 5,112,301 A | 5/1992 | Fenton et al. |
| 5,116,313 A | 5/1992 | Mcgregor |
| 5,137,028 A | 8/1992 | Nishimura |
| 5,145,565 A | 9/1992 | Kater et al. |
| 5,152,746 A | 10/1992 | Atkinson et al. |
| 5,161,532 A | 11/1992 | Joseph |
| 5,165,406 A | 11/1992 | Wong et al. |
| 5,165,407 A | 11/1992 | Wilson et al. |
| 5,174,291 A | 12/1992 | Schoonen et al. |
| 5,176,632 A | 1/1993 | Bernardi |
| 5,176,658 A | 1/1993 | Ranford |
| 5,178,142 A | 1/1993 | Harjunmaa et al. |
| 5,182,004 A | 1/1993 | Kohno |
| 5,188,591 A | 2/1993 | Dorsey |
| 5,195,963 A | 3/1993 | Yafuso et al. |
| 5,220,917 A | 6/1993 | Cammilli et al. |
| 5,220,920 A | 6/1993 | Gharib |
| 5,224,929 A | 7/1993 | Remiszewski |
| 5,225,063 A | 7/1993 | Gumbrecht et al. |
| 5,232,434 A | 8/1993 | Inagaki et al. |
| 5,243,982 A | 9/1993 | Mostl et al. |
| 5,254,102 A | 10/1993 | Ogawa |
| 5,264,104 A | 11/1993 | Gregg et al. |
| 5,265,594 A | 11/1993 | Olsson et al. |
| 5,269,891 A | 12/1993 | Colin |
| 5,271,815 A | 12/1993 | Wong et al. |
| 5,275,169 A | 1/1994 | Afromowitz et al. |
| 5,279,294 A | 1/1994 | Anderson et al. |
| 5,284,570 A | 2/1994 | Savage et al. |
| 5,298,022 A | 3/1994 | Bernardi |
| 5,299,571 A | 4/1994 | Mastrototaro |
| 5,302,093 A | 4/1994 | Owens et al. |
| 5,307,263 A | 4/1994 | Brown |
| 5,310,469 A | 5/1994 | Cunningham et al. |
| 5,311,908 A | 5/1994 | Barone et al. |
| 5,315,993 A | 5/1994 | Alcala |
| 5,316,008 A | 5/1994 | Suga et al. |
| 5,316,452 A | 5/1994 | Bogen et al. |
| 5,318,511 A | 6/1994 | Riquier et al. |
| 5,326,449 A | 7/1994 | Cunningham |
| 5,330,634 A | 7/1994 | Wong et al. |
| 5,331,555 A | 7/1994 | Hashimoto et al. |
| 5,335,658 A * | 8/1994 | Bedingham .................. 600/322 |
| 5,337,747 A | 8/1994 | Neftel |
| 5,342,789 A | 8/1994 | Chick et al. |
| 5,345,932 A | 9/1994 | Yafuso et al. |
| 5,352,348 A | 10/1994 | Young et al. |
| 5,354,272 A | 10/1994 | Swendson et al. |
| 5,356,375 A | 10/1994 | Higley |
| 5,356,378 A | 10/1994 | Doan |
| 5,368,562 A | 11/1994 | Blomquist et al. |
| 5,372,135 A | 12/1994 | Mendelson et al. |
| 5,372,709 A | 12/1994 | Hood |
| 5,378,229 A | 1/1995 | Layer et al. |
| 5,380,268 A | 1/1995 | Wheeler |
| 5,380,491 A | 1/1995 | Carver et al. |
| 5,380,665 A | 1/1995 | Cusack et al. |
| 5,390,671 A | 2/1995 | Lord et al. |
| 5,409,666 A | 4/1995 | Nagel et al. |
| 5,411,052 A | 5/1995 | Murray |
| 5,411,551 A | 5/1995 | Winston et al. |
| 5,417,206 A | 5/1995 | Kaneyoshi |
| 5,421,328 A | 6/1995 | Bedingham |
| 5,423,738 A | 6/1995 | Robinson et al. |
| 5,423,749 A | 6/1995 | Merte et al. |
| 5,425,375 A | 6/1995 | Chin et al. |
| 5,429,485 A | 7/1995 | Dodge |
| 5,429,602 A | 7/1995 | Hauser |
| 5,431,174 A | 7/1995 | Knute |
| 5,437,635 A | 8/1995 | Fields et al. |
| 5,445,610 A | 8/1995 | Evert |
| 5,462,051 A | 10/1995 | Oka et al. |
| 5,482,446 A | 1/1996 | Williamson et al. |
| 5,484,404 A | 1/1996 | Schulman et al. |
| 5,494,562 A | 2/1996 | Maley et al. |
| 5,497,772 A | 3/1996 | Schulman et al. |
| 5,502,396 A | 3/1996 | Desarzens et al. |
| 5,505,828 A | 4/1996 | Wong et al. |
| 5,507,288 A | 4/1996 | Bocker et al. |
| 5,509,888 A | 4/1996 | Miller |
| 5,512,046 A | 4/1996 | Pusinelli et al. |
| 5,512,248 A | 4/1996 | Van |
| 5,513,636 A | 5/1996 | Palti |
| 5,514,253 A | 5/1996 | Davis et al. |
| 5,515,851 A | 5/1996 | Goldstein |
| 5,531,679 A | 7/1996 | Schulman et al. |
| 5,531,878 A | 7/1996 | Vadgama et al. |
| 5,549,547 A | 8/1996 | Cohen et al. |
| 5,549,548 A | 8/1996 | Larsson |
| 5,549,569 A | 8/1996 | Lynn et al. |
| 5,549,651 A | 8/1996 | Lynn |
| 5,551,850 A | 9/1996 | Williamson et al. |
| 5,554,339 A | 9/1996 | Cozzette |
| 5,562,614 A | 10/1996 | O'Donnell |
| 5,562,615 A | 10/1996 | Nassif |
| 5,568,806 A | 10/1996 | Cheney, II et al. |
| 5,569,186 A | 10/1996 | Lord et al. |
| 5,569,188 A | 10/1996 | Mackool |
| 5,569,219 A | 10/1996 | Hakki et al. |
| 5,577,499 A | 11/1996 | Teves |
| 5,582,184 A | 12/1996 | Erickson et al. |
| 5,582,593 A | 12/1996 | Hultman |
| 5,586,553 A | 12/1996 | Halili et al. |
| 5,609,572 A | 3/1997 | Lang |
| 5,624,409 A | 4/1997 | Seale |
| 5,626,563 A | 5/1997 | Dodge et al. |
| 5,628,619 A | 5/1997 | Wilson |
| 5,628,890 A | 5/1997 | Carter et al. |
| 5,637,083 A | 6/1997 | Bertrand et al. |
| 5,640,470 A | 6/1997 | Iyer et al. |

| | | | | | | |
|---|---|---|---|---|---|---|
| 5,643,195 | A | 7/1997 | Drevet et al. | 6,175,752 B1 * | 1/2001 | Say et al. ............ 600/345 |
| 5,651,767 | A | 7/1997 | Schulman et al. | 6,183,437 B1 | 2/2001 | Walker |
| 5,658,250 | A | 8/1997 | Blomquist et al. | 6,191,860 B1 | 2/2001 | Klinger et al. |
| 5,660,163 | A | 8/1997 | Schulman et al. | 6,213,739 B1 | 4/2001 | Phallen et al. |
| 5,665,061 | A | 9/1997 | Antwiler | 6,233,471 B1 | 5/2001 | Berner et al. |
| 5,665,065 | A | 9/1997 | Colman et al. | 6,248,067 B1 | 6/2001 | Causey, III et al. |
| 5,667,504 | A | 9/1997 | Baumann et al. | 6,248,077 B1 | 6/2001 | Elson et al. |
| 5,676,651 | A | 10/1997 | Larson et al. | 6,248,093 B1 | 6/2001 | Moberg |
| 5,688,239 | A | 11/1997 | Walker | 6,254,586 B1 | 7/2001 | Mann et al. |
| 5,688,244 | A | 11/1997 | Lang | 6,263,222 B1 | 7/2001 | Diab et al. |
| 5,695,623 | A | 12/1997 | Michel et al. | 6,270,478 B1 | 8/2001 | Mern et al. |
| 5,697,366 | A | 12/1997 | Kimball et al. | 6,275,717 B1 | 8/2001 | Gross et al. |
| 5,697,899 | A | 12/1997 | Hillman et al. | 6,280,408 B1 | 8/2001 | Sipin |
| 5,704,354 | A | 1/1998 | Preidel et al. | 6,299,583 B1 | 10/2001 | Eggers et al. |
| 5,743,262 | A | 4/1998 | Lepper, Jr. et al. | 6,329,161 B1 | 12/2001 | Heller et al. |
| 5,749,832 | A | 5/1998 | Vadgama et al. | 6,358,225 B1 | 3/2002 | Butterfield |
| 5,755,692 | A | 5/1998 | Manicom | 6,391,019 B1 | 5/2002 | Ito |
| 5,758,643 | A | 6/1998 | Wong et al. | 6,402,703 B1 | 6/2002 | Kensey et al. |
| 5,763,760 | A | 6/1998 | Gumbrecht et al. | 6,403,944 B1 | 6/2002 | MacKenzie et al. |
| 5,779,665 | A | 7/1998 | Mastrototaro et al. | 6,424,847 B1 | 7/2002 | Mastrototaro et al. |
| 5,791,344 | A | 8/1998 | Schulman et al. | 6,430,437 B1 | 8/2002 | Marro |
| 5,791,880 | A | 8/1998 | Wilson | 6,461,496 B1 | 10/2002 | Feldman et al. |
| 5,800,383 | A | 9/1998 | Chandler et al. | 6,464,849 B1 | 10/2002 | Say et al. |
| 5,800,420 | A | 9/1998 | Gross | 6,467,480 B1 | 10/2002 | Meier et al. |
| 5,804,048 | A | 9/1998 | Wong et al. | 6,474,360 B1 | 11/2002 | Ito |
| 5,806,517 | A | 9/1998 | Gerhardt et al. | 6,484,045 B1 | 11/2002 | Holker et al. |
| 5,807,274 | A | 9/1998 | Henning et al. | 6,485,449 B2 | 11/2002 | Ito |
| 5,807,312 | A | 9/1998 | Dzwonkiewicz | 6,488,652 B1 | 12/2002 | Weijand et al. |
| 5,807,375 | A | 9/1998 | Gross et al. | 6,494,879 B2 | 12/2002 | Lennox et al. |
| 5,810,770 | A | 9/1998 | Chin et al. | 6,498,941 B1 | 12/2002 | Jackson |
| 5,820,589 | A | 10/1998 | Torgerson et al. | 6,501,976 B1 | 12/2002 | Sohrab |
| 5,837,454 | A | 11/1998 | Cozzette et al. | 6,514,718 B2 | 2/2003 | Heller et al. |
| 5,840,026 | A | 11/1998 | Uber et al. | 6,517,508 B1 | 2/2003 | Utterberg et al. |
| 5,873,862 | A | 2/1999 | Lopez | 6,520,477 B2 | 2/2003 | Trimmer |
| 5,897,525 | A | 4/1999 | Dey et al. | 6,520,937 B2 | 2/2003 | Hart et al. |
| 5,904,666 | A | 5/1999 | Dedecker et al. | 6,536,433 B1 | 3/2003 | Cewers |
| 5,911,219 | A | 6/1999 | Aylsworth et al. | 6,544,212 B2 | 4/2003 | Galley et al. |
| 5,921,951 | A | 7/1999 | Morris | 6,551,494 B1 | 4/2003 | Heller et al. |
| 5,928,155 | A | 7/1999 | Eggers et al. | 6,554,805 B2 | 4/2003 | Hiejima |
| 5,928,182 | A | 7/1999 | Kraus et al. | 6,554,822 B1 | 4/2003 | Holschneider et al. |
| 5,928,189 | A | 7/1999 | Phillips et al. | 6,558,347 B1 | 5/2003 | Jhuboo et al. |
| 5,928,195 | A | 7/1999 | Malamud et al. | 6,558,351 B1 | 5/2003 | Steil et al. |
| 5,931,814 | A | 8/1999 | Alex et al. | 6,560,471 B1 | 5/2003 | Heller et al. |
| 5,932,175 | A | 8/1999 | Knute et al. | 6,565,509 B1 | 5/2003 | Say et al. |
| 5,938,636 | A | 8/1999 | Kramer et al. | 6,565,535 B2 | 5/2003 | Zaias et al. |
| 5,947,911 | A | 9/1999 | Wong et al. | 6,565,807 B1 | 5/2003 | Patterson et al. |
| 5,957,854 | A | 9/1999 | Besson et al. | 6,572,579 B1 | 6/2003 | Raghavan et al. |
| 5,961,451 | A | 10/1999 | Reber et al. | 6,579,257 B1 | 6/2003 | Elgas et al. |
| 5,964,993 | A | 10/1999 | Blubaugh et al. | 6,585,675 B1 | 7/2003 | O'Mahony et al. |
| 5,976,085 | A | 11/1999 | Kimball et al. | 6,589,229 B1 | 7/2003 | Connelly et al. |
| 5,995,208 | A | 11/1999 | Sarge et al. | 6,594,514 B2 | 7/2003 | Berner et al. |
| 6,014,577 | A | 1/2000 | Henning et al. | 6,595,756 B2 | 7/2003 | Gray et al. |
| 6,024,720 | A | 2/2000 | Chandler et al. | 6,595,919 B2 | 7/2003 | Berner et al. |
| 6,027,445 | A | 2/2000 | Von Bahr | 6,600,940 B1 | 7/2003 | Fein et al. |
| 6,027,479 | A | 2/2000 | Alei et al. | 6,602,221 B1 | 8/2003 | Saravia et al. |
| 6,032,059 | A | 2/2000 | Henning et al. | 6,609,071 B2 | 8/2003 | Shapiro et al. |
| 6,032,667 | A | 3/2000 | Heinonen | 6,613,379 B2 | 9/2003 | Ward et al. |
| 6,059,946 | A | 5/2000 | Yukawa et al. | 6,615,061 B1 | 9/2003 | Khalil et al. |
| 6,064,900 | A | 5/2000 | Vadgama et al. | 6,618,603 B2 | 9/2003 | Varalli et al. |
| 6,066,088 | A | 5/2000 | Davis | 6,656,157 B1 | 12/2003 | Duchon et al. |
| 6,071,391 | A | 6/2000 | Gotoh et al. | 6,679,865 B2 | 1/2004 | Shekalim |
| 6,077,299 | A | 6/2000 | Adelberg et al. | 6,679,872 B2 | 1/2004 | Turovskiy et al. |
| 6,080,583 | A | 6/2000 | Von Bahr | 6,684,904 B2 | 2/2004 | Ito |
| 6,081,736 | A | 6/2000 | Colvin et al. | 6,685,668 B1 | 2/2004 | Cho et al. |
| 6,088,608 | A | 7/2000 | Schulman et al. | 6,689,089 B1 | 2/2004 | Tiedtke et al. |
| 6,090,087 | A | 7/2000 | Tsukada et al. | 6,689,265 B2 | 2/2004 | Heller et al. |
| 6,091,975 | A | 7/2000 | Daddona et al. | 6,695,860 B1 | 2/2004 | Ward et al. |
| 6,093,172 | A | 7/2000 | Funderburk et al. | 6,702,249 B2 | 3/2004 | Ito |
| 6,099,511 | A | 8/2000 | Devos et al. | 6,711,424 B1 | 3/2004 | Fine et al. |
| 6,117,290 | A | 9/2000 | Say | 6,712,796 B2 | 3/2004 | Fentis et al. |
| 6,122,536 | A | 9/2000 | Sun et al. | 6,723,086 B2 | 4/2004 | Bassuk et al. |
| 6,123,827 | A | 9/2000 | Wong et al. | 6,736,783 B2 | 5/2004 | Blake et al. |
| 6,128,519 | A | 10/2000 | Say | 6,749,587 B2 | 6/2004 | Flaherty |
| 6,134,461 | A | 10/2000 | Say et al. | 6,770,030 B1 | 8/2004 | Schaupp et al. |
| 6,159,186 | A | 12/2000 | Wickham et al. | 6,770,067 B2 | 8/2004 | Lorenzen et al. |
| 6,162,201 | A | 12/2000 | Cohen et al. | 6,780,297 B2 | 8/2004 | Matsumoto et al. |
| 6,164,921 | A | 12/2000 | Moubayed et al. | 6,801,041 B2 | 10/2004 | Karinka et al. |
| 6,165,154 | A | 12/2000 | Gray et al. | 6,802,957 B2 | 10/2004 | Jung et al. |
| 6,171,276 | B1 | 1/2001 | Lippe et al. | 6,804,002 B2 | 10/2004 | Fine et al. |

| Patent No. | Date | Inventor |
|---|---|---|
| 6,805,693 B2 | 10/2004 | Gray et al. |
| 6,811,548 B2 | 11/2004 | Jeffrey |
| 6,850,790 B2 | 2/2005 | Berner et al. |
| 6,858,020 B2 | 2/2005 | Rusnak |
| 6,862,465 B2 | 3/2005 | Shults et al. |
| 6,887,228 B2 | 5/2005 | Mckay |
| 6,895,263 B2 | 5/2005 | Shin et al. |
| 6,895,265 B2 | 5/2005 | Silver |
| 6,902,544 B2 | 6/2005 | Ludin et al. |
| 6,926,691 B2 | 8/2005 | Miethke |
| 6,931,327 B2 | 8/2005 | Goode et al. |
| 6,932,584 B2 | 8/2005 | Gray et al. |
| 6,936,006 B2 | 8/2005 | Sabra |
| 6,945,965 B2 | 9/2005 | Whiting |
| 6,948,492 B2 | 9/2005 | Wermeling et al. |
| 6,954,662 B2 | 10/2005 | Freger et al. |
| 6,960,192 B1 | 11/2005 | Flaherty et al. |
| 6,965,791 B1 | 11/2005 | Hitchcock et al. |
| 6,966,325 B2 | 11/2005 | Erickson |
| 6,975,893 B2 | 12/2005 | Say et al. |
| 6,979,315 B2 | 12/2005 | Rogers et al. |
| 6,989,891 B2 | 1/2006 | Braig et al. |
| 6,997,921 B2 | 2/2006 | Gray et al. |
| 7,022,219 B2 | 4/2006 | Mansouri et al. |
| 7,025,727 B2 | 4/2006 | Brockway et al. |
| 7,048,727 B1 | 5/2006 | Moss |
| 7,061,593 B2 | 6/2006 | Braig et al. |
| 7,063,086 B2 | 6/2006 | Shahbazpour et al. |
| 7,066,884 B2 | 6/2006 | Custer et al. |
| 7,070,577 B1 | 7/2006 | Haller et al. |
| 7,097,775 B2 | 8/2006 | Greenberg et al. |
| 7,098,803 B2 | 8/2006 | Mann et al. |
| 7,100,628 B1 | 9/2006 | Izenson et al. |
| 7,120,483 B2 | 10/2006 | Russell et al. |
| 7,131,967 B2 | 11/2006 | Gray et al. |
| 7,136,689 B2 | 11/2006 | Shults et al. |
| 7,146,202 B2 | 12/2006 | Ward et al. |
| 7,150,741 B2 | 12/2006 | Erickson et al. |
| 7,162,290 B1 | 1/2007 | Levin |
| 7,168,597 B1 | 1/2007 | Jones et al. |
| 7,184,810 B2 | 2/2007 | Caduff et al. |
| 7,207,968 B1 | 4/2007 | Harcinske |
| 7,211,074 B2 | 5/2007 | Sansoucy |
| 7,221,970 B2 | 5/2007 | Parker |
| 7,223,253 B2 | 5/2007 | Hogendijk |
| 7,228,162 B2 | 6/2007 | Ward et al. |
| 7,238,165 B2 | 7/2007 | Vincent et al. |
| 7,247,138 B2 | 7/2007 | Reghabi et al. |
| 7,254,450 B2 | 8/2007 | Christopherson et al. |
| 7,255,690 B2 | 8/2007 | Gray et al. |
| 7,258,681 B2 | 8/2007 | Houde |
| 7,266,400 B2 | 9/2007 | Fine et al. |
| 7,276,029 B2 | 10/2007 | Goode et al. |
| 7,288,085 B2 | 10/2007 | Olsen |
| 7,311,690 B2 | 12/2007 | Burnett |
| 7,313,425 B2 | 12/2007 | Finarov et al. |
| 7,314,452 B2 | 1/2008 | Madonia |
| 7,315,767 B2 | 1/2008 | Caduff et al. |
| 7,316,662 B2 | 1/2008 | Delnevo et al. |
| 7,317,939 B2 | 1/2008 | Fine et al. |
| 7,318,814 B2 | 1/2008 | Levine et al. |
| 7,327,273 B2 | 2/2008 | Hung et al. |
| 7,329,234 B2 | 2/2008 | Sansoucy |
| 7,334,594 B2 | 2/2008 | Ludin |
| 7,335,179 B2 | 2/2008 | Burnett |
| 7,335,195 B2 | 2/2008 | Mehier |
| 7,338,464 B2 | 3/2008 | Blischak et al. |
| 7,354,420 B2 | 4/2008 | Steil et al. |
| 7,361,155 B2 | 4/2008 | Sage et al. |
| 7,364,562 B2 | 4/2008 | Braig et al. |
| 7,367,942 B2 | 5/2008 | Grage et al. |
| 7,396,353 B2 | 7/2008 | Lorenzen et al. |
| 7,615,007 B2 | 11/2009 | Shults et al. |
| 7,775,975 B2 | 8/2010 | Brister et al. |
| 2001/0021817 A1 | 9/2001 | Brugger et al. |
| 2001/0039053 A1 | 11/2001 | Liseo et al. |
| 2001/0041831 A1* | 11/2001 | Starkweather et al. ....... 600/365 |
| 2002/0062132 A1* | 5/2002 | Kramer et al. ........ 606/169 |
| 2002/0065454 A1 | 5/2002 | Lebel et al. |
| 2002/0071776 A1 | 6/2002 | Bandis et al. |
| 2002/0161288 A1 | 10/2002 | Shin et al. |
| 2003/0028089 A1* | 2/2003 | Galley et al. ................ 600/365 |
| 2003/0130616 A1 | 7/2003 | Steil et al. |
| 2003/0143746 A1 | 7/2003 | Sage |
| 2003/0153821 A1 | 8/2003 | Berner |
| 2003/0235817 A1 | 12/2003 | Bartkowiak et al. |
| 2004/0054352 A1 | 3/2004 | Adames et al. |
| 2004/0078219 A1 | 4/2004 | Kaylor |
| 2004/0152187 A1 | 8/2004 | Haight et al. |
| 2004/0193025 A1 | 9/2004 | Steil et al. |
| 2004/0204687 A1 | 10/2004 | Mogensen |
| 2005/0027182 A1 | 2/2005 | Siddiqui et al. |
| 2005/0054905 A1 | 3/2005 | Corl et al. |
| 2005/0065464 A1 | 3/2005 | Talbot et al. |
| 2005/0131305 A1 | 6/2005 | Danielson et al. |
| 2005/0154271 A1 | 7/2005 | Rasdal et al. |
| 2005/0183954 A1 | 8/2005 | Hitchcock et al. |
| 2005/0197612 A1 | 9/2005 | Levin et al. |
| 2005/0288596 A1 | 12/2005 | Eigler et al. |
| 2006/0015024 A1 | 1/2006 | Brister et al. |
| 2006/0052745 A1 | 3/2006 | Van Antwerp et al. |
| 2006/0079809 A1 | 4/2006 | Goldberger et al. |
| 2006/0094946 A1 | 5/2006 | Kellogg et al. |
| 2006/0178617 A1 | 8/2006 | Adams et al. |
| 2006/0183984 A1 | 8/2006 | Dobbles et al. |
| 2006/0183985 A1 | 8/2006 | Brister et al. |
| 2006/0189863 A1 | 8/2006 | Peyser et al. |
| 2006/0189925 A1 | 8/2006 | Gable et al. |
| 2006/0224141 A1 | 10/2006 | Rush et al. |
| 2006/0229533 A1 | 10/2006 | Hoenes et al. |
| 2006/0253085 A1 | 11/2006 | Geismar et al. |
| 2006/0263839 A1 | 11/2006 | Ward et al. |
| 2006/0272652 A1 | 12/2006 | Stocker et al. |
| 2006/0293576 A1 | 12/2006 | Van Antwerp et al. |
| 2007/0085995 A1 | 4/2007 | Pesach et al. |
| 2007/0116600 A1 | 5/2007 | Kochar et al. |
| 2007/0129619 A1 | 6/2007 | Ward et al. |
| 2007/0129621 A1 | 6/2007 | Kellogg et al. |
| 2007/0135699 A1 | 6/2007 | Ward et al. |
| 2007/0142584 A1 | 6/2007 | Schorzman et al. |
| 2007/0151869 A1 | 7/2007 | Heller et al. |
| 2007/0173706 A1 | 7/2007 | Neinast et al. |
| 2007/0179436 A1 | 8/2007 | Braig et al. |
| 2007/0197889 A1 | 8/2007 | Brister et al. |
| 2007/0203407 A1 | 8/2007 | Hoss et al. |
| 2007/0206193 A1 | 9/2007 | Pesach |
| 2007/0218097 A1 | 9/2007 | Heller et al. |
| 2007/0219441 A1 | 9/2007 | Carlin |
| 2007/0225675 A1 | 9/2007 | Robinson et al. |
| 2007/0240497 A1 | 10/2007 | Robinson et al. |
| 2007/0244381 A1 | 10/2007 | Robinson et al. |
| 2007/0244382 A1 | 10/2007 | Robinson et al. |
| 2007/0249916 A1 | 10/2007 | Pesach et al. |
| 2008/0029390 A1 | 2/2008 | Roche |
| 2008/0029391 A1 | 2/2008 | Mao et al. |
| 2008/0039702 A1 | 2/2008 | Hayter et al. |
| 2008/0071157 A1 | 3/2008 | Mcgarraugh et al. |
| 2008/0071158 A1 | 3/2008 | Mcgarraugh et al. |
| 2008/0072663 A1 | 3/2008 | Keenan et al. |
| 2008/0086040 A1 | 4/2008 | Heller et al. |
| 2008/0086041 A1 | 4/2008 | Heller et al. |
| 2008/0086042 A1 | 4/2008 | Brister et al. |
| 2008/0086043 A1 | 4/2008 | Heller et al. |
| 2008/0086044 A1 | 4/2008 | Brister et al. |
| 2008/0086273 A1 | 4/2008 | Shults et al. |
| 2008/0091094 A1 | 4/2008 | Heller et al. |
| 2008/0091095 A1 | 4/2008 | Heller et al. |
| 2008/0097197 A1 | 4/2008 | Kalafut et al. |
| 2008/0108942 A1 | 5/2008 | Brister et al. |
| 2008/0119703 A1 | 5/2008 | Brister et al. |
| 2008/0119704 A1 | 5/2008 | Brister et al. |
| 2008/0119706 A1 | 5/2008 | Brister et al. |
| 2008/0125751 A1 | 5/2008 | Fjield |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2009/0018424 A1 | 1/2009 | Kamath et al. |

| | | | |
|---|---|---|---|
| 2009/0131768 | A1 | 5/2009 | Simpson et al. |
| 2009/0131769 | A1 | 5/2009 | Leach et al. |
| 2009/0131776 | A1 | 5/2009 | Simpson et al. |
| 2009/0131777 | A1 | 5/2009 | Simpson et al. |
| 2009/0137886 | A1 | 5/2009 | Shariati et al. |
| 2009/0137887 | A1 | 5/2009 | Shariati et al. |
| 2009/0143659 | A1 | 6/2009 | Li et al. |
| 2009/0204340 | A1 | 8/2009 | Feldman et al. |
| 2009/0287074 | A1 | 11/2009 | Shults et al. |
| 2010/0023270 | A1 | 1/2010 | Heller et al. |
| 2010/0081910 | A1 | 4/2010 | Brister et al. |
| 2010/0298684 | A1 | 11/2010 | Leach et al. |

FOREIGN PATENT DOCUMENTS

| | | |
|---|---|---|
| EP | 0 320 109 | 6/1989 |
| EP | 0 353 328 | 2/1990 |
| EP | 0 390 390 | 10/1990 |
| EP | 0 441 394 | 8/1991 |
| EP | 1 266 607 | 12/2002 |
| GB | 2149918 | 6/1985 |
| WO | WO 89/02720 | 4/1989 |
| WO | WO 91/16416 | 10/1991 |
| WO | WO 93/14693 | 8/1993 |
| WO | WO 93/23744 | 11/1993 |
| WO | WO 96/14026 | 5/1996 |
| WO | WO 96/25089 | 8/1996 |
| WO | WO 97/01986 | 1/1997 |
| WO | WO 97/06727 | 2/1997 |
| WO | WO 99/56613 | 4/1999 |
| WO | WO 00/59373 | 10/2000 |
| WO | WO 00/74753 | 12/2000 |
| WO | WO 01/58348 A2 | 8/2001 |
| WO | WO 2005/026689 | 10/2005 |
| WO | WO 2007/002209 | 1/2007 |
| WO | WO 2007/097754 | 8/2007 |
| WO | WO 2007/137286 | 11/2007 |
| WO | WO 2008/001091 | 1/2008 |

OTHER PUBLICATIONS

Alcock & Turner. 1994. Continuous Analyte Monitoring to Aid Clinical Practice. IEEE Engineering in Med. & Biol. Mag. 13:319-325.
Aussedat et al. 1997. A user-friendly method for calibrating a subcutaneous glucose sensor-based hypoglycaemic alarm. Biosensors & Bioelectronics 12(11):1061-1071.
Freedman et al. 1991. Statistics, Second Edition, W.W. Norton & Company, p. 74.
Hamilton Syringe Selection Guide. 2006. Syringe Selection. www.hamiltoncompany.com.
Hoel, Paul G. 1976. Elementary Statistics, Fourth Edition. John Wiley & Sons, Inc.. pp. 113-114.
Jablecki et al. 2000. Simulations of the frequency response of implantable glucose sensors. Analytical Chemistry 72:1853-1859.
Jaffari et al. 1995. Recent advances in amperometric glucose biosensors for in vivo monitoring, Physiol. Meas. 16: 1-15.
Kerner et al. 1988. A potentially implantable enzyme electrode for amperometric measurement of glucose, Horm Metab Res Suppl. 20:8-13.
Kost et al. 1985. Glucose-sensitive membranes containing glucose oxidase: activity, swelling, and permeability studies, Journal of Biomedical Materials Research 19:1117-1133.
Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.
Marena et al. 1993. The artificial endocrine pancreas in clinical practice and research. Panminerva Medica 35(2): 67-74.
Moatti-Sirat et al. 1992. Evaluating in vitro and in vivo the interference of ascorbate and acetaminophen on glucose detection by a needle-type glucose sensor, Biosensors & Bioelectronics 7:345-352.
Moatti-Sirat et al. Jun. 1994. Reduction of acetaminophen interference in glucose sensors by a composite Nafion membrane: demonstration in rats and man, Diabetologia 37(6):610-616.
Mosbach et al. 1975. Determination of heat changes in the proximity of immobilized enzymes with an enzyme thermistor and its use for the assay of metabolites, Biochim. Biophys. Acta. 403:256-265.

Motonaka et al. 1993. Determination of cholesterol and cholesterol ester with novel enzyme microsensors, Anal. Chem. 65:3258-3261.
Muslu. 1991. Trickling filter performance. Applied Biochem. Biotech. 37:211-224.
Pickup et al. 1993. Developing glucose sensors for in vivo use. Elsevier Science Publishers Ltd (UK), TIBTECH vol. 11: 285-291.
Rabah et al., 1991. Electrochemical wear of graphite anodes during electrolysis of brine, Carbon, 29(2):165-171.
Rebrin et al. 1992. Subcutaneous glucose monitoring by means of electrochemical sensors: fiction or reality? J. Biomed. Eng. 14:33-40.
Reusch. 2004. Chemical Reactivity. Organometallic Compounds. Virtual Textbook of Organic Chem. pp. 1-16, http://www.cem.msu.edu/~reusch/VirtualText/orgmetal.htm.
Rhodes et al. 1994. Prediction of pocket-portable and implantable glucose enzyme electrode performance from combined species permeability and digital simulation analysis. Analytical Chemistry 66(9):1520-1529.
Rigla et al. 2008. Real-time continuous glucose monitoring together with telemedical assistance improves glycemic control and glucose stability in pump-treated patients. Diab. Thechnol. & Therapeut., 10(3):194-199.
Samuels, M.P. 2004. The effects of flight and altitude. Arch Dis Child. 89: 448-455.
Schmidtke et al. Jan. 1998. Measurement and modeling of the transient difference between blood and subcutaneous glucose concentrations in the rat after injection of insulin. *Proc Natl Aced Sci USA*, 95: 294-299.
Shichiri et al. 1985. Needle-type Glucose Sensor for Wearable Artificial Endocrine Pancreas in Implantable Sensors 197-210.
Takegami et al. 1992. Pervaporation of ethanol water mixtures using novel hydrophobic membranes containing polydimethylsiloxane, Journal of Membrane Science, 75: 93-105.
Tierney et al. 2000. Effect of acetaminophen on the accuracy of glucose measurements obtained with the GlucoWatch biographer. Diabetes Technol Ther 2(2):199-207.
Thome et al. 1995. Abstract: Can the decrease in subcutaneous glucose concentration precede the decrease in blood glucose level? Proposition for a push-pull kinetics hypothesis, Horm. Metab. Res. 27:53.
Updike et al. 2000. A subcutaneous glucose sensor with improved longevity, dynamic range, and stability of calibration. Diabetes Care 23(2):208-214.
Vadgama. 1988. Diffusion limited enzyme electrodes. NATO ASI Series: Series C, Math and Phys. Sci. 226:359-377.
Ward et al. 2000. Understanding Spontaneous Output Fluctuations of an Amperometric Glucose Sensor: Effect of Inhalation Anesthesia and use of a Nonenzyme Containing Electrode. ASAIO Journal 540-546.
Ward et al. 2004. A wire-based dual-analyte sensor for Glucose and Lactate: In Vitro and In Vivo Evaluation, Diab Tech Therapeut. 6(3): 389-401.
Wiley Electrical and Electronics Engineering Dictionary. 2004. John Wiley & Sons, Inc. pp. 141, 142, 548, 549.
Wilkins et al. 1995. Integrated implantable device for long-term glucose monitoring. Biosens. Bioelectron 10:485-494.
Ye et al. 1993. High Current Density 'Wired' Quinoprotein Glucose Dehydrogenase Electrode. Anal. Chem. 65:238-241.
Zhang et al. 1993. In vitro and in vivo evaluation of oxygen effects on a glucose oxidase based implantable glucose sensor. Analytica Chimica Acta, 281:513-520.
Zhu et al. 2002. Planar amperometric glucose sensor based on glucose oxidase immobilized by chitosan film on prussian blue layer. Sensors, 2:127-136.
Ziaie et al. 1997. A single-channel implantable microstimulator for functional neuromuscular stimulation. IEEE Transactions on Biomedical Engineering 44(10):909-920.
IPRP dated Sep. 28, 2010 for PCT/US2008/082870, filed Nov. 7, 2008.
IPRP dated Sep. 28, 2010 for PCT/US2008/082905, Filed Nov. 7, 2008.
EPO Communication dated Aug. 18, 011 for Application No. 07843011.3, filed Apr. 10, 2008.

EFS File History for U.S. Appl. No. 11/543,396, filed Oct. 4, 2006 containing Office Actions dated Dec. 8, 2010, Mar. 3, 2011 and Aug. 2, 2011 and Applicant Responses filed Dec. 13, 2010, Jun. 3, 2011 and Sep. 23, 2011 as of Oct. 6, 2011.

EFS File History for U.S. Appl. No. 11/543,490, filed Oct. 4, 2006 containing Office Actions dated Jan. 3, 2011, Mar. 11, 2011 and Oct. 12, 2011 and Applicant Responses filed Feb. 3, 2011 and Jul. 11, 2011 as of Oct. 14, 2011.

EFS File History for U.S. Appl. No. 11/543,404, filed Oct. 4, 2006 containing Office Actions dated Jun. 29, 2011 and Aug. 19, 2011 and Applicant Response(s) filed Jul. 29, 22 as of Oct. 17, 2011.

EFS File History for U.S. Appl. No. 11/691,432, filed Mar. 26, 2007 (now USP 7,775,975, issued Aug. 17, 2010) containing Office Action(s) dated Jul. 28, 2008, Sep. 19, 2008, Mar. 4, 2009, Jun. 10, 2009, Nov. 30, 2009, Feb. 18, 2010, Apr. 2, 2010 and Jun. 16, 2010 and Applicant Response(s) filed Aug. 12, 2008, Nov. 26, 2008, Mar. 12, 2009, Jul. 22, 2009 and Jan. 29, 2010, Feb. 26, 2010 and Apr. 9, 2010, Uploaded in 2 parts.

EFS File History for U.S. Appl. No. 11/691,424, filed Mar. 26, 2007 containing Office Action(s) dated Sep. 25, 2008, Feb. 18, 2009, Jun. 11, 2009, Nov. 12, 2009 and Dec. 8, 2009 and Applicant Response(s) filed Nov. 24, 2008, Feb. 18, 2009, Mar. 4, 2009, Jul. 9, 2009, Nov. 19, 2009 and Feb. 8, 2010 as of Oct. 17, 2011, Uploaded in 2 parts.

EFS File History for U.S. Appl. No. 11/691,466, filed Mar. 26, 2007 (USP 7,615,007, issued Nov. 10, 2009) containing Office Action(s) dated Oct. 3, 2008, Apr. 17, 2009 and Jul. 17, 2009 and Applicant Response(s) filed Dec. 3, 2008 and Jun. 17, 2009.

EFS File History for U.S. Appl. No. 12/055,149, filed Mar. 25, 2008 containing Office Action(s) dated Jun. 13, 2011 and Applicant Response(s) filed Oct. 13, 2011 as of Oct. 17, 2011.

EFS File History for U.S. Appl. No. 12/055,227, filed Mar. 25, 2008 containing Office Action(s) dated Sep. 9, 2011 and Applicant Response(s) filed Oct. 11, 2011 as of Oct. 17, 2011.

EFS File History for U.S. Appl. No. 12/267,547, filed Nov. 7, 2008 containing Office Action(s) dated Sep. 13, 2011 as of Oct. 17, 2011.

EFS File History for U.S. Appl. No. 12/267,546, filed Nov. 7, 2008 containing Office Action(s) dated Sep. 12, 2011 as of Oct. 17, 2011.

EFS File History for U.S. Appl. No. 12/267,545, filed Nov. 7, 2008 containing Office Action(s) dated Sep. 7, 2011 as of Oct. 17, 2011.

Bellucci et al. Jan. 1986. Electrochemical behaviour of graphite-epoxy composite materials (GECM) in aqueous salt solutions, Journal of Applied Electrochemistry, 16(1):15-22.

Bindra et al. 1991. Design and In Vitro Studies of a Needle-Type Glucose Senso for Subcutaneous Monitoring. Anal. Chem 63:1692-96.

Bobbioni-Harsch et al. 1993. Lifespan of subcutaneous glucose sensors and their performances during dynamic glycaemia changes in rats, J. Biomed. Eng. 15:457-463.

Brooks et al. "Development of an on-line glucose sensor for fermentation monitoring," Biosensors, 3:45-56 (1987/88).

Cass et al. "Ferrocene-mediated enzyme electrodes for amperometric determination of glucose," Anal. Chem., 36:667-71 (1984).

Davies, et al. 1992. Polymer membranes in clinical sensor applications. I. An overview of membrane function, Biomaterials, 13(14):971-978.

Fahy et al., An analysis: hyperglycemic intensive care patients need continuous glocuse monitoring—easier said than done, Journal of Diabetese Science and Technology, 2(2):201-204, Mar. 2008.

Ganesh et al., Evaluation of the VIA® blood chemistry monitor for glucose in healthy and diabetic volunteers, Journal of Diabetese Science and Technology, 2(2):182-193, Mar. 2008.

Heller, "Electrical wiring of redox enzymes," *Acc. Chem. Res.*, 23:128-134 (1990).

Heller, A. 1992. Electrical Connection of Enzyme Redox Centers to Electrodes. J. Phys. Chem. 96:3579-3587.

Hicks, 1985. In Situ Monitoring, Clinical Chemistry, 31(12):1931-1935.

Hu, et al. 1993. A needle-type enzyme-based lactate sensor for in vivo monitoring, Analytica Chimica Acta, 281:503-511.

Johnson (1991). "Reproducible electrodeposition of biomolecules for the fabrication of miniature electroenzymatic biosensors," *Sensors and Actuators B*, 5:85-89.

Johnson et al. 1992. In vivo evaluation of an electroenzymatic glucose sensor implanted in subcutaneous tissue. Biosensors & Bioelectronics, 7:709-714.

Kawagoe et al. 1991. Enzyme-modified organic conducting salt microelectrode, Anal. Chem. 63:2961-2965.

Kunjan et al., Automated blood sampling and glocuse sensing in critical care settings, Journal of Diabetes Science and Technology 2(3):194-200, Mar. 2008.

Maidan et al. 1992. Elimination of Electrooxidizable Interferent-Produced Currents in Amperometric Biosensors, Analytical Chemistry, 64:2889-2896.

Mastrototaro et al. "An electroenzymatic glucose sensor fabricated on a flexible substrate," Sensors and Actuators B, 5:139-44 (1991).

McKean, et al. Jul. 7, 1988. A Telemetry Instrumentation System for Chronically Implanted Glucose and Oxygen Sensors. Transactions on Biomedical Engineering 35:526-532.

Moatti-Sirat et al. 1992. Towards continuous glucose monitoring: in vivo evaluation of a miniaturized glucose sensor implanted for several days in rat subcutaneous tissue. Diabetologia 35:224-230.

Murphy, et al. 1992. Polymer membranes in clinical sensor applications. II. The design and fabrication of permselective hydrogels for electrochemical devices, Biomaterials, 13(14):979-990.

Ohara, et al. Dec. 1993. Glucose electrodes based on cross-linked bis(2,2'- bipyridine)chloroosmium(+/2+) complexed poly(1-vinylimidazole) films, Analytical Chemistry, 65:3512-3517.

Pickup et al. "Implantable glucose sensors: choosing the appropriate sensing strategy," Biosensors, 3:335-346 (1987/1988).

Pickup et al. "In vivo molecular sensing in diabetes mellitus: an implantable glucose sensor with direct electron transfer," Diabetologia, 32:213-217 (1989).

Pishko et al. "Amperometric glucose microelectrodes prepared through immobilization of glucose oxidase in redox hydrogels," Anal. Chem., 63:2268-72 (1991).

Poitout, et al. 1991. In Vitro and In Vivo Evaluation in Dogs of a Miniaturized Glucose Sensor, ASAIO Transactions, 37:M298-M300.

Reach et al. 1992. Can continuous glucose monitoring be used for the treatment of diabetes? Analytical Chemistry 64(5):381-386.

Rebrin et al. "Automated feedback control of subcutaneous glucose concentration in diabetic dogs," Diabetologia, 32:573-76 (1989).

Sakakida et al. 1993. Ferrocene-Mediated Needle Type Glucose Sensor Covered with Newly Designed Biocompatible Membran, Sensors and Actuators B 13-14:319-322.

Shaw et al. "In vitro testing of a simply constructed, highly stable glucose sensor suitable for implantation in diabetic patients," Biosensors & Bioelectronics, 6:401-406 (1991).

Shichiri et al. 1989. Membrane Design for Extending the Long-Life of an Implantable Glucose Sensor. Diab. Nutr. Metab. 2:309-313.

Shults et al. 1994. A telemetry-instrumentation system for monitoring multiple subcutaneously implanted glucose sensors. IEEE Transactions on Biomedical Engineering 41(10):937-942.

Sternberg et al. 1988. Study and Development of Multilayer Needle-type Enzyme-based Glucose Microsensors. Biosensors 4:27-40.

Torjman et al., Glucose monitoring in acute care: technologies on the horizon, Journal of Deabetes Science and Technology, 2(2):178-181, Mar. 2008.

von Woedtke et al. 1989. In situ calibration of implanted electrochemical glucose sensors. Biomed Biochim. Acta 48(11/12):943-952.

Wilson et al. 1992. Progress toward the development of an implantable sensor for glucose. Clin. Chem. 38(9):1613-1617.

Worsley et al., Measurement of glucose in blood with a phenylboronic acid optical sensor, Journal of Diabetes Science and Technology, 2(2):213-220, Mar. 2008.

Yang et al (1996). "A glucose biosensor based on an oxygen electrode: In-vitro performances in a model buffer solution and in blood plasma," Biomedical Instrumentation & Technology, 30:55-61.

IPRP for PCT/US07/079220, filed Sep. 21, 2007.

ISR and WO for PCT/US08/082905, filed Nov. 7, 2008.

ISR and WO for PCT/US08/82870, filed Nov. 7, 2008.

Office Action dated Mar. 31, 2008 in U.S. Appl. No. 11/077,759.

Office Action dated Jul. 10, 2008 in U.S. Appl. No. 11/077,759.

Office Action dated Aug. 11, 2008 in U.S. Appl. No. 11/360,819.

Office Action dated Dec. 26, 2008 in U.S. Appl. No. 11/360,819.
Office Action dated May 26, 2009 in U.S. Appl. No. 11/077,759.
Office Action dated Jun. 10, 2009 in U.S. Appl. No. 11/691,432.
Office Action dated Jun. 11, 2009 in U.S. Appl. No. 11/691,424.
Armour et al. Dec. 1990. Application of Chronic Intravascular Blood Glucose Sensor in Dogs. Diabetes 39:1519-1526.
Bode, B. W. 2000. Clinical utility of the continuous glucose monitoring system. Diabetes Technol Ther, 2(Suppl 1):S35-41.
Chia et al. 2004. Glucose sensors: toward closed loop insulin delivery. Endocrinol Metab Clin North Am 33:175-95.
Edwards Lifesciences. Accuracy for your and your patients. Marketing materials, 4 pp. 2002.
Frost et al. 2002. Implantable chemical sensors for real-time clinical monitoring: Progress and challenges. Current Opinion in Chemical Biology 6:633-641.
Kiechle, F.L. 2001. The impact of continuous glucose monitoring on hospital point-of-care testing programs. Diabetes Technol Ther 3:647-649.
Kurtz et al. 2005. Recommendations for blood pressure measurement in humans and experimental animals, Part 2: Blood pressure measurement in experimental animals, A statement for professionals from the subcommittee of professional and public education of the American Heart Association Council on High Blood Pressure Research. Hypertension 45:299-310.
Rivers et al., Central venous oxygen saturation monitoring in the critically ill patient, Current Opinion in Critical Care, 7:204-211, 2001.
Shichiri et al. 1983. Glycaemic Control in Pancreatectomized Dogs with a Wearable Artificial Endocrine Pancreas. Diabetologia 24:179-184.
Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.
Skyler, J. S. 2000. The economic burden of diabetes and the benefits of improved glycemic control: The potential role of a continuous glucose monitoring system. Diabetes Technology & Therapeutics 2 Suppl 1:S7-12.
Thompson et al., In Vivo Probes: Problems and Perspectives, Department of Chemistry, University of Toronto, Canada, pp. 255-261, 1986.
Turner, A.P.F. 1988. Amperometric biosensor based on mediator-modified electrodes. Methods in Enzymology 137:90-103.
Unger et al. 2004. Glucose control in the hospitalized patient. Emerg Med 36(9):12-18.
Updike et al. 1997. Principles of long-term fully impleated sensors with emphasis on radiotelemetric monitoring of blood glucose form inside a subcutaneous foreign body capsule (FBC). In Fraser, ed., Biosensors in the Body. New York. John Wiley & Sons, pp. 117-137.
Utah Medical Products Inc., Blood Pressure Tranducers product specifications. 6 pp. 2003-2006, 2003.
Van den Berghe 2004. Tight blood glucose control with insulin in "real-life" intensive care. Mayo Clin Proc 79(8):977-978.
Velho et al. 1989. Strategies for calibrating a subcutaneous glucose sensor. Biomed Biochim Acta 48(11/12):957-964, 1989.
"Intravenous therapy," http://en.wikipedia.org/wiki/Intravenous_therapy, Aug. 15, 2006, 6 pp.
Zamzow et al. Development and evaluation of a wearable blood glucose monitor. pp. M588-M591, 1990.
Office Action dated Sep. 19, 2008 in U.S. Appl. No. 11/691,432.
Office Action dated Sep. 25, 2008 in U.S. Appl. No. 11/691,424.
Office Action dated Oct. 3, 2008 in U.S. Appl. No. 11/691,466.
Invitation to Pay Additional Fees for PCT/US07/079220, filed Sep. 21, 2007.
ISR and WO for PCT/US07/079220, filed Sep. 21, 2007.
Leonhardt et al., The Potential use of silicon compounds as oxygen carriers for free and immobilized cells containing L-amino acid oxidase, Appl Microbiol Biotechnol. (1985) 21: 162-166.

* cited by examiner

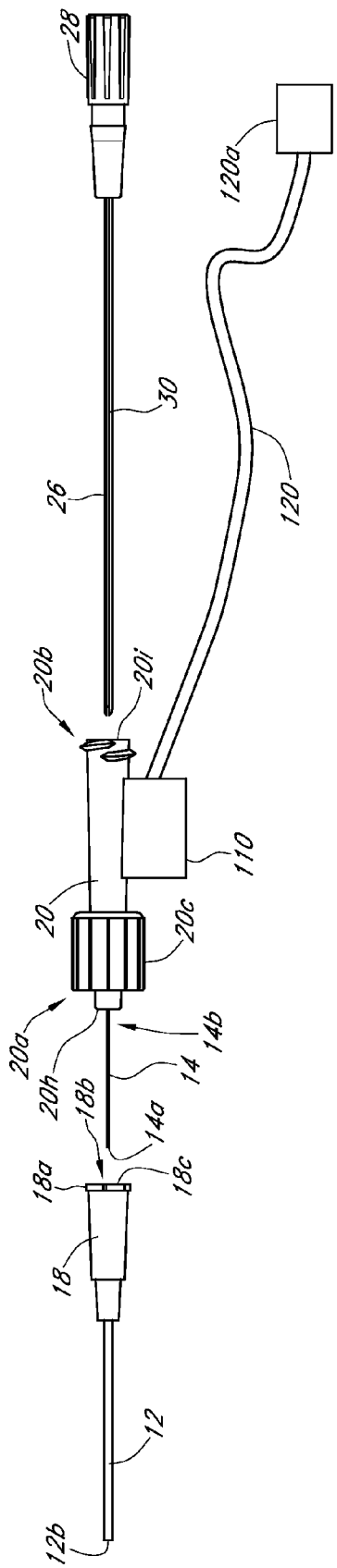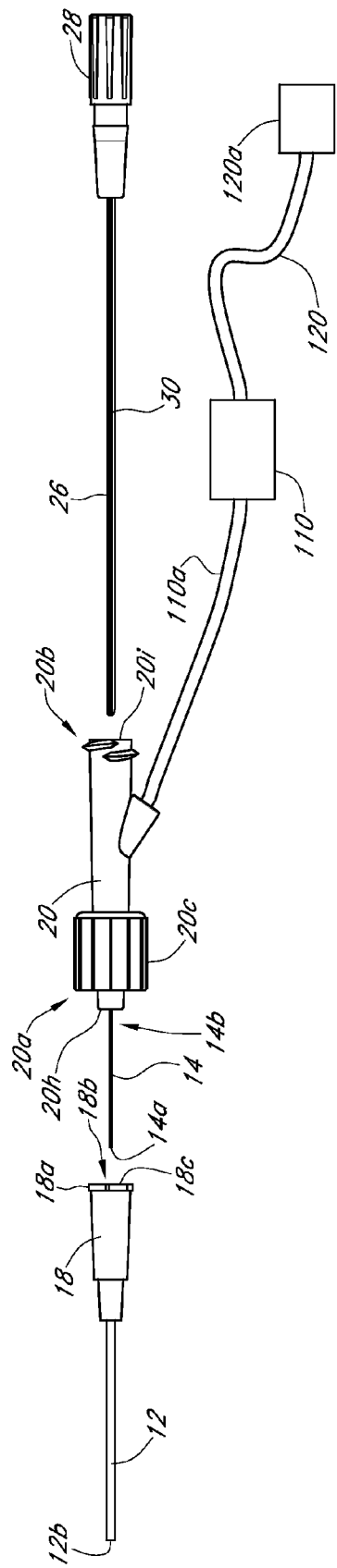
FIG. 3A
FIG. 3B

INTEGRATED DEVICE FOR CONTINUOUS IN VIVO ANALYTE DETECTION AND SIMULTANEOUS CONTROL OF AN INFUSION DEVICE

CROSS-REFERENCE TO RELATED APPLICATIONS

This application is a continuation-in-part of U.S. application Ser. No. 12/055,114 filed Mar. 25, 2008; and is a continuation-in-part of U.S. application Ser. No. 12/055,078 filed Mar. 25, 2008; and is a continuation-in-part of U.S. application Ser. No. 12/055,149 filed Mar. 25, 2008; and is a continuation-in-part of U.S. application Ser. No. 12/055,203 filed Mar. 25, 2008; and is a continuation-in-part of U.S. application Ser. No. 12/055,227 filed Mar. 25, 2008. U.S. application Ser. No. 12/055,227 is a continuation-in-part of U.S. application Ser. No. 11/691,466 filed Mar. 26, 2007 and issued as U.S. Pat. No. 7,615,007 on Nov. 10, 2009; and is a continuation-in-part of U.S. application Ser. No. 11/691,424 filed Mar. 26, 2007; and is a continuation-in-part of U.S. application Ser. No. 11/691,432 filed Mar. 26, 2007 and issued as U.S. Pat. No. 7,775,975 on Aug. 17, 2010; and is a continuation-in-part of U.S. application Ser. No. 11/691,426 filed Mar. 26, 2007. U.S. application Ser. No. 12/055,203 is a continuation-in-part of U.S. application Ser. No. 11/691,466 filed Mar. 26, 2007 and issued as U.S. Pat. No. 7,615,007 on Nov. 10, 2009; and is a continuation-in-part of U.S. application Ser. No. 11/691,424 filed Mar. 26, 2007; and is a continuation-in-part of U.S. application Ser. No. 11/691,432 filed Mar. 26, 2007 and issued as U.S. Pat. No. 7,775,975 on Aug. 17, 2010; and is a continuation-in-part of U.S. application Ser. No. 11/691,426 filed Mar. 26, 2007. U.S. application Ser. No. 12/055,149 is a continuation-in-part of U.S. application Ser. No. 11/691,466 filed Mar. 26, 2007 and issued as U.S. Pat. No. 7,615,007 on Nov. 10, 2009; and is a continuation-in-part of U.S. application Ser. No. 11/691,424 filed Mar. 26, 2007; and is a continuation-in-part of U.S. application Ser. No. 11/691,432 filed Mar. 26, 2007 and issued as U.S. Pat. No. 7,775,975 on Aug. 17, 2010; and is a continuation-in-part of U.S. application Ser. No. 11/691,426 filed Mar. 26, 2007. U.S. application Ser. No. 12/055,114 is a continuation-in-part of U.S. application Ser. No. 11/691,466 filed Mar. 26, 2007 and issued as U.S. Pat. No. 7,615,007 on Nov. 10, 2009; and is a continuation-in-part of U.S. application Ser. No. 11/691,424 filed Mar. 26, 2007; and is a continuation-in-part of U.S. application Ser. No. 11/691,432 filed Mar. 26, 2007 and issued as U.S. Pat. No. 7,775,975 on Aug. 17, 2010; and is a continuation-in-part of U.S. application Ser. No. 11/691,426 filed Mar. 26, 2007. U.S. application Ser. No. 12/055,078 is a continuation-in-part of U.S. application Ser. No. 11/691,466 filed Mar. 26, 2007 and issued as U.S. Pat. No. 7,615,007 on Nov. 10, 2009; and is a continuation-in-part of U.S. application Ser. No. 11/691,424 filed Mar. 26, 2007; and is a continuation-in-part of U.S. application Ser. No. 11/691,432 filed Mar. 26, 2007 and issued as U.S. Pat. No. 7,775,975 on Aug. 17, 2012; and is a continuation-in-part of U.S. application Ser. No. 11/691,426 filed Mar. 26, 2007. U.S. application Ser. No. 12/055,078 is a continuation-in-part of U.S. application Ser. No. 11/543,683 filed Oct. 4, 2006 and issued as U.S. Pat. No. 7,366,556 on Apr. 29, 2008, which is a continuation-in-part of U.S. application Ser. No. 11/004,561 filed Dec. 3, 2004 and issued as U.S. Pat. No. 7,715,893 on May 11, 2010, which claims the benefit of U.S. Provisional Application No. 60/527,323 filed Dec. 5, 2003, U.S. Provisional Application No. 60/587,787, filed Jul. 13, 2004, and U.S. Provisional Application No. 60/614,683, filed Sep. 30, 2004. U.S. application Ser. No. 12/055,078 is a continuation-in-part of U.S. application Ser. No. 11/865,572, filed Oct. 1, 2007, which is a continuation-in-part of U.S. application Ser. No. 11/543,683 filed Oct. 4, 2006 and issued as U.S. Pat. No. 7,366,556 on Apr. 29, 2008. U.S. application Ser. No. 11/691,466 filed Mar. 26, 2007 and issued as U.S. Pat. No. 7,615,007 on Nov. 10, 2009 is a continuation-in-part of U.S. application Ser. No. 11/543,396 filed Oct. 4, 2006; and is a continuation-in-part of U.S. application Ser. No. 11/543,490 filed Oct. 4, 2006; and is a continuation-in-part of U.S. application Ser. No. 11/543,404 filed Oct. 4, 2006. U.S. application Ser. No. 11/691,432 filed Mar. 26, 2007 and issued as U.S. Pat. No. 7,775,975 on Aug. 17, 2012 is a continuation-in-part of U.S. application Ser. No. 11/543,396 filed Oct. 4, 2006; and is a continuation-in-part of U.S. application Ser. No. 11/543,490 filed Oct. 4, 2006; and is a continuation-in-part of U.S. application Ser. No. 11/543,404 filed Oct. 4, 2006. U.S. application Ser. No. 11/691,426 filed Mar. 26, 2007 is a continuation-in-part of U.S. application Ser. No. 11/543,396 filed Oct. 4, 2006; and is a continuation-in-part of U.S. application Ser. No. 11/543,490 filed Oct. 4, 2006; and is a continuation-in-part of U.S. application Ser. No. 11/543,404 filed Oct. 4, 2006. U.S. application Ser. No. 11/691,424 filed Mar. 26, 2007 is a continuation-in-part of U.S. application Ser. No. 11/543,396 filed Oct. 4, 2006; and is a continuation-in-part of U.S. application Ser. No. 11/543,490 filed Oct. 4, 2006; and is a continuation-in-part of U.S. application Ser. No. 11/543,404 filed Oct. 4, 2006. The disclosures of each of the abovementioned applications is hereby expressly incorporated by reference in its entirety and is hereby expressly made a portion of this application.

FIELD OF THE INVENTION

The preferred embodiments relate generally to continuous analyte detection in the circulatory system and electronic control of infusion devices.

BACKGROUND OF THE INVENTION

In today's hospital setting, especially in intensive care units (ICUs), it is routine to access a patient's circulatory system, both to retrieve blood samples for analysis and for infusion of a variety of fluid formulations, such as but not limited to hydration fluids, medicaments and nutrients. For example, patients having heart, vascular, neurologic and orthopedic surgeries may have 2, 3 or more catheters in place, for fluid infusion and sample withdrawal. In some circumstances, a hospital patient is continuously monitored for changes in some blood analyte levels, such as for diagnosing, monitoring and/or prognosticating a patient's medical status. In some circumstances, blood samples are collected at regular intervals, and sent to a laboratory analysis. In other circumstances, a bedside analyte monitor is used to monitor the levels of the analyte.

SUMMARY OF THE INVENTION

In a first aspect a system for analyte detection in and fluid infusion into a host is provided, comprising: an analyte sensor configured and arranged to generate a signal associated with an analyte; a vascular access device configured for fluid communication with a circulatory system of the host, wherein the analyte sensor is associated with the vascular access device such that fluid flow through the vascular access device passes the analyte sensor; and system electronics operably connected to the analyte sensor and configured to process the signal, wherein the system electronics comprise: a processor module configured to control a flow profile of a flow control device, wherein the flow profile is configured to intermittently control flow of a fluid through the vascular access device into the circulatory system of the host and to intermittently control a flow of a sample from the circulatory system of the host into the vascular access device when the vascular access device is in fluid communication with the circulatory system of the host and operably connected to the flow control device; and an output module configured and arranged to operably connect with the flow control device so as to enable the processor module to control the flow profile of the flow control device.

In an embodiment of the first aspect, the system further comprises a cable operably coupled to the system electronics, wherein the cable is configured and arranged to operably connect with a flow control device.

In an embodiment of the first aspect, the system electronics are physically connected to the cable such that the system electronics are located within a distance of about 8 feet or less of the analyte sensor.

In an embodiment of the first aspect, the system electronics are located on the electrical cable, such that the system electronics are located within a distance of about 6 feet or less of the analyte sensor.

In an embodiment of the first aspect, the system electronics are located on the electrical cable, such that the system electronics are located within a distance of about 3 feet or less of the analyte sensor.

In an embodiment of the first aspect, the system electronics are configured and arranged to be powered at least in part by a flow control device.

In an embodiment of the first aspect, the system electronics are actuated upon engagement of the system electronics with a flow control device.

In an embodiment of the first aspect, the system electronics are non-releasably connected with the analyte sensor.

In an embodiment of the first aspect, the system electronics are releasably connected to the analyte sensor.

In an embodiment of the first aspect, the output module is configured and arranged for wireless communication with a flow control device.

In an embodiment of the first aspect, the processor module comprises a fail-safe module.

In an embodiment of the first aspect, the system electronics are configured to process the signal to obtain one or more sensor analyte values, and wherein the flow profile is determined based at least in part on the one or more sensor analyte values.

In an embodiment of the first aspect, the system further comprises a source of a solution comprising a medicament.

In an embodiment of the first aspect, the flow profile is configured to intermittently control flow of the solution comprising the medicament through the vascular access device into the circulatory system of the host.

In an embodiment of the first aspect, the vascular access device comprises a catheter, wherein the analyte sensor comprises an electrode, and wherein the electrode is located within or on the catheter.

In an embodiment of the first aspect, the vascular access device comprises a fluid coupler comprising a first end configured and arranged for fluid communication with a catheter configured for implantation in a host's circulatory system and a second end configured and arranged for fluid communication with tubing associated with a flow control device.

In an embodiment of the first aspect, at least a portion of the analyte sensor is located within the vascular access device.

In an embodiment of the first aspect, the analyte sensor is located within a distance of about 40 mm or less of an opening in the vascular access device through which a biological sample from the circulatory system of the host is obtained when the vascular access device is in fluid communication with the circulatory system of the host.

In an embodiment of the first aspect, the analyte sensor is located such that the analyte sensor is bathed in a biological sample from the circulatory system of the host when a volume of about 300 µl or less of the biological sample is drawn back into the vascular access device when the vascular access device is in fluid communication with the circulatory system of the host.

In an embodiment of the first aspect, the analyte sensor is configured and arranged to continuously measure glucose in a host.

In an embodiment of the first aspect, the analyte sensor is configured and arranged to measure a signal associated with at least one analyte selected from the group consisting of albumin, alkaline phosphatase, alanine transaminase, aspartate aminotransferase, bilirubin, blood urea nitrogen, calcium, CO2, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker, and a drug.

In an embodiment of the first aspect, the system further comprises a flow control device configured and arranged for fluid communication with the vascular access device and configured to intermittently infuse a fluid and draw back a biological sample of the circulatory system responsive to the flow profile.

In an embodiment of the first aspect, the flow control device comprises a pump.

In an embodiment of the first aspect, the pump comprises a bi-directional pump.

In an embodiment of the first aspect, the pump comprises a peristaltic pump.

BRIEF DESCRIPTION OF THE DRAWINGS

FIG. 3A is a side view of an analyte detection and electronic cable system, in one embodiment.

FIG. 3B is a side view of an analyte detection and electronic cable system, in another embodiment.

DETAILED DESCRIPTION OF THE PREFERRED EMBODIMENT

Figure 1:
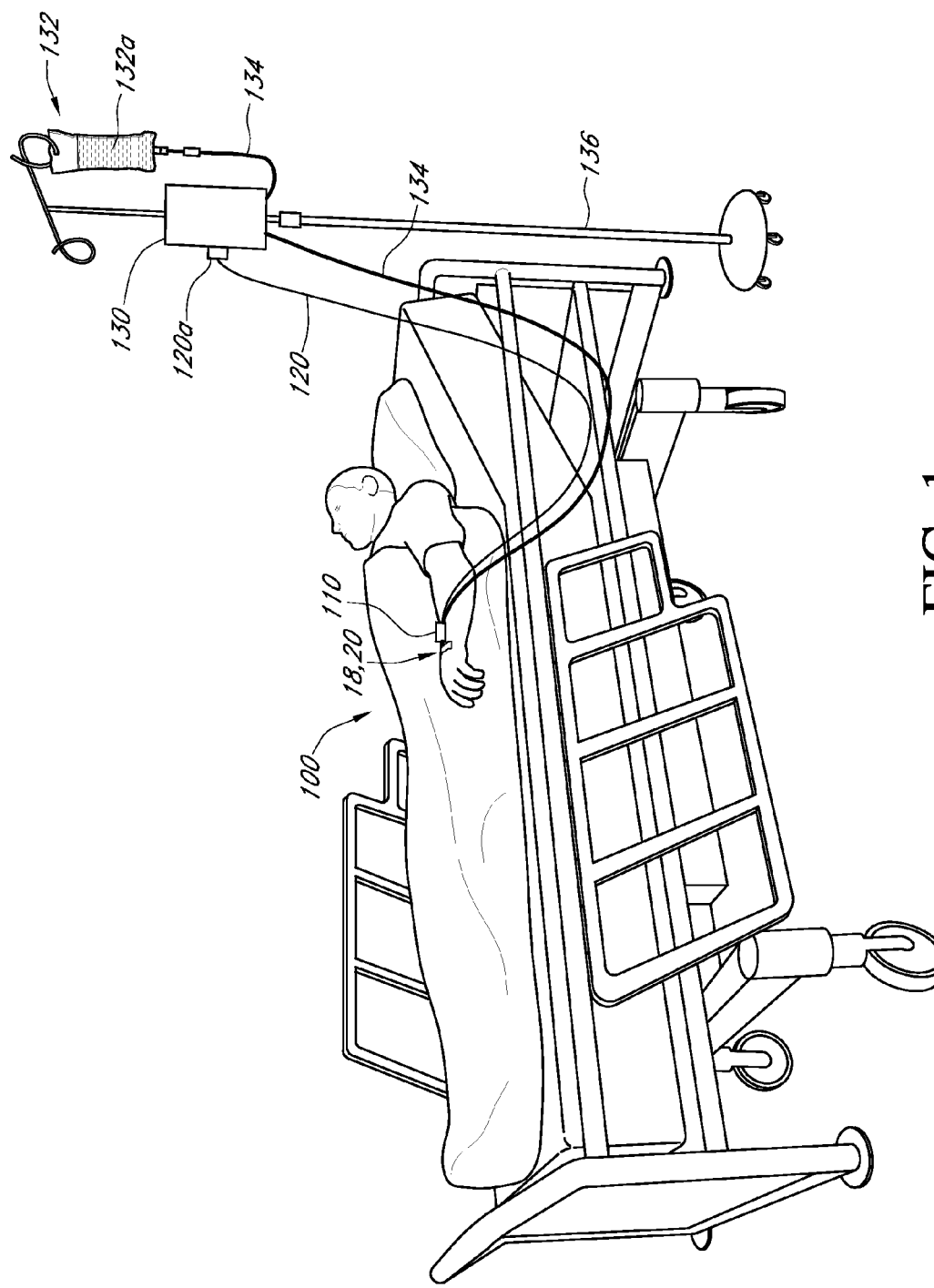
FIG. 1 is diagram illustrating an analyte detection and electronic cable system, in one embodiment.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the preferred embodiments.

Definitions

In order to facilitate an understanding of the preferred embodiments, a number of terms are defined below.

The term "analyte" as used herein is a broad term, and is to be given its ordinary and customary meaning to a person of ordinary skill in the art (and is not to be limited to a special or customized meaning), and refers without limitation to a substance or chemical constituent in a biological sample (e.g., bodily fluids, including, blood, serum, plasma, interstitial fluid, cerebral spinal fluid, lymph fluid, ocular fluid, saliva, oral fluid, urine, excretions, or exudates. Analytes can include naturally occurring substances, artificial substances, metabolites, and/or reaction products. In some embodiments, the analyte for measurement by the sensing regions, devices, and methods albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, metabolic markers, hematocrit and drugs. However, other analytes are contemplated as well, including but not limited to acetaminophen, dopamine, ephedrine, terbutaline, ascorbate, uric acid, oxygen, d-amino acid oxidase, plasma amine oxidase, Xanthine oxidase, NADPH oxidase, alcohol oxidase, alcohol dehydrogenase, Pyruvate dehydrogenase, diols, Ros, NO, bilirubin, cholesterol, triglycerides, gentisic acid, ibuprofen, L-Dopa, Methyl Dopa, salicylates, tetracycline, tolazamide, tolbutamide, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxycholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae, Myoglobin, Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), histamine, Advanced Glycation End Products (AGEs) and 5-hydroxyindoleacetic acid (FHIAA).

The term "biological sample" as used herein is a broad term, and is to be given its ordinary and customary meaning to a person of ordinary skill in the art (and it is not to be limited to a special or customized meaning), and refers without limitation to a sample of a host body, for example, blood, serum, plasma, interstitial fluid, cerebral spinal fluid, lymph fluid, ocular fluid, saliva, oral fluid, urine, sweat, excretions, or exudates, and the like.

The term "blood chemistry analysis device" as used herein is a broad term, and is to be given its ordinary and customary meaning to a person of ordinary skill in the art (and are not to be limited to a special or customized meaning), and refers without limitation to a device that measures a variety of blood components, characteristics or analytes therein. In one embodiment, a blood chemistry analysis device periodically withdraws an aliquot of blood from the host, measures glucose, $O_2$, $CO_2$, $PCO_2$, $PO_2$, potassium, sodium, pH, lactate, urea, bilirubin, creatinine, hematocrit, various minerals, and/ or various metabolites, and the like, and returns the blood to the host's circulatory system. A variety of devices exist for testing various blood properties/analytes at the bedside, such as but not limited to the blood gas and chemistry devices manufactured by Via Medical (Austin, Tex., USA).

The term "calibration" as used herein is a broad term, and is to be given its ordinary and customary meaning to a person of ordinary skill in the art (and is not to be limited to a special or customized meaning), and refers without limitation to the relationship and/or process of determining the relationship between the sensor data and the corresponding reference data. In some embodiments, namely, in continuous analyte sensors, calibration can be updated or recalibrated over time if changes in the relationship between the sensor data and reference data occur, for example, due to changes in sensitivity, baseline, transport, metabolism, and the like.

The term "catheter" as used herein is a broad term, and is to be given its ordinary and customary meaning to a person of ordinary skill in the art (and are not to be limited to a special or customized meaning), and refers without limitation to a tube that can be inserted into a host's body (e.g., cavity, duct or vessel). In some circumstances, catheters allow withdrawal or injection of fluids or access by medical instruments or devices. In some embodiments, a catheter is a thin, flexible tube (e.g., a "soft" catheter). In alternative embodiments, the catheter can be a larger, solid tube (e.g., a "hard" catheter). The term "cannula" is interchangeable with the term "catheter" herein.

The term "continuous (or continual) analyte sensing/sensor" as used herein is a broad term, and is to be given its ordinary and customary meaning to a person of ordinary skill in the art (and is not to be limited to a special or customized meaning), and refers without limitation to a monitoring device and/or monitoring of analyte concentration is continuously, continually, and or intermittently (regularly or irregularly) performed, for example, about every 5 to 10 minutes. It should be understood that continuous analyte sensors generally continually measure the analyte concentration without required user initiation and/or interaction for each measurement, such as described with reference to continuous glucose sensors in U.S. Pat. No. 6,001,067, for example. These terms include situations wherein data gaps can exist (e.g., when a continuous glucose sensor is temporarily not providing data).

The term "count" as used herein is a broad term, and is to be given its ordinary and customary meaning to a person of ordinary skill in the art (and is not to be limited to a special or customized meaning), and refers without limitation to a unit of measurement of a digital signal. For example, a raw data stream or raw data signal measured in counts is directly related to a voltage (for example, converted by an A/D converter), which is directly related to current from the working electrode. In some embodiments, the terms can refer to data that has been integrated or averaged over a time period (e.g., 5 minutes).

The terms "coupling" and "operatively coupling" as used herein are broad terms, and are to be given their ordinary and customary meanings to a person of ordinary skill in the art (and are not to be limited to a special or customized meaning), and refer without limitation to a joining or linking together of two or more things, such as two parts of a device or two devices, such that the things can function together. In one example, two containers can be operatively coupled by tubing, such that fluid can flow from one container to another. Coupling does not imply a physical connection. For example, a transmitter and a receiver can be operatively coupled by radio frequency (RF) transmission/communication.

The term "distal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively far from the reference point than another element.

The term "electrochemically reactive surface" as used herein is a broad term, and is to be given its ordinary and customary meaning to a person of ordinary skill in the art (and is not to be limited to a special or customized meaning), and refers without limitation to a surface where an electrochemical reaction takes place. As a non-limiting example, in an electrochemical glucose sensor, a working electrode measures hydrogen peroxide produced by the enzyme-catalyzed reaction of the analyte detected, which reacts to create an electric current. Glucose analyte can be detected utilizing glucose oxidase, which produces $H_2O_2$ as a byproduct. $H_2O_2$ reacts with the surface of the working electrode, producing two protons ($2H^+$), two electrons ($2e^-$) and one molecule of oxygen ($O_2$), which produces the electronic current being detected.

The terms "electronic connection," "electrical connection," "electrical contact" as used herein are broad terms, and are to be given their ordinary and customary meaning to a person of ordinary skill in the art (and is not to be limited to a special or customized meaning), and refer without limitation to any connection between two electrical conductors known to those in the art. In one embodiment, electrodes are in electrical connection with (e.g., electrically connected to) the electronic circuitry of a device.

The terms "electronics" and "system electronics" as used herein are broad terms, and are to be given their ordinary and customary meaning to a person of ordinary skill in the art (and are not to be limited to a special or customized meaning), and refer without limitation to electronics operatively coupled to the sensor and configured to measure, process, receive, and/or transmit data associated with a sensor, and/or electronics configured to communicate with a flow control device and to control/monitor fluid metering by the flow control device.

The term "ex vivo portion" as used herein is a broad term, and is to be given its ordinary and customary meaning to a person of ordinary skill in the art (and is not to be limited to a special or customized meaning), and refers without limitation to a portion of a device (for example, a sensor) adapted to remain and/or exist outside of a living body of a host.

The term "fluid communication" as used herein is a broad term, and is to be given its ordinary and customary meaning to a person of ordinary skill in the art (and are not to be limited to a special or customized meaning), and refers without limitation to two or more components (e.g., things such as parts of a body or parts of a device) functionally linked such that fluid can move from one component to another. These terms do not imply directionality.

The term "host" as used herein is a broad term, and is to be given its ordinary and customary meaning to a person of ordinary skill in the art (and is not to be limited to a special or customized meaning), and refers without limitation to animals or plants, for example humans.

The term "indwell" as used herein is a broad term, and is to be given its ordinary and customary meaning to a person of ordinary skill in the art (and are not to be limited to a special or customized meaning), and refers without limitation to reside within a host's body. Some medical devices can indwell within a host's body for various lengths of time, depending upon the purpose of the medical device, such as but not limited to a few hours, days, weeks, to months, years, or even the host's entire lifetime. In one exemplary embodiment, an arterial catheter may indwell within the host's artery for a few hours, days, a week, or longer, such as but not limited to the host's perioperative period (e.g., from the time the host is admitted to the hospital to the time he is discharged).

The term "in vivo portion" as used herein is a broad term, and is to be given its ordinary and customary meaning to a person of ordinary skill in the art (and is not to be limited to a special or customized meaning), and refers without limitation to a portion of a device (for example, a sensor) adapted for insertion into and/or existence within a living body of a host.

The term "medical device" as used herein is a broad term, and is to be given its ordinary and customary meaning to a person of ordinary skill in the art (and are not to be limited to a special or customized meaning), and refers without limitation to an instrument, apparatus, implement, machine, contrivance, implant, in vitro reagent, or other similar or related article, including a component part, or accessory which is intended for use in the diagnosis of disease or other conditions, or in the cure, mitigation, treatment, or prevention of disease, in man or other animals, or intended to affect the structure or any function of the body of man or other animals. Medical devices that can be used in conjunction with various embodiments of the analyte sensor system include any monitoring device requiring placement in a human vessel, duct or body cavity, a dialysis machine, a heart-lung bypass machine, blood collection equipment, a blood pressure monitor, an automated blood chemistry analysis device and the like.

The terms "operatively connected," "operatively linked," "operably connected," and "operably linked" as used herein are broad terms, and are to be given their ordinary and customary meaning to a person of ordinary skill in the art (and are not to be limited to a special or customized meaning), and refer without limitation to one or more components linked to one or more other components, such that a function is enabled. The terms can refer to a mechanical connection, an electrical connection, or any connection that allows transmission of signals between the components. For example, one or more electrodes can be used to detect the amount of analyte in a sample and to convert that information into a signal; the signal can then be transmitted to a circuit. In such an example, the electrode is "operably linked" to the electronic circuitry. The terms include wired and wireless connections.

The term "potentiostat" as used herein is a broad term, and is to be given its ordinary and customary meaning to a person of ordinary skill in the art (and is not to be limited to a special or customized meaning), and refers without limitation to an electronic instrument that controls the electrical potential between the working and reference electrodes at one or more preset values. Typically, a potentiostat works to keep the potential constant by noticing changes in the resistance of the system and compensating inversely with a change in the current. As a result, a change to a higher resistance would cause the current to decrease to keep the voltage constant in the system. In some embodiments, a potentiostat forces whatever current is necessary to flow between the working and counter electrodes to keep the desired potential, as long as the needed cell voltage and current do not exceed the compliance limits of the potentiostat.

The terms "processor module," as used herein is a broad term, and is to be given its ordinary and customary meaning to a person of ordinary skill in the art (and are not to be limited to a special or customized meaning), and refers without limitation to a computer system, state machine, processor, components thereof, and the like designed to perform arithmetic or logic operations using logic circuitry that responds to and processes the basic instructions that drive a computer.

The term "proximal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively near to the reference point than another element.

The terms "raw data," "raw data stream", "raw data signal", "data signal", and "data stream" as used herein are broad terms, and are to be given their ordinary and customary meaning to a person of ordinary skill in the art (and are not to be limited to a special or customized meaning), and refer without limitation to an analog or digital signal from the analyte sensor directly related to the measured analyte. For example, the raw data stream is digital data in "counts" converted by an A/D converter from an analog signal (for example, voltage or amps) representative of an analyte concentration. The terms can include a plurality of time spaced data points from a substantially continuous analyte sensor, each of which comprises individual measurements taken at time intervals ranging from fractions of a second up to, for example, 1, 2, or 5 minutes or longer. In some embodiments, the terms can refer to data that has been integrated or averaged over a time period (e.g., 5 minutes).

The term "sensor break-in" as used herein is a broad term, and is to be given its ordinary and customary meaning to a person of ordinary skill in the art (and is not to be limited to a special or customized meaning), and refers without limitation to the time (after implantation) during which the sensor's signal is becoming substantially representative of the analyte (e.g., glucose) concentration (e.g., where the current output from the sensor is stable relative to the glucose level) and/or the completion thereof. The signal may not be 'flat' when the sensor has broken-in, but in general, variation in the signal level at that point is due to a change in the analyte (e.g., glucose) concentration. In some embodiments, sensor break-in occurs prior to obtaining a meaningful calibration of the sensor output. In some embodiments, sensor break-in generally includes both electrochemical break-in and membrane break-in.

The terms "sensor" and "sensor system" as used herein are broad terms, and are to be given their ordinary and customary meaning to a person of ordinary skill in the art (and are not to be limited to a special or customized meaning), and refer without limitation to a device, component, or region of a device by which an analyte can be quantified.

The terms "substantial" and "substantially" as used herein are broad terms, and are to be given their ordinary and customary meaning to a person of ordinary skill in the art (and are not to be limited to a special or customized meaning), and refer without limitation to a sufficient amount that provides a desired function. For example, an amount greater than 50 percent, an amount greater than 60 percent, an amount greater than 70 percent, an amount greater than 80 percent, or an amount greater than 90 percent.

The term "vascular access device" as used herein is a broad term, and is to be given its ordinary and customary meaning to a person of ordinary skill in the art (and are not to be limited to a special or customized meaning), and refers without limitation to any device that is in communication with the vascular system of a host. Vascular access devices include but are not limited to catheters, shunts, blood withdrawal devices, connectors, fluid couplers, valves, tubing and the like.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Integrated System

Figure 2:
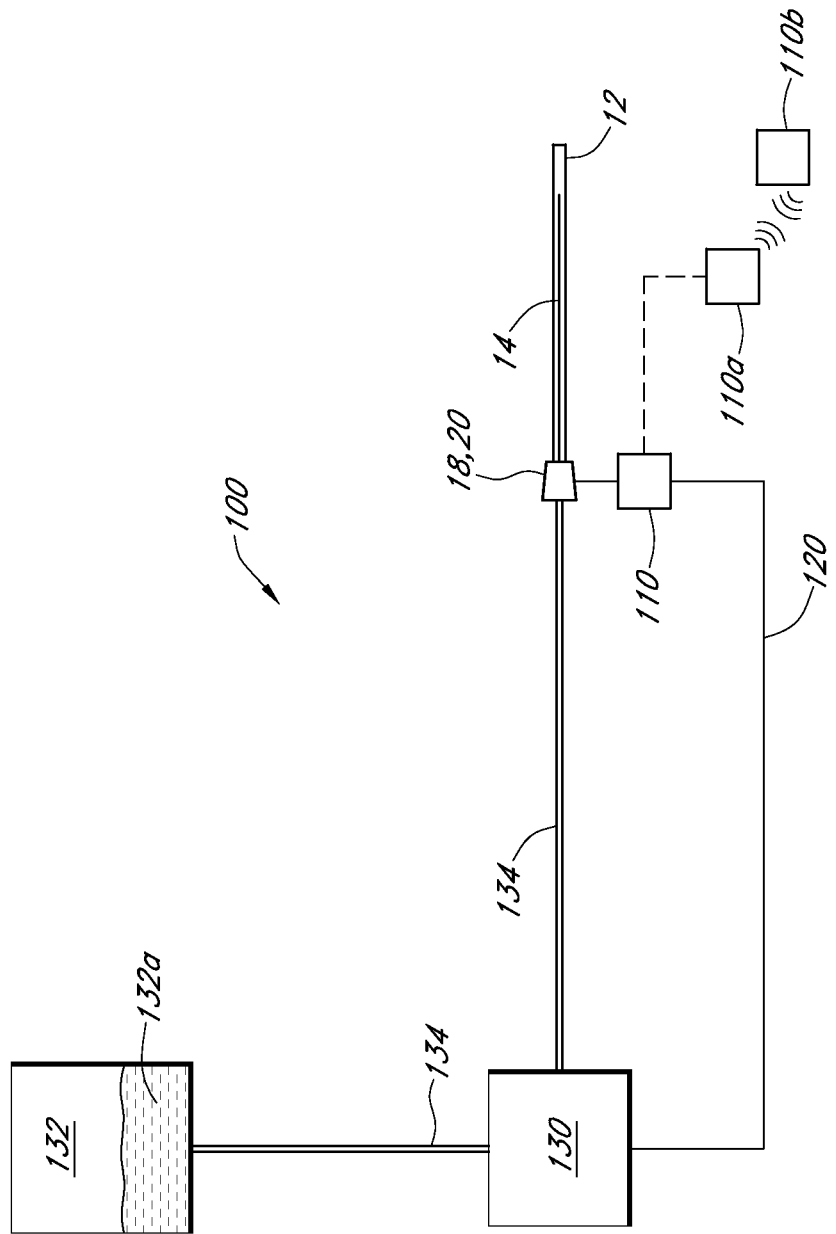
FIG. 2 is a block diagram of the system of FIG. 1.

FIGS. 1-2 illustrate one aspect of the present invention, an integrated system 100 for analyte detection and fluid infusion into a host. The system includes an analyte sensor 14 (see FIG. 2), a vascular access device, such as a catheter 12 and/or a fluid coupler 20 connected to an implanted catheter 12 via the catheter's hub 18, and system electronics 110. In some embodiments, the analyte sensor is as a continuous analyte sensor configured and arranged to generate a signal associated with an analyte in a sample of a circulatory system of a host, as described elsewhere herein. The vascular access device is configured and arranged for fluid communication with the circulatory system of the host. For example, the vascular access device can include a catheter implanted in the host's circulatory system (e.g., a vein or artery), and/or a fluid coupler connected to a catheter implanted in the host's circulatory system. In some embodiments, at least a portion of the analyte sensor is located within the vascular access device. The analyte sensor is associated with the vascular access device such that fluid flowing through the vascular access device passes (e.g., contacts, bathes, flushes and/or washes) the analyte sensor. For example, in some embodiments, the vascular access device is connected to a fluid reservoir 132, such as an IV bag containing an infusion fluid 132a, via tubing 134. The tubing is coupled with a flow control device 130 (e.g., an infusion device), which infuses the fluid into the host and draws back a sample of the host's circulatory system (e.g., such that blood bathes the sensor) responsive to the system electronics. A wide variety of third-party infusion devices, suitable for use with the present system, are available on the market, such as but not limited to devices described in U.S. Pat. No. 4,685,903, U.S. Pat. No. 4,898,578, U.S. Pat. No. 4,925,444, U.S. Pat. No. 5,158,437, U.S. Pat. No. 5,219,279, U.S. Pat. No. 5,207,642, U.S. Pat. No. 5,248,300, U.S. Pat. No. 5,321,392, U.S. Pat. No. 5,496,273, U.S. Pat. No. 5,522,798, U.S. Pat. No. 5,482,446, U.S. Pat. No. 5,547,470, U.S. Pat. No. 5,551,850, U.S. Pat. No. 5,630,710, U.S. Pat. No. 5,681,285, U.S. Pat. No. 5,685,844, U.S. Pat. No. 5,745,378, U.S. Pat. No. 6,231,320, U.S. Pat. No. 6,231,560, U.S. Pat. No. 6,269,340, U.S. Pat. No. 6,544,229, U.S. Pat. No. 6,648,821, U.S. Pat. No. 6,817,990, U.S. Pat. No. 6,692,457, U.S. Pat. No. 6,985,870, U.S. Pat. No. 7,018,361, U.S. Pat. No. 7,109,878, U.S. Pat. No. 7,204,823, U.S. Pat. No. 7,402,153, U.S. Pat. No. 7,417,729, U.S. Patent Publication No. US-2007-0060871-A1, U.S. Patent Publication No. US-2007-0112298-A1, U.S. Patent Publication No. US-2007-0213657-A1, U.S. Patent Publication No. US-2007-0299389-A1, U.S. Patent Publication No. US-2008-0033357-A1, U.S. Patent Publication No. US-2008-0097326-A1, U.S. Patent Publication No. US-2008-0103447-A1, U.S. Patent Publication No. US-2008-0154177-A1, U.S. Patent Publication No. US-2008-0147050-A1, U.S. Patent Publication No. US-2008-0161753-A1, and U.S. Patent Publication No. US-2008-0200897-A1, each of which is incorporated herein by reference in its entirety. The system includes system electronics operably connected to the sensor and configured to process a signal generated by the analyte sensor, wherein the signal is associated with an analyte in the host's circulatory system. Additionally, the system electronics are operably coupled to electronic cable 120, which in turn can be operably coupled to a flow control device such as but not limited to an infusion device. The system electronics are configured and arranged to control fluid metering by the flow control device, such as according to a flow profile described elsewhere herein. In some embodiments, the system can include a local display and/or communications module 110a. In some embodiments, the system can include a remote display 110b, which can be configured to communicate with the system by wired and/or wireless components known in the art.

FIGS. 3A-3B illustrate some exemplary embodiments of the present system for measuring an analyte (e.g., albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker, a drug, etc.) that includes a catheter 12 configured to be inserted or pre-inserted into a host's blood stream. In clinical settings, catheters are often inserted into hosts to allow direct access to the circulatory system without frequent needle insertion (e.g., venipuncture). Suitable catheters can be sized as is known and appreciated by one skilled in the art, such as but not limited to from about 1 French (0.33 mm) or less to about 30 French (10 mm) or more; and can be, for example, 2, 3, 4, 5, 6, 7, 8, 9, 10, 11, 12, 13, 14, 15, 16, 17, 18, 19, or 20 French (3 French is equivalent to about 1 mm) and/or from about 33 gauge or less to about 16 gauge or more, for example, 33, 32, 31, 30, 29, 28, 27, 26, 25, 24, 23, 22, 21, 20, 19, 18, 17, or 16 gauge. Additionally, the catheter can be shorter or longer, for example 0.75, 1.0, 1.25, 1.5, 1.75, 2.0 inches in length or longer. In some embodiments, the catheter is sized for insertion into a pediatric host, such as a neonatal host (e.g., a 22-24 gauge catheter or smaller). In some embodiments, the catheter is a venous catheter. In other embodiments, the catheter is configured for insertion into a peripheral or a central artery. In some embodiments, the catheter is configured to extend from a peripheral artery to a central portion of the host's circulatory system, such as but not limited to the heart. The catheter can be manufactured of any medical grade material known in the art, such as but not limited to polymers and glass as described herein. A catheter can include a single lumen or multiple lumens. A catheter can include one or more perforations, to allow the passage of host fluid through the lumen of the catheter.

The terms "inserted" or "pre-inserted" as used herein are broad terms, and are to be given their ordinary and customary meaning to a person of ordinary skill in the art (and are not to be limited to a special or customized meaning), and refer without limitation to insertion of one thing into another thing. For example, a catheter can be inserted into a host's blood stream. In some embodiments, a catheter is "pre-inserted," meaning inserted before another action is taken (e.g., insertion of a catheter into a host's blood stream prior to insertion of a sensor into the catheter). In some exemplary embodiments, a sensor is coupled to a pre-inserted catheter, namely, one that has been previously inserted (or pre-inserted) into the host's circulatory system. Alternatively, the sensor and the catheter can be configured to be inserted together and/or the sensor can be integrally formed with the catheter.

Referring now to FIG. 3A-3B, in some embodiments, the catheter 12 includes an in vivo portion, such as is a thin, flexible tube having a lumen, such as is known in the art, and an ex vivo portion. In some embodiments, the in vivo portion of the catheter can be rigid; in other embodiments, the catheter can be custom manufactured to desired specifications (e.g., rigidity, dimensions, etc). The catheter can be a single-lumen catheter or a multi-lumen catheter. At the catheter's proximal end is a small orifice 12b for fluid communication of the catheter with the blood stream. At the catheter's distal end (e.g., ex vivo portion) is a connector or hub 18, such as a leur connector or other fluid connector known in the art.

The illustrations of FIGS. 3A-3B show one exemplary embodiment of the catheter's connector 18 including a flange 18a and a duct 18b (also referred to as a lumen). In the exemplary embodiment, the flange is configured to enable connection of the catheter to other medical equipment (e.g., saline bag, pressure transducer, blood chemistry device, and/or the like) or capping (e.g., with a bung and/or the like). Although one exemplary connector is shown, one skilled in the art appreciates a variety of standard or custom made connectors suitable for use with the preferred embodiments. The duct is in fluid communication with the catheter lumen and terminates in a connector orifice 18c.

In some embodiments, the catheter is inserted into the host's blood stream, such as into a vein or artery by any useful method known in the art. Generally, prior to and during insertion, the catheter is supported by a hollow needle or trochar (not shown). For example, the supported catheter can be inserted into a peripheral vein or artery, such as in the host's arm, leg, hand, or foot. Typically, the supporting needle is removed (e.g., pulled out of the connector) and the catheter is connected (e.g., via the connector 18) to IV tubing and a saline drip, for example. However, in one embodiment, the catheter is configured to operatively couple to medical equipment, such as but not limited to a sensor system of the preferred embodiments. Additionally and/or alternatively, the catheter can be configured to operatively couple to another medical device, such as a pressure transducer, for measurement of the host's blood pressure. For example, Utah Medical Products Inc. (Midvale, Utah, USA) produces a variety of DELTRAN® Brand disposable blood pressure transducers that are suitable for use with various embodiments disclosed herein.

In some embodiments, the catheter 12 (and optionally the analyte sensor 14) is configured to indwell within the host's blood stream in vivo. An indwelling catheter is typically inserted within a host's vein or artery for a period of time, often 2, 3 or more days, a week, or even longer. In some embodiments, the catheter can indwell in a host's artery or vein for the length of a perioperative period (e.g., the entire hospital stay) or for shorter or longer periods. In some embodiments, the use of an indwelling catheter permits continuous access of an analyte sensor to a blood stream while simultaneously allowing continuous access to the host's blood stream for other purposes, for example, the administration of therapeutics (e.g., fluids, drugs, etc.), measurement of physiologic properties (e.g., blood pressure), fluid removal, and the like.

Referring again to FIGS. 3A-3B, the system 10 also includes an analyte sensor 14 configured to extend into the catheter lumen. In some embodiments, the sensor is configured to reside within the lumen, such as but not limited to just inside the catheter tip (e.g., adjacent to orifice 12b), anywhere within the lumen and/or within the hub connector. The sensor can extend through the catheter in any functional manner. In some embodiments, the sensor is configured to be held (e.g., disposed) on an inner surface (e.g., the lumen) or outer surface of the catheter. In some embodiments, the sensor is deposited (e.g., formed) on a surface of the catheter. In some embodiments, a sensor is attached to a surface of the catheter, such as by an adhesive and/or welding. In some other embodiments, the sensor is configured to "free float" within the lumen of the catheter. In other embodiments, the analyte sensor is configured to extend out of the catheter orifice and into the host's blood stream by about 0.010 inches to about 1 inch, or shorter or longer lengths. In still other embodiments, the analyte sensor is configured to reside within the fluid coupler 20, such as described in co-pending U.S. patent application Ser. No. 12/267,542, filed on even date herewith and entitled "Analyte Sensor," U.S. patent application Ser. No. 12/055,114 filed Mar. 25, 3008 and entitled "Analyte Sensor," U.S. Patent Publication No. US-2008-0119703-A1, and U.S. Patent Publication No. US-2008-0108942-A1, each of which is incorporated herein by reference in its entirety. In some embodiments, the sensor is configured to measure the concentration of an analyte within the host's blood stream, as described in greater detail elsewhere herein.

In preferred embodiments, the sample is drawn back a distance from its source (e.g., the catheter orifice 12b), such that the sensor's electrodes (e.g., electroactive surfaces) are bathed in the drawn back sample. Since the catheter is a three-dimensional object, the distance of sample draw-back corresponds with a sample volume, depending upon the location of the sensor's electrodes (e.g., a point within the catheter's in vivo portion, within the catheter's ex vivo portion, or within the fluid coupler), the catheter's size, the interior volume of the catheter's hub and/or of the fluid coupler, and the like. It is know that it can be detrimental to the health of some hosts, such as but not limited to neonatal hosts, to loose even small amounts of blood. Accordingly, in preferred embodiments, the vascular access device (e.g., the catheter and/or the fluid coupler) and the analyte sensor are configured and arranged to minimize the amount of sample required (e.g., distance and/or volume) to bath the electroactive surface(s) of the analyte sensor in the sample. For example, in some embodiments, the system is configured such that a sample is drawn back no more than about 100, 90, 80, 70, 65, 60, 55, 50, 45, 40, 35, 30, or 25-mm or less. In some embodiments, the system is configured such that a sample drawn back has a volume of no more than about 400, 350, 300, 275, 250, 225, 175, 150, 125, 90, 80, 70, 60, 50, 40, 30, 20, 15, 10, 5, 4, 3, 2, or 1-μl or less. Some exemplary embodiments are described below.

In one exemplary embodiment, the catheter is a peripheral catheter (e.g., for insertion into a vein located in an arm and/or leg) having the analyte sensor located within the catheter hub. In preferred embodiments, the volume that the catheter hub can hold has been restricted, such as by fabricating the catheter hub with a reduced internal diameter. In this embodiment, the sample is drawn back no more than about 50, 45, 40 or 35-mm or less (e.g., into the catheter hub, depending upon the length of the catheter), such that the analyte sensor is bathed in the sample.

In another exemplary embodiment, the analyte sensor is incorporated in a fluid coupler configured and arranged to be fluidly coupled to the hub of an implanted peripheral catheter (e.g., such as in FIGS. 3A-3B), wherein the sensor extends into the lumen of the catheter. In this embodiment, since the sensor's electroactive surfaces are located within the catheter's lumen, the sample is drawn back less than 40-mm. For example, if the sensor is configured such that the electrodes extend adjacent to the catheter tip (e.g., when inserted into the catheter lumen), then the sample can be drawn back only a few millimeters (e.g., 1, 2, 3, 4 or 5-mm) into the catheter's lumen (e.g., such that the electroactive surfaces are bathed in the drawn-back sample). In another example, if the electrodes extend only part way into the catheter's lumen, then the sample can be drawn back from about 6, 7, 8, 9, 10, 11, 12, 13, 14 or 15-mm or less to about 20, 21, 22, 23, 24, 25, 26, 27, 28, 29 or 30-mm or more. In yet another example, if the electrodes extend only slightly into the catheter, such that the sample is drawn back no more than about 31, 32, 33, 34 or 35-mm. Accordingly, depending upon the distance the sample is drawn back, only very small samples (e.g., such as from no more than about 250, 200, 100, 95, 90, 85, 80, 75, 70, 65, 60, 55, 50, 45, 40, 35, 30, 25, 20, 15-µl to no more than about 10, 9, 8, 7, 6, 5, 4, 3, 2, 1, 0.5-µl or even less) are drawn back/used.

In yet another exemplary embodiment, the analyte sensor is located within the lumen of a fluid coupler (e.g., configured for fluid connection with a catheter). In this embodiment, when the fluid coupler is coupled to an implanted peripheral catheter, the sensor's electrodes are bathed in a sample when the sample is drawn back a distance of no more than about 50, 45, 40, 35 or 30-mm, depending upon the length of the catheter, which correlates with a sample volume of no more than about 1000, 950, 900, 850, 800, 750, 700, 650, 600, 550, 500, 450, 400, 350, 300 or 250-µl or less. Alternatively, when the fluid coupler is coupled to a central catheter (e.g., a catheter for insertion into vessels in the body, such as to access the heart), the distance the sample is drawn back (e.g., to sufficiently contact/bathe the electrodes such that analyte measurements can be taken) is much farther (e.g., relative to the distance of draw-back into a peripheral catheter), since central catheters range from about 12 to 24-inches in length. Thus, in this exemplary embodiment, the distance the sample is drawn back includes the entire length of the central catheter (including the catheter's hub) and a portion of the connector, such as but not limited to up to about 12, 13, 14 or 15 inches, to about 18, 19, 20, 21, 22, 23, 24 or 25-inches or more, depending upon the length of the catheter, which can correspond with a sample volume of up to about 1-ml, however, more or less volume can be used. If the sensor extends from the fluid coupler into the central catheter, the distance is reduced to a portion of the central catheter's length, with a corresponding reduction in sample volume.

In some embodiments, the system is configured and arranged such that the sensor (e.g., the electroactive surfaces) is located within about 55, 50, 45, 40, 35, 30, 25, 20, 15, 10, 9, 8, 7, 6, 5, 4, 3, 2, or 1-mm from the sample prior to draw-back of the sample (e.g., the sample is drawn back about 5, 50, 45, 40, 35, 30, 25, 20, 15, 10, 9, 8, 7, 6, 5, 4, 3, 2, or 1-mm, such that the electroactive surfaces are bathed in the drawn-back sample). In some embodiments, the system is configured an arranged such that the analyte sensor is bathed in sample when about 1000, 950, 900, 850, 800, 750, 700, 650, 600, 550, 500, 450, 400, 375, 350, 325, 300-µl or less of sample is drawn back (e.g., when the vascular access device is in fluid communication with the circulatory system of the host). In some embodiments, the system is configured and arranged such that the analyte sensor is bathed in sample when about 275, 250, 225, 200, 175, 150, 125, 100, 75, 50, 40, 30, 20, 10, or 5-µl or less of sample is drawn back. In some embodiments, the sample is returned to the host, such as by infusing a volume of the infusion fluid, which washes the sample back into the host (e.g., re-infuses the sample), as described elsewhere herein. Accordingly, in some embodiments, there is substantially no blood loss to the host.

Referring to FIGS. 3A-3B, the sensor has a proximal end 14*a* and a distal end 14*b*. At its distal end, the sensor 14 is associated with (e.g., connected to, held by, extends through, and the like) a fluid coupler 20 having first and second sides (20*a* and 20*b*, respectively). The fluid coupler is configured to releasably mate (via its first side) to the catheter connector 18. For example, in one embodiment, a skirt 20*c* is located at the fluid coupler's first side and includes screw threads configured to releasably mate with the connector flange 18*a*, which is screwed into the fluid coupler via the screw threads. However, in other embodiments, the fluid coupler is configured to mate with the connector using any known mating configuration, for example, a snap-fit, a press-fit, an interference-fit, and the like, and can include a locking mechanism to prevent separation of the connector and fluid coupler. The fluid coupler includes a lumen (not shown) extending from a first orifice 20*h* on its first side to a second orifice 20*i* located on the fluid coupler's second side 20*b*. When the catheter connector is mated with the fluid coupler, the catheter's lumen is in fluid communication with the fluid coupler's lumen 20*f* via orifices 18*c* and 20*h*. In some embodiments, the vascular access device includes a fluid coupler having a first end (e.g., side) configured and arranged for fluid communication with a catheter configured for implantation in a host's circulatory system and a second end (e.g., side) configured and arranged for fluid communication with tubing associated with a flow control device.

FIGS. 3A-3B show one embodiment of a fluid coupler 20, however, any known coupler configuration can be used, including but not limited to a straight coupler, a Y-coupler, a T-coupler, a cross-coupler, a custom configured coupler, and the like. In some embodiments, the fluid coupler includes at least one valve (e.g., a septum, a 3-way valve, a stop-cock valve), which can be used for a variety of purposes (e.g., injection of drugs). The fluid coupler can be made of any convenient material, such as but not limited to plastic, glass, metal or combinations thereof and can be configured to withstand known sterilization techniques.

In the exemplary embodiment, the second side 20*b* of the fluid coupler 20 is configured to be operably connected to IV equipment, another medical device or to be capped, and can use any known mating configuration, for example, a snap-fit, a press-fit, an interference-fit, and the like. In one exemplary embodiment, the second side is configured to mate with a saline drip, for delivery of saline to the host. For example, the saline flows from an elevated bag 132 of sterile saline 132*a* via tubing 134, through the fluid coupler, through the catheter 12 and into the host's blood system (e.g., vein or artery). In some embodiments, a syringe can be mated to the fluid coupler, for example, to withdraw blood from the host, via the catheter. Additional connection devices (e.g., a three-way valve) can be operably connected to the fluid coupler, to support additional functionality and connection of various devices, such as but not limited to a blood pressure transducer.

Figure 3C:
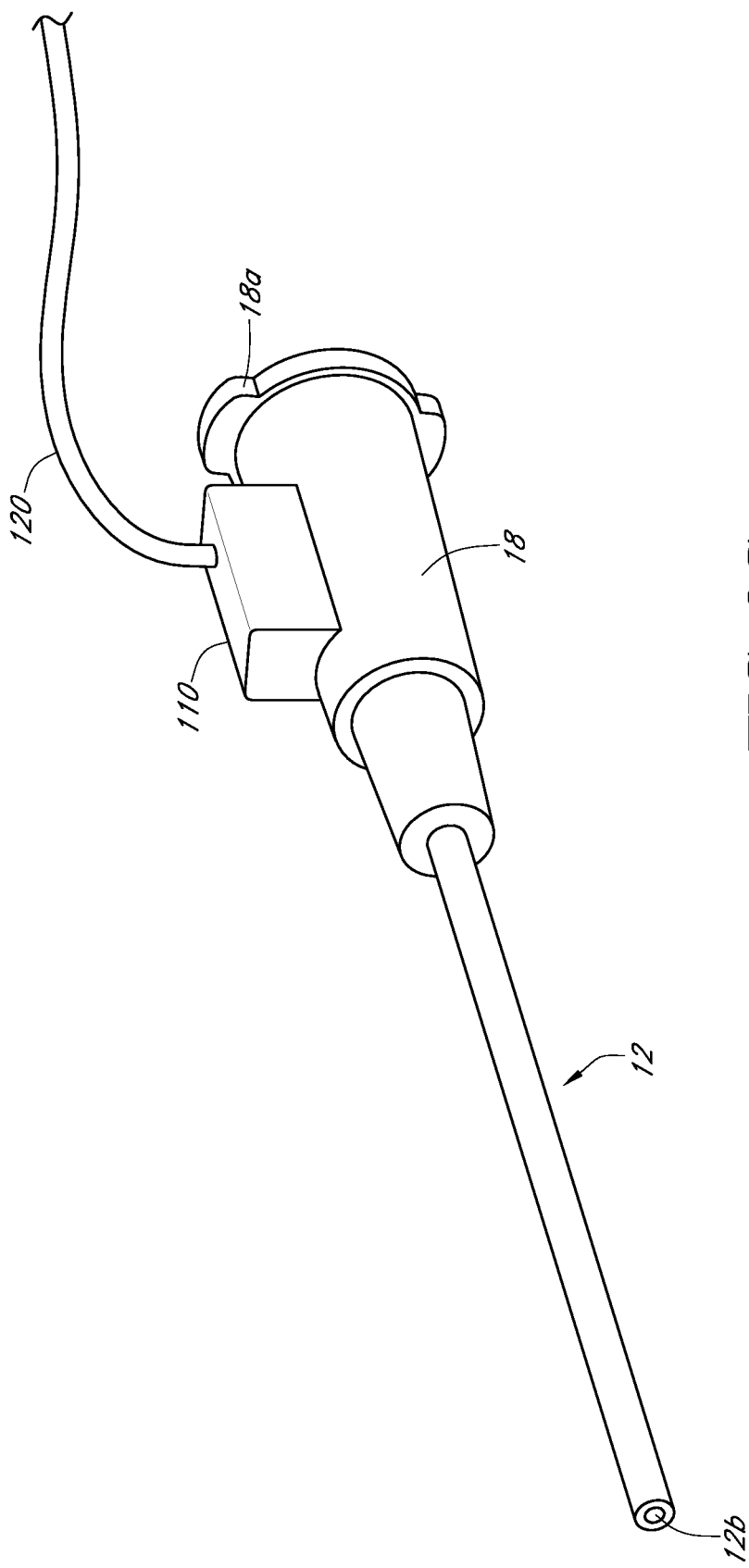
FIG. 3C is a perspective view of an analyte detection and electronic cable system, in yet another embodiment.

Referring to the exemplary embodiments of FIGS. 3A-3B, at least a portion of the sensor 14 passes through the fluid coupler 20 (e.g., the fluid coupler lumen) and is operatively connected to the system electronics 110. In some embodiments, such as that shown in FIG. 3A, the system electronics can be disposed wholly with the fluid coupler (e.g., integrally with or connected to). In another embodiment, such as that shown in FIG. 3C, the sensor is disposed within the catheter and some or all of the system electronics are disposed on the catheter's hub 18. In some embodiments, the system electronics can be coupled with an electronic cable 120, such as via a pair of male and female electronic connectors, or other means known in the art, for example. In other embodiments, such at that shown in FIG. 3B, the system electronics can be disposed on the cable, wherein the cable is coupled to the analyte sensor via an electronic connection in the fluid coupler. In embodiments wherein the system electronics are disposed on (e.g., physically connected to) the cable, the electronics can be disposed on the cable at any point along its length, from adjacent to the fluid coupler to adjacent to the cable's plug 120a, which is configured and arranged for functionally connecting the system electronics (e.g., via the cable) to a flow control device (not shown). In another exemplary embodiment, a portion of the system electronics, such as a potentiostat, is disposed on the fluid coupler and the remaining electronics (e.g., electronics for receiving, data processing, controlling the flow control device, etc.) are disposed elsewhere on the cable. In another exemplary embodiment, all of the system electronics can be disposed on the fluid coupler.

In some embodiment, the system electronics are located on (e.g., physically connected to) the cable, such as within about three feet or less of the analyte sensor. For example, the system electronics can be attached, such as via a clip or hook and loop tape, to the host's shirt/hospital gown. In another embodiment, the system electronics are physically connected to the cable such that the system electronics are located within about 6-feet or less from the sensor, on the cable. For example, the system electronics can be attached to the head of the bed or placed on the bedside. In yet another embodiment, the system electronics are physically connected to the cable such that the system electronics are located within about 8-feet or less from the sensor, on the cable. In other embodiments, the system electronics can be located anywhere on the cable, regardless of the cable's length. For example, if the cable is a 12-foot cable, the system electronics can be located within about 12-feet or less of the sensor. In other embodiments, the system electronics are located within about 12, 10, 8, 6, 5, 4, 3, 2 or 1-feet or less of the analyte sensor, such as on the cable.

In some embodiments, the fluid coupler and at least a portion of the system electronics are configured and arranged to releasably mate (e.g., functionally connect by "plugging in" the electronics to the fluid coupler, such that the electronics are functionally connected to the analyte sensor). Embodiments in which the fluid coupler (and therefore the analyte sensor) and the system electronics are configured and arranged to functionally connect (e.g., releasably) with each other are advantageous as they enable (1) sterilization of the fluid coupler/analyte sensor separate from the system electronics and cable, as well as (2) reuse of the system electronics and cable. However, embodiments in which at least a portion of the system electronics is integrally incorporated into the fluid coupler are preferred in some circumstances. For example, a portion of the system electronics configured to power the analyte sensor (e.g., a potentiostat and/or battery) can be incorporated wholly into the fluid coupler, while the remaining portion of the system electronics are incorporated into the cable.

The electronic cable 120 includes a connector 120a configured and arranged to operably connect the cable with a flow control device, such as but not limited to an infusion device, such as a pump. The connector can be any type of connector known in the art, such as a serial connector, a parallel connector, or the like. In some embodiments, the connector is configured for wireless communication between the cable and the flow control device, such as but not limited to via various forms of radio frequency (RF) telemetry, infrared transmissions, optical transmission, sonic and ultrasonic transmissions, Bluetooth, and/or the like. In some embodiments, the system is configured and arranged to be powered, either wholly or in part, by the flow control device. For example, in one embodiment, the cable and connector are configured and arranged to draw power from the flow control device. In one embodiment, the connector includes a first connector (e.g., a data-transfer/communication connector) for electronic communication between the electronic cable and the flow control device, and a second connector (e.g., a "plug" configured to releasably mate with an electrical "socket") for receipt of power from the flow control device. In some embodiments, the system can include a battery, such as a battery integrated into the fluid coupler 20 (or elsewhere in the system electronics or on the cable), such as to maintain a bias on the analyte sensor 14 if the host is temporarily disconnected from the fluid infusion device, such as for a medical procedure, for example.

Referring again to FIGS. 3A-3B, a protective sheath 26 is configured to cover at least a portion of the sensor 14 during insertion, and includes hub 28 and slot 30. In general, the protective sheath protects and supports the sensor prior to and during insertion into the catheter 12 via the connector 18. The protective sheath can be made of biocompatible polymers known in the art, such as but not limited to polyethylene (PE), polyurethane (PE), polyvinyl chloride (PVC), polycarbonate (PC), nylon, polyamides, polyimide, polytetrafluoroethylene (PTFE), Teflon, nylon and the like. The protective sheath includes a hub 28, for grasping the sheath (e.g., while maintaining sterilization of the sheath). In this embodiment, the hub additionally provides for mating with the second side 20b of the fluid coupler 20, prior to and during sensor insertion into the catheter. In this exemplary embodiment, the slot of the protective sheath is configured to facilitate release of the sensor therefrom. In this embodiment, after the sensor has been inserted into the catheter, the hub is grasped and pulled from the second side of the fluid coupler. This action peels the protective sheath from the sensor (e.g., the sensor slides through the slot as the sheath is removed), leaving the sensor within the catheter. The second side of the fluid coupler can be connected to other medical devices (e.g., a blood pressure monitor) or an IV drip (e.g., a saline drip), or capped. In alternative embodiments, the sheath can fold (e.g., fold back or concertinas) or retract (e.g., telescope) during insertion, to expose the sensor. In other embodiments, the sheath can be configured to tear away from the sensor before, during, or after insertion of the sensor. In still other embodiments, the sheath can include an outlet hole, to allow protrusion of the sensor from the back end of the sheath (e.g., near the hub 28). One skilled in the art will recognize that additional configurations can be used, to separate the sensor from the sheath. In some embodiments, the sheath can be optional, depending upon the sensor design. For example, the sensor can be inserted into a catheter or other vascular access device with or without the use of a protective sheath). In some embodiments, the sensor can be disposed on the outer surface of a catheter (as described elsewhere herein) or on the inner surface of a catheter; and no sheath is provided. In other embodiments, a multi-lumen catheter can be provided with a sensor already disposed within one of the lumens; wherein the catheter is inserted into the host's vein or artery with the sensor already disposed in one of the lumens.

FIG. 3C illustrates an exemplary embodiment, in which the analyte sensor integrally formed within the catheter. In this embodiment, the catheter 12 is configured for insertion into a host's blood stream (e.g., via a vein or artery) and an analyte sensor (not shown) can be formed within the catheter, such as within the hub 18 and/or on a surface of the catheter's lumen, for example such that the sensor's electroactive surfaces are located adjacent to the catheter's orifice 12b. The catheter's ex vivo end includes a connector 18 (e.g., a hub) configured and arranged to be operatively connected to an IV system (e.g., saline bag and tubing) wherein the tubing is threaded through a flow control device configured and arranged to meter the flow of fluids, other medical devices (e.g., automatic blood chemistry machine, dialysis machine, a blood bag for collecting donated blood, etc.), or capped, such as via flange 18a. In the embodiment shown in FIG. 3C, the catheter's connector/hub 18 includes at least a portion of the system electronics 110. The system electronics are configured to control the analyte sensor (e.g., to measure and/or process the sensor data) and the flow control device (regulate the metering fluid infusion and sample draw-back) as described in more detail elsewhere herein. An electronic cable 120 is operably coupled to the system electronics and is configured and arranged to operably connect with a flow control device, such as but not limited to a third-party infusion device described elsewhere herein. In some embodiments, the system electronics can be partially or wholly disposed with (e.g., integral with, disposed on, or proximal to) the connector at the distal end of the catheter or partially or wholly disposed on the electronic cable 120. In one embodiment, the electronics disposed with the connector include a potentiostat. In some embodiments, the electronics are configured to measure the host's analyte concentration substantially continuously. For example, the sensor can measure the analyte concentration continuously or at time intervals ranging from fractions of a second up to, for example, 1, 2, or 5 minutes or longer.

Continuous Analyte Sensors

In preferred embodiments, the analyte sensor 14 is a small-structured sensor with at least one electrode, such as a working electrode, as described elsewhere herein. In some embodiments, the sensor has two or more electrodes, such as but not limited to working, reference and/or counter electrodes. In some embodiments, the sensor includes a reference electrode disposed remotely from the working electrode, as discussed elsewhere herein. In some embodiments, the sensor includes two or more electrodes that are separated by an insulator, such as described in U.S. Patent Publication No. US-2007-0027385-A1, herein incorporated by reference in its entirety. In preferred embodiments, the electrode is a fine wire, such as but not limited to a wire formed from platinum, iridium, platinum-iridium, palladium, gold, silver, silver chloride, carbon, graphite, gold, conductive polymers, alloys and the like. In some exemplary embodiments, the sensor includes one or more electrodes formed from a fine wire with a diameter of from about 0.001 or less to about 0.010 inches or more. Although the electrodes can by formed by a variety of manufacturing techniques (bulk metal processing, deposition of metal onto a substrate, and the like), it can be advantageous to form the electrodes from plated wire (e.g. platinum on steel wire) or bulk metal (e.g. platinum wire). It is believed that electrodes formed from bulk metal wire provide superior performance (e.g. in contrast to deposited electrodes), including increased stability of assay, simplified manufacturability, resistance to contamination (e.g., which can be introduced in deposition processes), and improved surface reaction (e.g., due to purity of material) without peeling or delamination.

In some embodiments, one or more electrodes are disposed on a support, such as but not limited to a planar support of glass, polyimide, polyester and the like. In some exemplary embodiments, the electrodes include conductive inks and/or pastes including gold, platinum, palladium, chromium, copper, aluminum, pyrrolitic carbon, composite material (e.g., metal-polymer blend), nickel, zinc, titanium, or an alloy, such as cobalt-nickel-chromium, or titanium-aluminum-vanadium, and are applied to the support using known techniques, such as but not limited to screen-printing and plating. Additional description can be found in U.S. Pat. No. 7,153,265, U.S. Patent Publication No. US-2006-0293576-A1, U.S. Patent Publication No. US-2006-0253085-A1, U.S. Pat. No. 7,003,340, and U.S. Pat. No. 6,261,440, each of which is incorporated in its entirety by reference herein.

In some embodiments, an optional redundant sensor can be disposed within the catheter lumen, the catheter hub 18 and/or the fluid connector 20, in addition to the sensor 14 described elsewhere herein. In one exemplary embodiment, a sensor and a redundant sensor are disposed within the lumen of a sensor implanted in a host's peripheral vein, such that the electroactive surfaces of the sensor are more proximal to the catheter orifice 12b than the electroactive surfaces of the redundant sensor; wherein blood is taken up into the lumen such that the electroactive surfaces of both the sensor and the redundant sensor are contact by the blood; such that analyte can be detected by both the sensor and the redundant sensor and the redundant sensor measurements are used by the system to confirm the sensor's measurements. In a further embodiment, both the sensor and the redundant sensor are intermittently concurrently contacted by the solution 132a such that both the sensor and the redundant sensor can take calibration measurements of the solution, wherein the calibration measurements of the redundant sensor are at least used to confirm the calibration measurements of the sensor (e.g., a quality check). In another embodiment, the calibration measurements from both the sensor and the redundant sensor are used to calibrate the sensor.

The system includes a continuous analyte sensor 14 that measures a concentration of an analyte of interest or a substance indicative of the concentration or presence of the analyte. For example, in some embodiments, the analyte sensor is configured and arranged to generate a signal a signal associated with at least 1, 2, 3, 4, 5, 6, 7, 8, 12, 15 or more of albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein and uric acid in the sample. In some embodiments, the analyte sensor is configured and arranged to continuously measure glucose in a host. In some embodiments, the analyte sensor can be configured to analyze a plurality of intermittent biological samples such as a series of samples drawn back by the flow control device, responsive to control by the system electronics 110, such as according to a flow profile. The analyte sensor can be configured to use any method of analyte-measurement known in the art, including enzymatic, chemical, physical, electrochemical, spectrophotometric, polarimetric, calorimetric, radiometric, and the like.

Figure 4B:
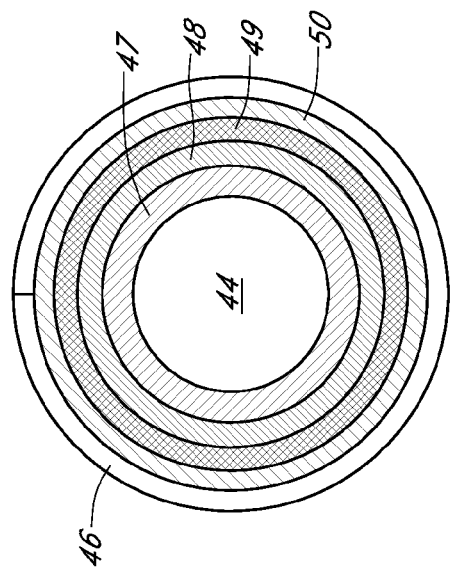
FIG. 4B is a cross-section of the analyte sensor of FIG. 4A, taken on line 4B-4B.
Figure 4A:
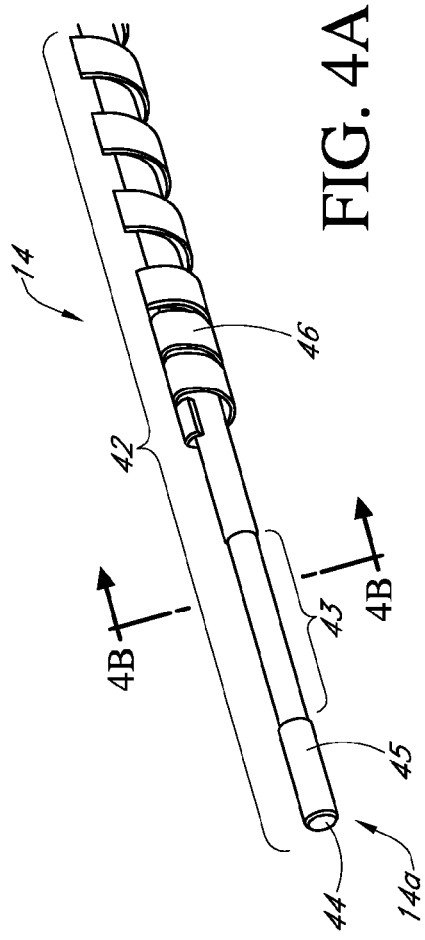
FIG. 4A is a perspective view of an in vivo portion of a continuous analyte sensor, in one embodiment.

FIG. 4A is a perspective view of the in vivo portion 42 of an analyte sensor 14 that can be used in some embodiments, as a non-limiting example. FIG. 4B is a cross-section of the analyte sensor of FIG. 4A, taken on line 4B-4B. In some embodiments, the continuous electrochemical analyte sensor includes at least one working electrode 44 and at least one reference electrode 46. In some embodiments, the sensor includes at least two working electrodes, which can be twisted and/or bundled, such as in a helical and/or coaxial configuration. A working electrode includes an insulator 45, a portion of which is removed to expose the electroactive surface 43. Referring to FIG. 4B, a membrane can be disposed on the analyte sensor, in some embodiments. In some embodiments, the membrane can include one or more layers, which are configured and arranged to optimize analyte detection. For example, a membrane can include an electrode layer 47, for example, to enable diffusional electron transfer at the electrode surface, an enzyme layer 48, for example to catalyze the analyte, an interferent layer 49, to reduce diffusion of one or more interfering substances to the electrode or into the enzyme layer, a resistance layer 50, for example to control the amount of an analyte and/or co-reactant. For example, in some embodiments of a continuous glucose sensor, a membrane (or membrane layer or membrane domain) including a glucose oxidase (GOX) enzyme domain is deposited on the working electrode (e.g., the electroactive surface), such that the analyte sensor can detect glucose. In a further example, in some embodiments of a continuous glucose sensor, an interferent domain is included to restrict the diffusion of acetaminophen, an interferent, to the sensor's electroactive surfaces. In some embodiments, the analyte sensor is configured to be inserted into and to extend within a vascular access device, such as a catheter 12 or cannula implanted in a host's vein or artery. In some embodiments, the sensor is configured to reside within the catheter lumen; while in other embodiments, the sensor is configured to protrude from the catheter's orifice 12b. In still other embodiments, the analyte sensor is disposed (wholly or in part) within either the catheter's connector 18 or within the lumen of the fluid coupler 20.

As a non-limiting example, in some embodiments, the analyte sensor 100 is a continuous electrochemical analyte sensor configured to provide at least one working electrode and at least one reference electrode, which are configured to measure a signal associated with a concentration of the analyte in the host, such as described in more detail below. The output signal is typically a raw data stream that is used to provide a useful value of the measured analyte concentration in a host to the patient or doctor, for example. However, the analyte sensors of some embodiments comprise at least one additional working electrode configured to measure at least one additional signal, as discussed elsewhere herein. For example, in some embodiments, the additional signal is associated with the baseline and/or sensitivity of the analyte sensor, thereby enabling monitoring of baseline and/or sensitivity changes that may occur over time.

In general, electrochemical continuous analyte sensors define a relationship between sensor-generated measurements (for example, current in pA, nA, or digital counts after A/D conversion) and a reference measurement (for example, glucose concentration mg/dL or mmol/L) that are meaningful to a user (for example, patient or doctor). For example, in the case of an implantable diffusion-based glucose oxidase electrochemical glucose sensor, the sensing mechanism generally depends on phenomena that are linear with glucose concentration, for example: (1) diffusion of glucose through a membrane system (for example, biointerface membrane and membrane system) situated between implantation site and/or the electrode surface, (2) an enzymatic reaction within the membrane system, and (3) diffusion of the $H_2O_2$ to the sensor. Because of this linearity, calibration of the sensor can be understood by solving an equation:

$$y=mx+b$$

wherein y represents the sensor signal (e.g., counts), x represents the estimated glucose concentration (e.g., mg/dL), m represents the sensor sensitivity to glucose (e.g., counts/mg/dL), and b represents the baseline signal (e.g., counts). When both sensitivity m and baseline (background) b change over time in vivo, calibration has generally requires at least two independent, matched data pairs $(x_1, y_1; x_2, y_2)$ to solve for m and b and thus allow glucose estimation when only the sensor signal, y is available. Matched data pairs can be created by matching reference data (for example, one or more reference glucose data points from a blood glucose meter, or the like) with substantially time corresponding sensor data (for example, one or more glucose sensor data points) to provide one or more matched data pairs, such as described in co-pending U.S. Patent Publication No. US-2005-0027463-A1. In some implantable glucose sensors, such as described in more detail in U.S. Pat. No. 6,329,161 to Heller et al., which is incorporated herein by reference in its entirety, the sensing layer utilizes immobilized mediators (e.g. redox compounds) to electrically connect the enzyme to the working electrode, rather than using a diffusional mediator. In some implantable glucose sensors, such as described in more detail in U.S. Pat. No. 4,703,756, the system has two oxygen sensors situated in an oxygen-permeable housing, one sensor being unaltered and the other contacting glucose oxidase allowing for differential measurement of oxygen content in bodily fluids or tissues indicative of glucose levels.

Advantageously, continuous analyte monitoring is provided by the preferred embodiments. For example, when the analyte is glucose, continuous glucose monitoring enables tight glucose control, which can lead to reduced morbidity and mortality among diabetic hosts. In the preferred embodiments, the medical staff is not unduly burdened by additional patient interaction requirements. Advantageously, there is no net sample (e.g., blood) loss for the host, which is a critical feature in some clinical settings. For example, in a neonatal intensive care unit, the host is extremely small and loss of even a few milliliters of blood can be life threatening. Furthermore, returning the body fluid sample to the host, instead of delivering to a waste container greatly reduces the accumulation of biohazardous waste that requires special disposal procedures. The integrated sensor system components, as well as their use in conjunction with an indwelling analyte sensor, are discussed in greater detail below.

A variety of known sensor configurations can be employed with the system of the preferred embodiments, such as U.S. Pat. No. 5,711,861, U.S. Pat. No. 6,642,015, U.S. Pat. No. 6,654,625, U.S. Pat. No. 6,565,509, U.S. Pat. No. 6,514,718, U.S. Pat. No. 6,465,066, U.S. Pat. No. 6,214,185, U.S. Pat. No. 5,310,469, and U.S. Pat. No. 5,683,562, U.S. Pat. No. 6,579,690, U.S. Pat. No. 6,484,046, U.S. Pat. No. 6,512,939, U.S. Pat. No. 6,424,847, U.S. Pat. No. 6,424,847, U.S. Patent Publication No. US-2006-0020187-A1, U.S. Patent Publication No. US-2007-0027370-A1, U.S. Patent Publication No. US-2005-0143635-A1, U.S. Patent Publication No. US-2007-0027385-A1, U.S. Patent Publication No. US-2007-0213611-A1, U.S. Patent Publication No. US-2008-0083617-A1, U.S. Patent Publication No. US-2008-0119703-A1, U.S. Patent Publication No. US-2008-0108942-A1, and co-pending U.S. patent application Ser. No. 12/055,114 filed on Mar. 25, 2008 and entitled "ANALYTE SENSOR.", for example. All of the above patents are incorporated in their entirety herein by reference and are not inclusive of all applicable analyte sensors; in general, it should be understood that the disclosed embodiments are applicable to a variety of analyte sensor configurations.

By way of example and not of limitation, a wide variety of suitable detection methods, such as but not limited to enzymatic, chemical, physical, electrochemical, immunochemical, optical, radiometric, calorimetric, protein binding, and microscale methods of detection, can be employed in the preferred embodiments, although any other techniques can be used in alternate embodiments. Additional description of analyte sensor configurations and detection methods can be found in U.S. Patent Publication No. US-2007-0213611-A1, U.S. Patent Publication No. US-2007-0027385-A1, U.S. Patent Publication No. US-2005-0143635-A1, U.S. Patent Publication No. US-2007-0020641-A1, U.S. Patent Publication No. US-2007-0020641-A1, U.S. Patent Publication No.

US-2005-0196820-A1, U.S. Pat. No. 5,517,313, U.S. Pat. No. 5,512,246, U.S. Pat. No. 6,400,974, U.S. Pat. No. 6,711,423, U.S. Pat. No. 7,308,292, U.S. Pat. No. 7,303,875, U.S. Pat. No. 7,289,836, U.S. Pat. No. 7,289,204, U.S. Pat. No. 5,156,972, U.S. Pat. No. 6,528,318, U.S. Pat. No. 5,738,992, U.S. Pat. No. 5,631,170, U.S. Pat. No. 5,114,859, U.S. Pat. No. 7,273,633, U.S. Pat. No. 7,247,443 U.S. Pat. No. 6,007,775, U.S. Pat. No. 7,074,610, U.S. Pat. No. 6,846,654, U.S. Pat. No. 7,288,368, U.S. Pat. No. 7,291,496, U.S. Pat. No. 5,466,348, U.S. Pat. No. 7,062,385 U.S. Pat. No. 7,244,582, U.S. Pat. No. 7,211,439, U.S. Pat. No. 7,214,190, U.S. Pat. No. 7,171,312, U.S. Pat. No. 7,135,342, U.S. Pat. No. 7,041,209, U.S. Pat. No. 7,061,593, U.S. Pat. No. 6,854,317, U.S. Pat. No. 7,315,752, and U.S. Pat. No. 7,312,040, all of which are incorporated herein by reference, in their entirety.

In some preferred embodiments, the system is configured such that at least the sensor's electroactive surfaces can be exposed to a sample and the sample's analyte concentration can be detected. Contacting the sensor 14 with the sample can be accomplished in a variety of ways, depending upon sensor/catheter configuration. A wide variety of catheter 12 and/or sensor configurations can be implemented in the preferred embodiments, to expose the sensor's electroactive surfaces to a biological sample. In one exemplary embodiment, the catheter is disposed in the host's peripheral vascular system, such as in a peripheral vein or artery, and a blood sample is taken up into the catheter such that the blood contacts the sensor's electroactive surfaces. In another exemplary embodiment, the catheter can be disposed in the host's central vascular system or in an extracorporeal blood flow device, such as but not limited to an arterial-venous shunt, an extravascular blood-testing apparatus, a dialysis machine and the like, wherein blood samples can be taken up into the catheter such that at least the sensor's electroactive surfaces are contacted by the drawn up blood sample.

In one exemplary embodiment, the sensor 14 is configured to reside within the catheter lumen (e.g., not protrude from the catheter tip); and the system is configured for the sample to be drawn back into the catheter lumen such that at least the sensor's electroactive surfaces are contacted by the sample. In some embodiments, the sensor is a small-structured sensor having a width of less than about 1 mm. In one preferred embodiment, the sensor has a width of less than about 0.4 mm. In a more preferred embodiment, the sensor has a width of less than about 0.2 mm. In some embodiments, the catheter 12 has an internal diameter of from about 0.2 mm or less to about 2.0 mm or more, preferably from about 0.5 mm to about 1.0 mm. In some embodiments, the sensor is configured such that its electroactive surfaces are at or adjacent to its tip, and a flow control device 130 draws back sample into the catheter lumen until the sample covers at least the electroactive surfaces. In some embodiments, the electroactive surfaces are distal from the sensor's tip and sample is drawn farther back into the catheter lumen until the sample covers the electroactive surfaces. In some embodiments, the tip of the sensor is disposed no more than about 3 cm, 2 cm, or 1 cm or less from a tip of the catheter.

In some embodiments, the system is configured such that a sample taken up into the catheter's lumen covers only a portion of the sensor's in vivo portion. In other embodiments, the sample taken up into the catheter's lumen covers the entire in vivo portion of the sensor 14. In some embodiments, a sample volume of from about 1 µl or less to about 2 ml or more is taken up into the catheter 12 and is sufficient to cover at least the electroactive surfaces of the sensor. For example, in some preferred embodiments, the sample volume is from about 1, 2, 3, 4, 5, 6, 7, 8, 9, 10, 20, 30, 40, 50, 60, 70, 80, 90 or 100-µl to about 200, 250, 300, 350, 400, 450, 500, 550, 600, 650, 700, 750, 800, 850, 900, 950 or 1000 µl. In some embodiments, the sample volume is about 1.25, 1.5, 1.75 or 2-ml or more.

In preferred embodiments, the sample taken up into the catheter's lumen remains within the in vivo portion of the catheter 12. For example, in some embodiments, the sample is not drawn so far back into the catheter that it enters the ex vivo portion of the catheter, the tubing 134 or the reservoir 132. In some embodiments, however, the sample can be drawn back as far as the catheter hub and/or fluid coupler but not into the IV tubing connected to the catheter hub/fluid coupler. In some embodiments wherein the catheter is implanted in a host, the blood sample never leaves the host's body (e.g., a plane defined by the host's skin). In some embodiments wherein the catheter is implanted in an extracorporeal device, the sample does not substantially exit the extracorporeal device. In preferred embodiments, wherein blood is taken up into the catheter, the blood is returned to the host (or extracorporeal device), which is described elsewhere herein. In preferred embodiments, the sample is blood taken up from the host's circulatory system and into the catheter disposed within the circulatory system.

IV Fluids

Referring again to FIGS. 1-2, in preferred embodiments, the system is configured and arranged for use of at least one fluid reservoir 132, such as but not limited to an IV bag held on a support or stand 136, that contains an infusion fluid 132a, such as but not limited to reference (e.g., calibration), hydration, medicament and/or flushing solutions. For simplicity, the infusion fluid will be referred to herein as a solution. However, one skilled in the art recognizes that a wide variety of infusible fluids can be used in the embodiments discussed herein.

In some embodiments, the system is configured and arranged for use with a reservoir 132 that includes a container such as but not limited to an IV bag. In various preferred embodiments, the solutions 132a are administered with standard IV administration lines, such as those commonly used today, such as a sterile, single-use IV set, referred to herein as tubing 134. The tubing can be provided with or separately from the solution(s). In some circumstances, two or more IV bags or a multi-compartment IV bag can be used. In some circumstances, two starting IV are used and a mixing valve is used to mix the two solutions together to provide an infusion solution containing the desired proportions of the first two starting solutions. In some circumstances, the reservoir is a multi-compartment container, such as but not limited to a multi-compartment IV bag. In some embodiments, it is preferred to use a single solution. Use of a single solution for calibration, catheter flushing and the like simplifies the system by reducing the complexity and/or number of system components required for system function. In some embodiments, two or more solutions are preferred, and can be provided by a multi-compartment IV bag or two or more separate reservoirs (e.g., two or more bags, each containing a different solution). Advantageously, use of multiple solutions can increase system functionality and can improve sensor accuracy.

Any infusion fluid (e.g., solution 132a) known in the art can be used in conjunction with the present system. In some embodiments, the solution is an analyte-containing solution that can be used as a reference or standard for sensor 14 calibration (e.g., also referred to as a reference and/or calibration solution in the art). In some embodiments, a solution can be used as a flushing solution, to wash a sample off the sensor and out of the catheter 12. In some embodiments, the IV solution can contain a medicament, such as but not limited to beta blockers, anticoagulants, dopamines, alteplase, anistreptases, benztropine, calcium, dalteparin, diltiazem, diphenhydramine, dopexamine, enoxaparin, ephedrine, heparin, insulin, ketorolac, magnesium sulfate, metoprolol, milrinone, nalmefene, naloxone, nicardipine, nimodipine, phenyloin, physostigmine, rocuronium, sodium thiosulphate, streptokinase, urokinase, vasopressin, and verapamil. In some embodiments, one, two or more solutions can be used in conjunction with the present system. For example, in some embodiments, two or more calibration solutions (e.g., solutions with different analyte concentrations) can be used. In some embodiments, multiple solutions can be infused through a multi-lumen catheter, such as but not limited to a two-lumen or three-lumen catheter. In some embodiments, the sensor is disposed in one of the catheter's lumens, through which one or more calibration solutions can be passed, while other fluids (e.g., hydration fluids, drugs, nutritional fluids) to be delivered to the patient are infused through the other catheter lumens (e.g., second, third or more lumens).

In one exemplary embodiment, the analyte sensor is a glucose sensor, and the solution contains dextrose or glucose at a concentration of from about 0 mg/dl to about 400 mg/dl. In preferred embodiments, the solution contains from about 75 mg/dl to about 200 mg/dl glucose. In more preferred embodiments, the solution contains from about 100 mg/dl to about 150 mg/dl glucose. In some embodiments, the solution 132a is an isotonic saline solution. In some embodiments, the solution contains a sufficient concentration of an anticoagulant to substantially prevent blood clotting in and/or near the catheter 14. In some embodiments, the solution contains a sufficient concentration of or antimicrobial to substantially prevent infection in and/or near the catheter. In one exemplary embodiment, the reservoir is a 500 ml bag containing saline. In some embodiments, an amount of calibrant and/or medicament can be mixed into the IV bag to give a desired final concentration. In some embodiments, the processor module is configured to adapt the flow profile, responsive to the host's analyte concentration and/or to the presence of a medicament in the solution. For example, if an infusion solution contains insulin, and the host's glucose is above a programmed range/level (e.g., as determined via the analyte sensor), the processor module can modify and/or re-program the flow profile such that the flow control device will deliver a sufficient amount of the insulin solution to lower the host's blood glucose to the programmed range/level.

In another exemplary embodiment, the analyte sensor 14 is a glucose sensor and the calibration solution includes a glucose concentration of from 0 mg/dl to about 400 mg/dl or more. In one exemplary embodiment, a single calibration solution (e.g., having a 100 mg/dl glucose concentration) can be used. In another exemplary embodiment, two calibration solutions (e.g., having 100 mg/dl and 0 mg/dl glucose concentrations) can be used. In other exemplary embodiments, three calibration (e.g., 0 mg/dl glucose, 75 mg/dl glucose and 300 mg/dl glucose) solutions can be used. In still other embodiments, more than three calibration solutions can be used. In addition to calibration solutions, non-calibration solutions can be used in conjunction with the integrated sensor system, such as but not limited to intravenously administered drugs, insulin, enzymes, nutritional fluids, and the like.

System Electronics

Figure 5:
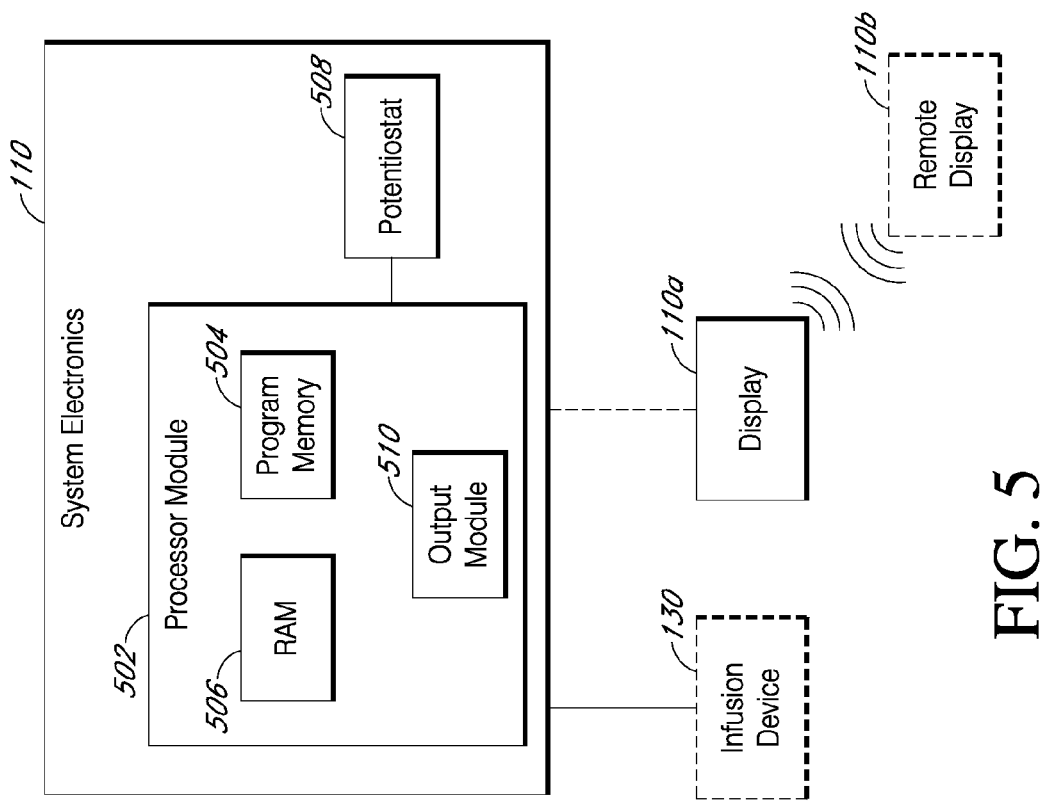
FIG. 5 is a block diagram of system electronics, in one embodiment.

FIG. 5 is a block diagram that illustrates one exemplary embodiment of the system electronics 110, also referred to as a "computer system" that can include hardware, firmware, and/or software that enable measurement and processing of data associated with analyte levels in the host and control of the flow control device. In preferred embodiments, the electronics are operably connected to the analyte sensor 14 and the electronic cable 120, and are configured for communication with a flow control device 130 (e.g., see FIGS. 1-2). The system electronics include a processor module 502 configured to control various system functions, such as the functions of the analyte sensor and of a flow control device 130, such as but not limited to receiving and processing the sensor signal, sensor calibration, collecting and/or analyzing data, regulating the flow of an infusion fluid into the host and draw-back of samples.

The system electronics include a potentiostat 508 that is operatively connected to the sensor and provides a voltage to the electrodes, which biases the sensor to enable measurement of a current value indicative of the analyte concentration in the host (also referred to as the analog portion). The potentiostat can have one channel or multiple channels, depending on the number of working electrodes, for example. In some embodiments, the potentiostat includes a resistor (not shown) that translates the current into voltage. In some embodiments, a current to frequency converter is provided that is configured to continuously integrate the measured current, for example, using a charge counting device. In some embodiments, an A/D converter digitizes the analog signal into "counts" for processing. Accordingly, the resulting raw data stream in counts is directly related to the current measured by the potentiostat 508.

A processor module 502 is the central control unit that controls the processing of the system electronics 110. In some embodiments, the processor module is formed as part of a custom chip, such as an ASIC, however a computer system other than an ASIC can be used to process data as described herein, for example a microprocessor can be used for some or all of the sensor's central processing. The processor module typically provides a program memory 504, which provides semi-permanent storage of data, for example, storing data such as sensor identifier (ID) and programming to process data streams (for example, filtering, calibration, fail-safe checking, flow profile(s) and the like). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like. In one exemplary embodiment, RAM 506 can be used for the system's cache memory, for example for temporarily storing recent sensor data.

In some embodiments, the processor module 502 comprises a digital filter, for example, an IIR or FIR filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter, the processor module can be programmed to request a digital value from the integrator at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter.

In some embodiments, the processor module is further configured to build a data packet for transmission to an outside source, e.g., via telemetry, to a display device as described in more detail elsewhere herein. Generally, the data packet comprises a plurality of bits that can include a sensor/sensor electronics module ID code, raw data, filtered data, calibrated data, rate of change information, trend information, error detection or correction, and/or the like.

In some embodiments, the system electronics include a data storage memory (not shown) that is operably connected to the processor module 502 and is configured to store a variety of sensor information and/or information related to controlling the flow control device. In some embodiments, the data storage memory stores 1, 3, 4, 5, 6, 7, 8, 9, 10, 11, 12, 13, 14, 15, 20, 30 or more days of continuous analyte sensor data. In some embodiments, the data storage memory stores sensor information such as raw sensor data (one or more raw analyte concentration values), filtered sensor data (one or more filtered analyte concentration values), calibrated sensor data (one or more calibrated analyte concentration values), and/or otherwise processed sensor data (e.g., rate of change information, trend information, rate of acceleration information, sensor diagnostic information, alarm/alert information, calibration information, and/or the like). In some embodiments, system electronics are configured to receive and store information in the data storage memory (and/or program memory), including information related to the sensor's host (e.g., ID, medicaments, treatment protocols associated with the patient), one or more flow profiles, types of available infusion solutions (including medicaments), treatment protocols, types of infusion devices, types of catheters, allowed system configurations, and the like. In some embodiments, user parameters can be programmed into (and/or modified in) the data storage memory (and/or program memory 504) of the system electronics, via a display device such as a personal computer, personal digital assistant, or the like. Preferably, user parameters include contact information, alert/alarms settings (e.g., thresholds, sounds, volume, and/or the like), calibration information, font size, display preferences, defaults (e.g., screens), and/or the like. In some embodiments, the data storage memory is configured to store data related to the flow profile, infusion fluids, flow control devices, treatment protocols, and the like. Alternatively, the system electronics can be configured for direct programming of certain user parameters.

Although separate data storage and program memories are described here, one skilled in the art appreciates a variety of configurations, including one or multiple memories that provide the necessary storage space to support the sensor's data processing and storage requirements. Accordingly, the described location of storage of any particular information and/or or programming is not meant to be limiting, but rather exemplary.

In some embodiments, the system electronics are configured to perform smoothing and/or filtering algorithms on the sensor data (e.g., raw data stream and/or other sensor information), wherein the smoothed and/or filtered data is stored in the data storage memory as sensor information. Co-pending U.S. Patent Publication No. US-2005-0043598-A1, U.S. Patent Publication No. US-2007-0032706-A1, U.S. Patent Publication No. US-2007-0016381-A1, and U.S. Patent Publication No. US-2008-0033254-A1 describe some algorithms useful in performing data smoothing and/or filtering herein (including signal artifacts replacement), and are incorporated herein by reference in their entirety.

In some embodiments, the system electronics are configured to calibrate the sensor data, and wherein the data storage memory stores sensor information including non-calibrated sensor data points and/or calibrated sensor data points. In some further embodiments, the sensor electronics module is configured to wirelessly receive calibration information from a display device, from which the sensor electronics module is configured to calibrate the sensor data. U.S. Pat. No. 7,310,544 and U.S. Pat. No. 6,931,327 describe some algorithms useful in sensor calibration herein, and are incorporated herein by reference in their entirety.

In some embodiments, the system electronics are configured to perform additional algorithmic processing on the sensor data (e.g., raw data stream and/or other sensor information) and the data storage memory is configured to store the processed sensor data and/or sensor diagnostic information associated with the algorithms. U.S. Pat. No. 7,310,544 and U.S. Pat. No. 6,931,327 describe some algorithms that can be processed by the sensor electronics module, and are incorporated herein by reference in their entirety.

In preferred embodiments, the system electronics include an output module 510 configured and arranged to operably connect with a flow control device 130 such that the processor module controls the flow profile of the flow control device. In some embodiments, the components and functions of the system electronics can be divided into two or more parts, such as between the catheter connector 18, on the fluid coupler 20 or on the electronic cable.

In preferred embodiments, the system electronics are configured to control the function of the flow control device, such as via processor module, the output module and a flow profile programmed to direct movement/function of the flow control device. Flow profiles are described in the section entitled "Flow Profiles." The system is configured and arranged for use with a variety of flow control devices. For example, a peristaltic pump can be used in some embodiments. As a non-limiting example, a peristaltic pump may include a plurality of rollers adapted to displace fluid along a segment of flexible tubing. The tubing is connected to an implanted catheter, such that the displaced fluid is infused into the host. As is known in the art, the rate and direction of rotation of the rollers can control the rate of fluid infusion. For example, increasing/decreasing the rate of the rollers moving in a "forward" direction increases/decreases the infusion rate. In another example, moving the rollers in a "backwards" direction can draw back a sample of the host's circulatory system (e.g., blood) into the vascular access device. The movement of the rollers can be controlled by programming referred to herein as a "flow profile." A variety of flow control devices suitable for use with the present invention are available on the market, such as but not limited to peristaltic pumps, syringe pumps and ambulatory pumps, such as the exemplary devices described in U.S. Pat. No. 4,685,903, U.S. Pat. No. 4,898,578, U.S. Pat. No. 4,925,444, U.S. Pat. No. 5,158,437, U.S. Pat. No. 5,219,279, U.S. Pat. No. 5,207,642, U.S. Pat. No. 5,248,300, U.S. Pat. No. 5,321,392, U.S. Pat. No. 5,496,273, U.S. Pat. No. 5,522,798, U.S. Pat. No. 5,482,446, U.S. Pat. No. 5,547,470, U.S. Pat. No. 5,551,850, U.S. Pat. No. 5,630,710, U.S. Pat. No. 5,681,285, U.S. Pat. No. 5,685,844, U.S. Pat. No. 5,745,378, U.S. Pat. No. 6,231,320, U.S. Pat. No. 6,231,560, U.S. Pat. No. 6,269,340, U.S. Pat. No. 6,544,229, U.S. Pat. No. 6,648,821, U.S. Pat. No. 6,817,990, U.S. Pat. No. 6,692,457, U.S. Pat. No. 6,985,870, U.S. Pat. No. 7,018,361, U.S. Pat. No. 7,109,878, U.S. Pat. No. 7,204,823, U.S. Pat. No. 7,402,153, U.S. Pat. No. 7,417,729, U.S. Patent Publication No. US-2007-0060871-A1, U.S. Patent Publication No. US-2007-0112298-A1, U.S. Patent Publication No. US-2007-0213657-A1, U.S. Patent Publication No. US-2007-0299389-A1, U.S. Patent Publication No. US-2008-0033357-A1, U.S. Patent Publication No. US-2008-0097326-A1, U.S. Patent Publication No.

US-2008-0103447-A1, U.S. Patent Publication No. US-2008-0154177-A1, U.S. Patent Publication No. US-2008-0147050-A1, U.S. Patent Publication No. US-2008-0161753-A1, and U.S. Patent Publication No. US-2008-0200897, each of which is incorporated herein by reference in its entirety. Additional types of infusion devices can be used with the present system, such as but not limited to syringe pumps and insulin pumps.

In some embodiments, the system electronics are configured to interact with a display 110*a*, which, in some embodiments, is configured and arranged to releasably mate with the system electronics, to communicate with the system electronics via wires and/or wireless means, or is wholly incorporated into at least a portion of the system electronics. The display can include one or more buttons, a liquid crystal display (LCD), a vibrator, an audio transducer (e.g., speaker), backlight, and/or the like, and provide controls for the user/operator to interact with the system electronics. For example, one or more buttons can allow toggle, menu selection, option selection, mode selection, yes/no response to on-screen questions, a "turn off" function (e.g., for an alarm), a "snooze" function (e.g., for an alarm), a reset, and/or the like. The LCD can be provided, for example, to provide the user/operator with visual data output. An audio transducer (e.g., speaker) can be included to provide audible signals or alerts for one or more alarm conditions such as present and/or predicted hyper- and hypoglycemic conditions.

In some embodiments, the system electronics are configured and arranged to communicate with a remote display 110*b*, such as by a wires or wireless connection. A remote display can be located at a nurse's station or other remote location, whereby the host and function of the system can be monitored remotely. For example, an alarm can be transmitted to a remote display located at a nurse's station, whereby the operator is alerted that the host is in need of assistance. While the embodiment shown depicts the remote display wirelessly communicating with the system via the display, one skilled in the art understands that a variety of configurations are possible and that additional components can be included to affect various forms of wired and wireless communication commonly used in a hospital setting.

In preferred embodiments, the system electronics are coupled with an electronic cable 120, which in turn is coupled with an electronic connector 120*a*. The electronic connector can be any type of electronic connector configured and arranged to releasable couple with a flow control device 130, such that the system electronics 110 can communicate with the flow control device and/or such that the system can draw power from the flow control device. In some embodiments, the system electronics are configured and arranged to be powered at least in part by a flow control device. In an exemplary embodiment, the system electronics can draw all of the power required to function, including powering the analyte sensor, from the flow control device. In some embodiments, the system electronics can include a battery, such that only a portion of the required power is provided by the flow control device, or to provide back-up power in the event of a loss of power from the flow control device. In some embodiments, the system electronics are actuated (e.g., turned on, initiated, initialized) upon engagement of the system electronics with a flow control device. For example, in one embodiment, the system electronics begin to draw power from the flow control device upon coupling (e.g., "plugging in"), and the initial receipt of power triggers the electronics module to turn on. In some embodiments, the system electronics are actuated (e.g., turned on) after making an electrical connection with the flow control device, by actuation of a switch. For example, in one embodiment, the system is configured such that a caretaker can apply the sensor/catheter to the host (e.g., including hooking up the IV line), plug the electronic cable into the flow control device and then turn on the system by pushing a button located on the system electronics and/or automatically.

In some embodiments, the system electronics 110 are non-releasably connected with the analyte sensor 14. For example, in FIGS. 3A-3C, the system electronics are physically incorporated into the fluid coupler 20, the electronic cable 120 (e.g., which is non-releasably connected to the sensor through the fluid coupler), and the catheter's hub 18, respectively. However, in other embodiments, the system is configured such that the system electronics are releasably connected to the analyte sensor. For example, in some embodiments, the fluid coupler 20 and the system electronics can be configured to releasably mate (e.g., such that they can electronically communicate), such as via a plug and socket or via male and female connectors (e.g., using electrical contacts), or by any other method known in the art. Similar releasable connection between the hub of the catheter shown in FIG. 3C and the system electronics are also contemplated. In still other embodiments, the system can be configured such that the individual components are configured and arranged to connect in series. For example, in one embodiment, the electronics are disposed in a housing comprising two connectors. A first connector is configured and arranged to releasably mate with (e.g., plug into, connect with, functionally couple with) the fluid coupler (and thereby make an electronic connection with the sensor), and a second connector is configured and arranged to releasably mate with an electronic cable, which in turn is configured to releasably mated with a flow control device. Additional configurations are also contemplated.

Flow Profiles

Figure 6:
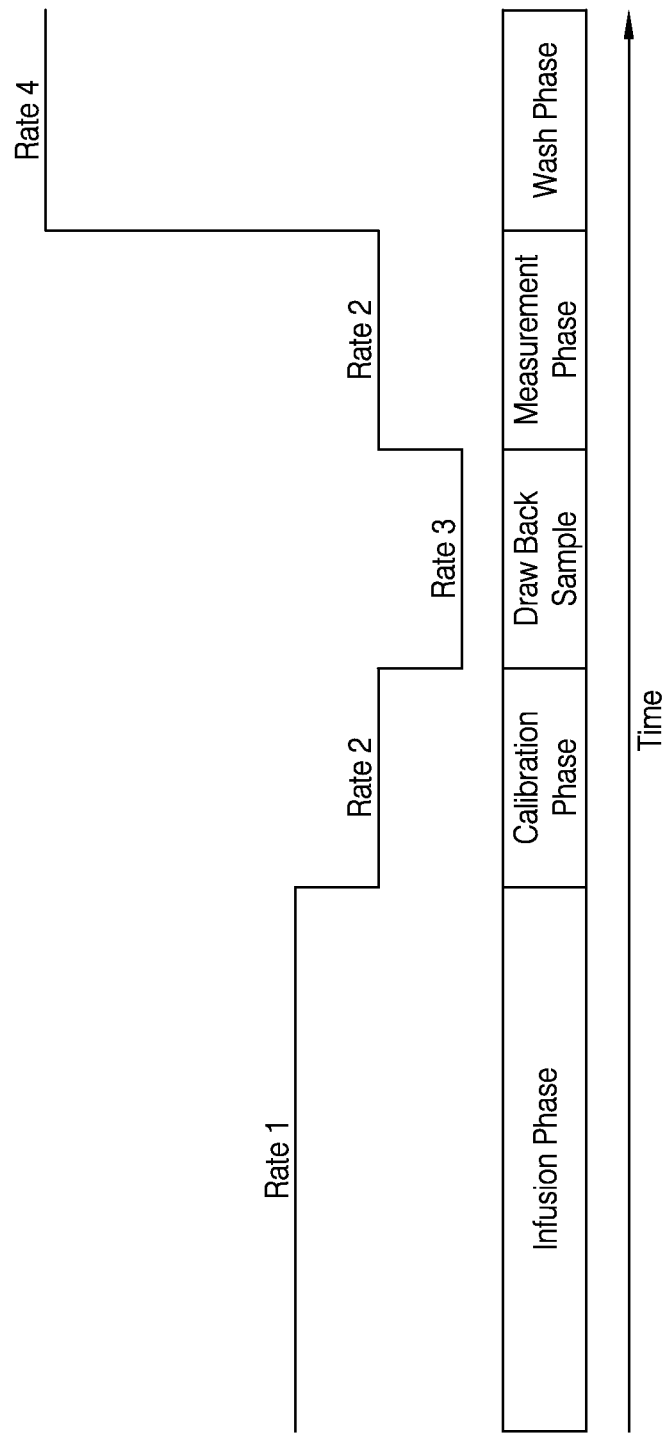
FIG. 6 is a graph illustrating a portion of an exemplary flow profile for a flow control device, in one embodiment.

FIG. 6 is a graph illustrating an exemplary flow profile, in one embodiment. Preferably, the processor module 502 comprises the flow profile, which includes programming for controlling the fluid flow of a flow control device 130, such as an infusion pump or valve described elsewhere therein. In some embodiments, the flow control device includes a flow profile, and the processor module is configured to control, program, re-program, modulate and/or enter values/commands the flow control device's internal flow profile. In preferred embodiments, the processor module is configured to intermittently control the flow of fluids through an implanted vascular access device, as defined by the flow profile. For example the flow profile defines the amounts, times and/or rates of fluid infusion into the host (e.g., via the implanted vascular access device) and/or the amounts, times and/or rates of sample draw-back from the host's circulatory system (e.g., blood), such that the analyte sensor is contacted (e.g., bathed) with the sample.

As shown in FIG. 6, in some embodiments, a flow profile can be divided into one or more phases. In some embodiments, the phases of the flow profile are functional phases, such as but not limited to a calibration phase, a measurement phase, a wash phase, a flush phase, a keep vein open (KVO) phase, an infusion phase, and the like, that are correlated with movement of the flow control device, which in turn causes fluid infusion and/or draw back of sample, for specified periods of time and at one or more programmed rates. In some embodiments, the rates of fluid flow (forward and/or backward) and times of a phase are optimized to achieve a function.

As a non-limiting example, the flow profile shown in FIG. 6 includes an infusion phase, a calibration phase, a period of sample draw back, a measurement phase and a wash phase. While the illustrated flow profile includes only five phases, wherein each phase includes a single flow rate, in other embodiments, a flow profile can include more or fewer phases. Additionally, each phase can include one or more rates. In preferred embodiments, the flow rates and durations are optimized to achieve a desired function, such as but not limited to infusing an amount of fluid into the host (including a specific amount of medicament), contacting the sensor with a sample sufficient for analyte measurement, measurement of one or more analytes in the sample, returning the sample to the host, washing the sensor and/or the vascular access device, and the like. Useful flow rates and times are described in greater detail herein.

In some embodiments, the processor module is configured to modify (e.g., adaptively modify, adjust, change, program and/or re-program) the flow profile (e.g., rates and/or timing), responsive to host analyte levels (e.g., as determined by the system electronics via the analyte sensor) and/or in response to input from a user, as described elsewhere herein. In some embodiments, the processor module is configured to communicate flow and drawback times, rates, and the like, to a flow control device via the output module. In some embodiments, the processor module comprises the flow profile. In some embodiments, the flow control device includes one or more flow profiles and the processor module is configured to program and/or select a flow profile of the flow control device, such as but not limited to by entering values into the flow control device's flow profile, such that the desired flow rates and drawbacks are achieved. In preferred embodiments, the processor module is configured to modify (e.g., adapt, adjust, program and/or reprogram) the flow profile, responsive to parameters, such as analyte levels, the presence of a medicament in the infusion solution, fail-safes, and the like. In some embodiments, the processor module includes programming for processing information from the sensor and/or information by a user (e.g., contents of the infusion fluid, type and/or size of catheter, hospital protocol, type of infusion device, system configuration, etc.) and calculating the flow profile, making adjustments to the flow profile, and the like. In some embodiments, the processor module is configured to use a look-up table, to modify the flow profile. In some embodiments, the flow profile comprises a plurality of selectable flow profiles. For example, the processor module can select from a menu of flow profiles, responsive to host analyte levels and/or user input of parameters, in some embodiments. In some embodiments, the processor module is configured to use input information, such as but not limited to parameters related to the host, the host's treatment, the type of infusion solution, the identity of the flow control device, and the like, to select and/or program a flow profile.

Referring again to FIGS. 1-2, in preferred embodiments, the system electronics include an output module configured and arranged to operably connect with (e.g., communicate with) a flow control device such that the processor module controls the flow profile of the flow control device, such as via connector 120a. For example, the output module can be configured to communicate the flow profile from the processor module to the flow control device. In some embodiments, the output module is configured and arranged for wireless communication with the flow control device, such as is known in the art and is described elsewhere herein. In some embodiments, the output module is configured and arranged to communicate with two or more infusion devices. For example, two or more infusion devices can be linked in parallel or in serial, for infusion of a plurality of solutions into the host. In another example, a medicament pump, such as but not limited to a syringe pump and/or an ambulatory infusion device, can be piggy-backed onto the flow control device. In some embodiments, the output module is configured and arranged for communication with an optional local user interface 110a (see FIG. 2). The system electronics can be configured to communicate with the optional local display using either wired or wireless means. In some embodiments, the output module is configured and arranged to communicate with an optional remote user interface 110b, such as a communication console at the nurse's station or in the doctor's office, via wired and/or wireless means, as are known in the art. A user interface can include a display and a module for inputting information, selecting protocols, and the like, such as a scroll wheel, a keypad, and the like, as is known in the art.

As a non-limiting example, in some embodiments, the sensor 14 dwells within the lumen of the catheter 12, as described elsewhere herein. In some embodiments, the processor module is configured to control fluid delivery to the host and sample take-up (e.g., drawing blood back into the catheter until at least the sensor's electroactive surfaces are contacted by the blood), such as via a flow profile. In some embodiments, wherein an internal calibration is performed (e.g., calibration phase), an infusion fluid (e.g., calibration solution 132a) flows over the indwelling sensor and is infused into the host. Generally, analyte in the solution can be measured when the sensor electroactive surfaces are in contact with the solution. In some embodiments, the measurements of the solution can be used to calibrate the sensor. After calibration, the system is configured such that a sample (e.g., blood or other bodily fluid) contacts the sensor's electroactive surfaces (e.g., by drawing blood back into the catheter; analyte measurement phase). When the sample contacts the electroactive surfaces, the sample's analyte concentration can be detected by the sensor. When a sample is drawn back, the sample can then be returned to the host. In some embodiments, the system cycles between calibration (e.g., measurement of a reference calibration solution) and measurement (e.g., of a sample, such as blood, analyte concentration) phases. In some embodiments, the system continues operation in this cyclical manner, until the system is either disconnected from the host, turned off for a period of time (e.g., during movement of the host from one location to another) and/or disconnected from the flow control device. For example, in one embodiment, the system cycles between the calibration and measurement steps from about every 15, 20, 30, 40, 50 or 60 seconds to about every 2, 3, 4, 5, 6, 7, 8, 9, 10, 15, 20, 25, 30, 35, 40, 45, 50, 55 or 60-minutes to about every 1.5, 2, 2.5 or 3-hours or more. In some embodiments, the user can adjust the time between steps. In some embodiments, the user can adjust the time between each step. In some embodiments, the system can perform additional steps, such as but not limited to a flushing step, a keep vein open step (KVO), an extended infusion step, and the like. In some embodiments, the length of time is dependent upon sensors that detect a reference solution (e.g., calibration solution) and/or sample (e.g., blood) at the electroactive surfaces.

In some embodiments, the flow profile can be divided into functional phases, wherein the amount and/or rate of fluid movement accomplishes a function such as but not limited to washing the sensor, exposing the sensor to a calibrant, drawing back and exposing the sensor to a sample, returning a sample to the host, and the like. In one exemplary embodiment, the flow profile is configured to move a volume of fluid from about 1, 2, 3, 4, 5, 6, 7, 8, 9, 10, 15, 20, 25, 30, 35, 40, 45, 50, 55, 60, 65, 70, 75, 80, 85, 90, 95 or 100-µl or less to about 125, 1250, 200, 250, 300, 350, 400, 450, 500, 550, 600, 650, 700, 750, 800, 850, 900, 950 or 1000-µl or more. In general, the volume of fluid pushed through the catheter in a particular phase (e.g., calibration phase) is dependent upon the timing of the phase. For example, in one embodiment, if a long phase, such as a 20 minute calibration phase (e.g., as compared to a shorter 5 minute phase) were selected and/or programmed, the volume of fluid pushed during the long phase would be 4× greater than the volume of fluid pushed during the shorter phase. Accordingly, one skilled in the art appreciates that the above described ranges of fluid infusion can be increased and/or decreased by increasing or decreasing the measurement phase and/or intervals (i.e., timing). In preferred embodiments, the fluid is moved at a flow rate that is sufficiently slow that the calibration solution's temperature substantially equilibrates with the temperature of the tissue surrounding the in vivo portion of the catheter and/or temperature of bodily fluid (e.g., blood), such that the temperature of the calibration solution and the temperature of the blood are substantially the same. In some embodiments, the flow rate during the calibration phase is from about 0.0, 0.01, 0.05, 0.1, 0.15, 0.2, 0.25, 0.5, 0.75, 1.0, 1.25, 1.50, 1.75, 2, 3, 4, 5, 6, 7, 8, 9, 10, 15, 20, 30, 40, 50, 60, 70, 80 or 90-µl/min or less to about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0 or 10.0 ml/min or more. In some embodiments, it is preferred to make the calibration measurements when the flow rate is 0.0-ml/min, since calibration measurements are more repeatable at this flow rate as compared with calibration measurements taken at higher flow rates. In some embodiments, the calibration fluid is infused for a period of time, then the flow is paused (e.g., at 0.0-ml/min) and the calibration measurements are taken.

As a non-limiting example, in some embodiments, the sensor can be calibrated using one or more reference solutions. For example, if the analyte is glucose, a suitable reference solution (e.g., calibration solution) is saline containing 0, 25, 50, 75, 100, 125, 150, 175, 200, 225, 250, 275, 300 mg/dl glucose or more. In some embodiments, two or more such reference solutions can be used to calibrate the sensor, such as but not limited to by intermittently infusing each of the two or more reference solutions. In some embodiments, a baseline value of the sensor can be obtained by generating a signal when the sensor is exposed to a 0-mg/dl analyte reference solution (or an alternative reference solution concentration). In some embodiments, updated baseline values are continuously obtained by repeatedly exposing the sensor to reference solution, such as every 1, 2, 3, 4, 5, 10, 20, 30, 40, 60 or more minutes. In some embodiments, updated baseline values are continuously obtained by exposing the sensor to the reference solution for periods of time and continuously collecting baseline values. For example, the sensor can be exposed to the reference solution for 5, 10, 15, 20, 25, 30, 40, 50, or 60 minutes, or longer, while baseline signals are continuously generated. In this embodiment, sensitivity m calibration values can be obtained intermittently by exposing the sensor to an analyte-containing reference solution intermittently, such as but not limited to every 5, 10, 15, 20, 25, 30, 40, 50, or 60 minutes, or longer, such as at the conclusion of the exposure to the reference solution. In other embodiments, such calibrations measurements (e.g., to obtain a baseline value and sensitivity) are performed "intermittently," such as once every 1, 2, 4, 6, 8 10, 12, 18, 24 or 36 hours. In some embodiments, a reference blood analyte value (e.g., glucose) can be determined using an external means, such as testing of a withdrawn blood sample using a hand-held analyte meter or lab meter (e.g., a finger-stick meter or a YSI device) and entered into the system, for use in sensor calibration and the like. In still other embodiments, the analyte sensor is a dual-electrode analyte sensor configured and arranged to generate a reference analyte value, such as but not limited to a sensitivity value, when exposed to a reference solution (including a known analyte concentration) in order to calibrate the sensor using only one solution (e.g., wherein the dual electrode sensor enables subtraction of a baseline from the analyte signal). In some further embodiments, an external reference value is used in combination with the dual-electrode data to calculate sensor sensitivity, such as for determination of baseline offset. Additional methods of determining baseline and/or sensitivity are known in the art, such as described in co-pending U.S. patent application Ser. No. 12/055,114, filed on Mar. 25, 2008 and entitled "Analyte Sensor," which is incorporated herein by reference in its entirety.

In general, the system is configured intermittently contact the sensor with a sample (e.g., blood). For example, in some embodiments, the flow control device is directed to take up a sufficient volume of sample such that at least the sensor's electroactive surfaces are contacted by the sample. In some embodiments, a sample volume of from about 1, 2, 4, 6, 8, 10, 20, 30, 40, 50, 60 70, 80, 90, 100, 125, 150, 175, 200, 250, 300, 350, 400, 450 or 500-µl or less to about 0.6, 0.7, 0.8, 0.9, 1, 1.5, 2, 3, 4 or 5-ml or more is taken up into the catheter 12 and/or fluid coupler 20 and is sufficient to cover at least the electroactive surfaces of the sensor 14. In some embodiments, the sample taken up into the catheter is taken up substantially no farther than the skin (or a plane defined by the skin of the patient). In some embodiments, the sample is taken up into the catheter substantially no farther than the catheter's inner lumen (e.g., substantially not into the IV tubing.) In some embodiments, the sample is taken up no farther than the catheter's connector 18 or the fluid coupler 20 connected to the catheter.

In some embodiments, the rate of sample take-up is sufficiently slow that the temperature of the sample substantially equilibrates with the temperature of the surrounding tissue. Additionally, in some embodiments, the rate of sample take-up is sufficiently slow such that substantially no mixing of the sample and solution 132a occurs. In some embodiments, the flow rate during is the measurement phase is from about 0.0, 0.001, 0.01, 0.025, 0.05, 0.075, 0.1, 0.15, 0.2, 0.25, 0.5, 0.75, 1.0, 1.25, 1.50, 1.75, 2, 3, 4, 5, 6, 7, 8, 9, 10, 15, 20, 30, 40, 50, 60, 70, 80 or 90-µl/min or less to about 0.1, 0.2, 0.3, 0.4, 0.5, 0.6, 0.7, 0.8, 0.9, 1.0 or, 2.0-ml/min or more. It is appreciated by one skilled in the art that notation for sample draw-back (in a flow profile) can include a negative (−) flow rate (e.g., −0.5 ml/hr). In some embodiments, it is preferred to make the blood analyte measurements when the flow rate is 0.0-ml/min, since such measurements are more repeatable at this flow rate as compared with blood analyte measurements taken at higher flow rates. In some embodiments, the system draws back a sufficient amount of blood that the sample contacting the sensor is undiluted, then the flow is paused (e.g., at 0.0-ml/min) and the blood analyte measurements are taken.

Measurements of sample analyte concentration can be taken while the sensor's electroactive surfaces are in contact with the sample. The processor module controls sample analyte measurement, as described elsewhere herein. In some embodiments, one sample measurement is taken. In some embodiments, a plurality of sample measurements are taken, such as from about 2 to about 50 or more measurements and/or at a sample rate of from about 1 measurement per every 1, 2, 5, 10, 15, 20, 25, 30 or 45-seconds to about 1 measurement per minute. In preferred embodiments, sample measurements are taken substantially continuously, such as but not limited to substantially intermittently, as described elsewhere herein.

Generally, after a measurement phase, the flow profile is configured for a flush (e.g., wash) phase, wherein the solution 132a is flushed through the catheter and/or fluid coupler, to ensure that a sufficient amount of the sample has been removed from the sensor 14 and the catheter/fluid coupler lumen, such that a calibration measurement can be taken. However, in some embodiments, sample is collected, measured and flushed out, followed by collection of the next sample, substantially without sensor calibration; the flush phase/step can be executed between samples to ensure that the sample being analyzed is substantially uncontaminated by the previous sample. In some embodiments, a relatively extended flush is used, while in other embodiments the flush is just long enough to ensure no blood remains.

In some embodiments, the effectiveness of the flushing movement is dependent upon the solution 132a composition (e.g., concentrations of sodium chloride, glucose/dextrose, anticoagulant, etc.). Accordingly, the amount of solution required to ensure that substantially no sample remains in the catheter/fluid coupler and/or on the sensor 14 can depend on the solution composition. For example, relatively more flushing may be required to completely remove all of the sample when a non-heparinized solution is selected than when a heparinized solution is selected. In some embodiments, the effectiveness of the flushing is also dependent upon the flush flow rate. For example, a relatively faster flow rate can be more effective in removing sample from the sensor than a slower flow rate, while a slower flow rate can more effectively move a larger volume of fluid. Accordingly, in some embodiments, the length (e.g., time period) of flushing selected is dependent upon the calibration solution and flow rate selected. In some embodiments, the flush/wash phase flow rate is from about 0.25 µl/min or less to about 1, 2, 3, 4, 5, 6, 7, 8, 9, 10, 20, 30, 40, 50, 60, 70, 80, 90 or 100-ml/min or more, and lasts for a time period of from about 5, 10, 15, 20, 30 or 50 seconds or less to about 1, 2, 3, 4, 5, 6, 7, 8, 9 or 10 minutes or more. In some circumstances, the flow rate can be as high as 200, 300, 400, 500 or 600, 700-ml/min or more, from about 10, 20, 30 40 or 50 seconds to about 1, 2 or 3 minutes or longer.

In preferred embodiments, the flush/wash step/phase of the flow profile returns the sample (e.g., blood) to the host, such that the host experiences substantially no net sample loss. Further more, the flush washes the sensor 14 and catheter/fluid coupler lumen of a sufficient amount of sample, such that an accurate calibration measurement (e.g., of undiluted solution 132a) can be taken during the next phase of system operations.

Thrombosis and catheter occlusion are known problems encountered during use of an IV system, such as when the fluid flow is stopped for a period of time or flows at a too slow rate. For example, thrombi in, on and/or around the catheter 12, such as at the catheter's orifice 12b can cause an occlusion. Occlusion of the catheter can require insertion of a new catheter in another location. It is known that a slow flow of IV solution (e.g., saline or calibration fluid, with or without heparin) can prevent catheter occlusion due to thrombosis. This procedure is know as keep vein open (KVO). Accordingly, the flow profile can be configured to prevent catheter occlusion, such as by inclusion of a KVO phase in the flow profile, wherein the fluid flow rate is reduced (but not completely stopped) relative to the calibration and/or flush flow rates. In preferred embodiments, the KVO flow rate is sufficient to prevent the catheter 12 from clotting off and is relatively lower than the flow rate used to flush (above). In preferred embodiments, the KVO flow rate is sufficient to overcome the host vessel pressure (e.g., venous pressure, arterial pressure) and is relatively lower than the flow rate used to flush (above). In some embodiments, the KVO flow rate is from about 0.01, 0.02, 0.05, 0.1, 0.5, 1, 2, 3, 4, 5, 10, 20, 30, 40, 50, 60.0, 70, 80, or 90-µl/min or less to about 0.02, 0.05, 0.1, 0.15, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0-ml/min or more. In some embodiments, the KVO flow rate is less than about 60%, 50%, 40%, 30%, 20%, or 10% of the calibration and/or flush flow rate(s). In some embodiments, the KVO step is performed for from about 0.25, 0.5, 0.75, 1, 2, 3, 4, 5, 6, 7, 8, or 9 minutes or less to about 10, 15, 20, 30, 45 or 60 minutes or more. In preferred embodiments, the solution 132a flows at a rate such that the temperature of the solution substantially equilibrates with the temperature of the tissue surrounding the in vivo portion of the catheter 12. Advantageously, equilibrating the solution temperature with that of the surrounding tissue reduces the effect of temperature on sensor 14 calibration and/or sample measurement, thereby improving sensor accuracy and consistency. In some embodiments, the KVO step can be incorporated into one or more of the flow profile phases described herein, including measurement and flush phases, above.

In some embodiments, the analyte sensor is implanted in the host (e.g., via a vascular access device) for an extended period of time. For example, in some embodiments, a sensor session can last 3, 5, 7, 10, 21, or 30 or more days. As used herein, the term "sensor session" is a broad term and refers without limitation to the period of time of sensor is applied to (e.g., implanted in) the host and is being used to obtain sensor values. For example, in some embodiments, a sensor session extends from the time of sensor (e.g., including implanting the vascular access device) implantation to when the sensor is removed. During this period of time, the vein's condition can deteriorate, such that vein and/or vascular access device is no longer patent (e.g., freely open, not occluded), and the system can no longer function optimally. While not wishing to be bound by theory, it is believed that patency can be substantially maintained during a sensor session by metering a reference/calibration solution through the vascular access device a sufficient amount of time (e.g., a percentage of the duration of the sensor session). As used herein, the phrase "a sufficient amount" is a broad term and refers without limitation to an amount that provides a desired function. For example, a sufficient amount can be a sufficient amount of time, a sufficient amount of fluid volume, and the like. In some embodiments, a sufficient amount can be expressed numerically, such as a percent (%), a volume, a weight, a period of time (e.g., minutes, hours, days, months), and the like. For example, in some embodiments, the flow profile (e.g., within the processor module) is configured such that the flow control device meters a sufficient amount of a reference solution (e.g., through the vascular access device) such that the analyte sensor contacts the reference solution at least about 50%, 55%, 60%, 65%, 70%, 75%, 80%, 85%, 90% or 95% of the time during a sensor session. In other embodiments, the flow profile is configured such that the analyte sensor contacts the reference solution from about 10%, 20%, 30%, or 40% of the time during a sensor session In some embodiments, the sensor is located in or on the vascular access device and the flow profile (e.g., the processor module) is configured such that the flow control device meters the reference solution through the vascular access device for a sufficient amount of time (e.g., a portion of the sensor session), with a sufficient flow rate (e.g., from about 0.01, 0.03, 0.05, 0.07, 0.09 ml/min to about 0.1, 0.2, 0.3, 0.4, 0.5, 0.6, 0.7, 0.8, 0.9 or 1.0 ml/min or more) that the vascular access device remains patent during a sensor session. Advantageously, the flow rate is sufficient to maintain a patent vessel without infusing excess fluid. In a preferred embodiment, the vascular access device remains patent during a sensor session of at least about 1, 3, 5, 7, 10, 15, 20, 25, or 30 days, or longer.

Hospitalized patients, particularly those in the ICU, are frequently given one or more medicaments by IV infusion. For example, the host may receive one or more of beta blockers, anticoagulants, dopamines, alteplase, anistreptases, benztropine, calcium, dalteparin, diltiazem, diphenhydramine, dopexamine, enoxaparin, ephedrine, heparin, insulin, ketorolac, magnesium sulfate, metoprolol, milrinone, nalmefene, naloxone, nicardipine, nimodipine, phenyloin, physostigmine, rocuronium, sodium thiosulphate, streptokinase, urokinase, vasopressin, and verapamil via IV infusion. In some circumstances, the infusion solution for use with the present system may contain one or more medicaments. Accordingly, in some embodiments the processor module configured to control the flow profile of a flow control device, wherein the flow profile is configured to intermittently control flow of a fluid through the vascular access device into the circulatory system of the host, wherein the infusion solution comprises a medicament. In some embodiments, the flow profile is configured to intermittently control flow of the medicament through the vascular access device into the circulatory system of the host. In some embodiments, the processor module is configured to meter infusion of the medicament, responsive to one or more criteria. In a further embodiment, the processor module is configured to reprogram the flow profile, responsive to one or more criteria/protocols and/or input from a caretaker.

In one exemplary embodiment, the system is configured and arranged for use of a single bag of infusion fluid, which can be purchased with the desired medicament concentration, or the medicament can be added to the infusion fluid, such as a saline or calibration fluid, at the bedside. For example, in one embodiment, the sensor is a glucose sensor and the infusion solution contains 100-mg/dl glucose. The nurse mixes in insulin, at the bedside, to obtain the desired final insulin concentration. In this exemplary embodiment, the processor module can be configured to adaptively adjust, modify and/or program at least a portion of the flow profile to deliver an amount of the insulin-containing glucose solution to modify the host's blood glucose level, such as according to pre-programmed thresholds and/or protocols.

In another exemplary embodiment, the system is configured and arranged for use of two bags of IV solution, such as but not limited to a saline solution (e.g., for washing) and a calibration solution, or such as a calibration solution and a medicament solution. In some embodiments, the solutions can be mixed by the flow control device, such as by a mixing valve, or they can be infused separately, such as into separate lumens of a dual lumen catheter or by stopping the flow of one solution while infusing an amount of the other solution (and vice versa). In some embodiments, the system is configured to piggyback a medicament infusion pump, such as but not limited to a syringe pump, a peristaltic pump, and a personal, ambulatory medicament pump, such as an insulin pump. In some embodiments, the processor module is configured and arranged to direct infusion of the medicament via the flow profile, such as through the output module. In some embodiments, the processor module is configured to adaptively adjust, modify and/or reprogram the flow profile, responsive to analyte levels and/or medicament infusion needs, as described elsewhere herein.

FIG. 6 is a graph illustrating a portion of an exemplary flow profile, in one embodiment. The arrow at the bottom of the graph illustrates the passage of time, as the flow profile passes from one phase to the next. The first phase illustrated, in this particular flow profile, is an infusion phase, a period of time for infusion fluid. In some embodiments, the infusion phase can be a wash phase, wherein a sufficient amount of solution is infused at a rate sufficient to wash the sensor/catheter and/or fluid coupler. For example, the Rate 1 could be about 0.25 ml/hr, 0.5 ml/hr, 0.75 ml/hr, 1.0 ml/hr, 1.5 ml/hr, 2.0 ml/hr, 2.5 ml/hr, 3.0 ml/hr, 3.5 ml/hr, 4.0 ml/hr, 4.5 ml/hr, 5.0 ml/hr, or more. At the end of the infusion phase, the flow profile causes the flow control device to slow the flow to Rate 2 (e.g., 0.0 ml/hr, 0.25 ml/her, 0.5 ml/hr, 0.75 ml/hr, 1.0 ml/hr, 1.5 ml/hr, or more); during this period the sensor is contacted with the solution (which may or may not contain the analyte) and calibration measurements are taken. At the end of the calibration phase, the flow profile causes the flow control device to draw back a sample of blood at Rate 3, such that the analyte sensor is contacted with the sample. Suitable drawback rates are described elsewhere herein. In preferred embodiments, a sufficient amount of sample is drawn back such that the sensor is bathed in undiluted blood (e.g., not diluted with calibration solution that was in the catheter). In this exemplary embodiment, when the draw-back phase is complete, the flow profile again directs the flow control device to return to Rate 2. In this flow profile, the measurement phase, when analyte measurements are taken, occur when the flow rate is Rate 2. When the measurement phase is complete, this flow profile includes a wash phase, which includes Rate 4, which can be greater than Rates 1-3. In this embodiment, the wash phase pushes (e.g., flushes) the collected sample out of the catheter. In some embodiments, the amount and/or rate of fluid infusion is sufficient to return the sample to the host and to sufficiently wash the sensor/fluid coupler and/or catheter that the next sample collected is substantially undiluted (e.g., uncontaminated) by the pervious sample. At the completion of the wash phase, the flow profile can be configured to return to the infusion phase, and pass through all of the illustrated phases in a cyclical manner, for at least a period of time. The flow profile can also be configured with additional phases, such as phases configured for infusion of one or more solutions, such as medicaments. The flow profile can be configured with fewer phases, in some embodiments. In preferred embodiments, the processor module is configured to adaptively modify the flow profile, such as the phases included, the flow rates of a give phase, and the like, responsive to measured analyte levels, input protocols, information received from the caretaker or another medical device, information from the flow control device, and the like.

Processing Sensor Data

In addition to controlling fluid infusion and draw back, the processor module (e.g., of the system electronics 110) includes systems and methods for receiving and processing sensor data associated with the preferred embodiments and related sensor technologies include at least three steps: initialization, calibration, and measurement. Accordingly, the system electronics are configured to process the signal to obtain one or more sensor analyte values. In some embodiments, the flow profile is determined based at least in part on one or more sensor analyte values. Although some exemplary analyte sensors are described in detail herein, the systems and methods for processing sensor data can be implemented with a variety of analyte sensors utilizing a variety of measurement technologies including enzymatic, chemical, physical, electrochemical, spectrophotometric, polarimetric, calorimetric, radiometric, and the like. Namely, analyte sensors using any known method, including invasive, minimally invasive, and non-invasive sensing techniques, configured to produce a data signal indicative of an analyte concentration in a host during exposure of the sensor to a biological sample, can be substituted for the exemplary analyte sensor described herein.

In some embodiments, the analyte sensor 14 is initialized, wherein initialization includes application of the sensor and/or sensor system in or on the host. In some embodiments, the processor module includes a computer system including programming configured for performing one or more of the following functions: turning the system on, requesting and/or receiving initial data (e.g., time, location, codes, etc), requesting and/or receiving patient data (e.g., age, conditions, medications, insulin dosing, etc), requesting and/or receiving calibration information (e.g., manufacturer calibration lot data, reference information such as solution(s) provided for calibration, etc.), and the like.

In some embodiments, the sensor system is configured with a predetermined initial break-in time. In some embodiments, the sensor's sensitivity (e.g., sensor signal strength with respect to analyte concentration) and/or baseline can be used to determine the stability of the sensor; for example, amplitude and/or variability of sensor sensitivity and/or baseline may be evaluated to determine the stability of the sensor signal. In alternative embodiments, detection of pH levels, oxygen, hypochlorite, interfering species (e.g., ascorbate, urea, and acetaminophen), correlation between sensor and reference values (e.g., R-value), and the like may be used to determine the stability of the sensor. In some embodiments, the sensor is configured to calibrate during sensor break-in, thereby enabling measurement of the biological sample prior to completion of sensor break-in.

In one embodiment, systems and methods are configured to process calibrated sensor data during sensor break-in. In general, signals associated with a calibration and/or measurement phase of the sensor system can be measured during initial sensor break-in. Using a rate method for measuring an analyte (e.g., measuring the rate of change of a step change), a sensor signal can be calibrated with a correction factor to account for the rate of change of the break-in curve. In one exemplary embodiment, the bottom of sequential step responses (e.g., of calibration phases during sensor break-in) can be fit to a line or curve (e.g., using linear or non-linear regression, such as least squares regression), to extrapolate the rate of change of the curve of the sensor break-in. Accordingly, the rate of change measured in a measurement phase can be corrected to account for the rate of change of the sensor break-in curve, and the sensor signal calibrated. By calibrating during sensor break-in, sensor data can more quickly be provided (e.g., to the user interface) after sensor insertion.

In some embodiments, systems and methods are configured to determine an initial baseline value of the sensor. In general, baseline refers to a component of an analyte sensor signal that is not substantially related to the analyte concentration In one example of a glucose sensor, the baseline is composed substantially of signal contribution due to factors other than glucose (for example, interfering species, non-reaction-related hydrogen peroxide, or other electroactive species with an oxidation/reduction potential that overlaps with hydrogen peroxide).

In preferred embodiments, the sensor system includes a computer system including programming configured to determine calibration information and calibrate a signal associated with a biological sample there from. In general, calibration of the signal includes initial calibration, update calibration and/or re-calibration of the sensor signal. Detailed description of sensor calibration and break-in can be found in U.S. Pat. No. 7,276,029, U.S. Pat. No. 7,366,556, U.S. Patent Publication No. US-2005-0187720-A1, U.S. Patent Publication No. US-2008-0183061-A1, U.S. Patent Publication No. US-2005-0027463-A1, U.S. Patent Publication No. US-2008-0183399-A1, U.S. Patent Publication No. US-2005-0021666-A1, U.S. Patent Publication No. US-2005-0043598-A1, U.S. Patent Publication No. US-2007-0032706-A1, U.S. Patent Publication No. US-2007-0016381-A1, U.S. Patent Publication No. US-2008-0033254-A1, U.S. Patent Publication No. US-2005-0203360-A1, U.S. Patent Publication No. US-2005-0143635-A1, U.S. Patent Publication No. US-2007-0213611-A1, U.S. Patent Publication No. US-2008-0083617-A1, U.S. Patent Publication No. US-2007-0027284-A1, U.S. Patent Publication No. US-2006-0258929-A1, U.S. Patent Publication No. US-2008-0119703-A1, U.S. Patent Publication No. US-2008-0108942-A1, and co-pending U.S. patent application Ser. No. 12/055,114 filed Mar. 25, 2008 and entitled "ANALYTE SENSOR," all of which are incorporated herein by reference in their entirety.

In some embodiments, the sensor system includes one or more reference solutions (e.g., calibration solutions in some embodiments), wherein the system is configured to expose the sensor to the one or more reference solution(s) to provide calibration information (e.g., an internal reference value), such as baseline and/or sensitivity information for the sensor. In one exemplary embodiment, a reference solution including a known analyte concentration is provided, wherein the system is configured to expose the sensor to the reference solution, and wherein the system is configured to produce a data signal indicative of an analyte concentration in the reference solution during exposure of the sensor to the reference solution, as described in more detail elsewhere herein. In some embodiments, two reference solutions with two different analyte concentrations are provided. For example, in order to generate reference values for detecting sensitivity drift of a glucose sensor, two saline solutions containing 100 and 200 mg/dl glucose respectively can be provided.

In general the system can be configured to obtain internal reference values at one or more time points, intermittently, and/or continuously. For example, in some embodiments, calibration for drift in baseline and/or sensitivity can be done at set time intervals, depending upon the severity of the drift. In some circumstances, it is preferred to calibrate very frequently (e.g., between about every 1 minute or less and about every 2, 3, 4, 5, 10, 15, 20 or 30 minutes or longer). In other circumstances, it is preferred to calibrate less frequently (e.g., about every 1, 2, 3, 5, 10 15 or 24 hours or longer). For example, in some circumstances, baseline drift has a substantial effect on sensor accuracy, while sensitivity drift has little effect. For example, if the sensor is a glucose sensor, host consumption of acetaminophen can increase the baseline, while sensor sensitivity is relatively unaffected. On the other hand, in some circumstances, sensor sensitivity drift has a substantial effect on sensor accuracy, while baseline has little effect. For example, prior to completion of sensor break-in, sensor sensitivity can increase dramatically, while baseline may fluctuate very little. Accordingly, a baseline calibration solution (e.g., 0-mg/dl glucose) can be used to calibrate the baseline about every 5 minutes. Thus, to calibrate for sensitivity drift, an analyte-containing calibration solution (e.g., 100-mg/dl glucose in saline) can be used to calibrate the sensor less frequently, such as about once every 1, 2, 3, 5, 10, 12, 24, 48 or more hours. In some embodiments, one or more external reference values, such as reference values obtained by testing a blood sample with SMBG or a YSI device, can be used to calibrate the system, in addition to the internally provided reference values (e.g., provided via the calibration solutions).

Although much of the description focuses on the use of a reference calibration solution to provide an internal reference value, other sensor technologies, such as optical sensing methods, are known to provide one or more internal reference standards (e.g., of known absorbance, reflectance, fluorescence, etc) to determine baseline and/or sensitivity information, as is appreciated by one skilled in the art; accordingly, the systems and methods described herein can be implemented with other types of internal reference values. In some embodiments, a "plateau" is reached when the sensor has been exposed to the sample of bodily fluid (e.g., blood) or a reference solution a sufficiently long period of time that the sensor's enzyme has used up (e.g., reacted with, detected) substantially all of the available analyte.

In some embodiments, once at least a portion of the calibration information is determined, the sensor system is configured to expose the sensor to a biological sample and measure a signal response thereto. In some embodiments, the sensor can be continuously exposed to the biological sample, wherein at least some external (e.g., in vitro test) reference values are used as calibration information for calibrating the sensor system. For example, in some embodiments, an in vitro reference value can be obtained using a hand-held testing device (e.g., an ambulatory glucose meter) or by sending a blood sample to a clinical lab for testing (e.g., a YSI device). In some embodiments, the sensor can be intermittently exposed to the biological sample, wherein at least some internal reference values are used as calibration information for calibrating the sensor system, also referred to as auto-calibration in some exemplary embodiments.

In one preferred embodiment, a system is provided for monitoring analyte concentration in a biological sample of a host, the system including: a substantially continuous analyte sensor configured to produce a data signal indicative of an analyte concentration in a host during exposure of the sensor to a biological sample; a reference solution including a known analyte concentration, wherein the system is configured to expose the sensor to the reference solution, and wherein the sensor is configured to produce a data signal indicative of an analyte concentration in the reference solution during exposure of the sensor to the reference solution; and a computer system including programming configured to determine calibration information and calibrate a signal associated with a biological sample there from, wherein the calibration information includes steady state information and transient information. In some embodiments, the calibration information is determined from a signal associated with exposure of the sensor to the reference solution and a signal associated with exposure of the sensor to a biological sample. In a further embodiment, the biological sample is of unknown or uncalibrated analyte concentration.

Diagnostics and Fail-Safes

In some embodiments, the processor module comprises a fail-safe module. In some embodiments, a fail-safe module comprises programming configured to modify system function responsive to a pre-programmed criterion, such as a maximum and/or minimum allowed sample drawback, maximum and/or minimum amounts of fluid infusion, maximum and/or minimum allowable analyte levels, and the like. For example, if a flow control device were allowed to run in the reverse direction for too long, the host could be exsanguinated. Accordingly, in preferred embodiments, the fail-safe module can include a fail safe specifying a maximum allowed sample drawback. In a further embodiment, the fail-safe module can be configured to turn off the flow control device (or set the flow rate to 0 ml/min for an extended period of time and/or until the system is restarted by a caretaker), if the criterion of maximum allowed drawback is exceeded. In a further example, the fail safe can engage an audio alarm, such as an alarm included in the system electronics and/or an alarm included in the flow control device, to notify a caretaker of a system malfunction.

In some embodiments, the system includes programming configured to diagnose a condition of at least one of the sensor and the host responsive to calibration information. In some embodiments, the system intermittently or continuously determines at least some calibration information (e.g., sensitivity information, $b_{offset}$, and the like) each time the sensor is exposed to a reference solution and/or a biological sample.

In one embodiment, systems and methods are configured to find a plateau and/or stable window of data in response to exposure of the sensor to at least one of a reference solution and a biological sample. In some embodiments, if the system cannot find the plateau and/or stable window of data, the system is configured to "fail-safe," for example, in some circumstances, a lack of plateau and/or stable window of data may be indicative of dilution and/or mixture of the reference solution (e.g., calibration solution) with the biological sample (e.g., blood), and/or interruption/disruption of expected/desired fluid flow. Additionally, in some circumstances, a lack of plateau and/or stable window of data may be indicative of interfering species in the signal.

In general, the term "fail-safe" includes modifying the system processing and/or display of data in some manner responsive to a detected error, or unexpected condition, and thereby avoids reporting and/or processing of potentially inaccurate or clinically irrelevant analyte values.

In another embodiment, systems and methods are configured to process a signal responsive to exposure of the signal to a reference and/or biological sample to determine whether the signal is within a predetermined range; if the signal falls outside the range, the system is configured to fail-safe.

In preferred embodiments, the sensor electronics include a fail-safe module that is configured to detect a system malfunction. The fail-safe module can be configured to detect a variety of system malfunctions. For example, the fail-safe module can be configured to detect electrical malfunctions, malfunctions of the system fluidics, malfunctions of the sensor, and/or the like. For example, the system electronics can be configured to test and/or track the functions of different system components, and to intelligently recognize aberrant changed in such functions as possible malfunctions.

In some embodiments, the fail-safe module is configured to detect electrical malfunctions, such as but not limited to short circuit and electrical malfunction associated with start-up and/or sensor break-in. In some embodiments, the fail-safe module is configured to detect fluidics malfunctions, which can include a malfunction of any part of the system configured to contact and/or move a fluid. For example, the vascular access device (catheter) can become occluded, such as due to blood clotting or pressing the in vivo orifice (e.g., catheter tip) against a vessel wall such that fluid cannot move in an out of the vascular access device. In some circumstances, the tubing can become kinked, the host can move his arm such that the catheter becomes bent, bubbles may get into the system, and/or the flow control system can malfunction (e.g., not metering fluid flow into the host or not withdrawing blood samples as it was programmed to do), such that washing, calibration, sample collection and the like are not performed as programmed. For example, the sample can become diluted with calibration solution, there may be clotting on a portion of the sensor, and the like. In one exemplary embodiment, the fail-safe module is configured detect fluidics malfunctions by monitoring the pattern of signal increases/decreases generated on the working electrode(s), to detect periods of time during which the signal does not follow an expected waveform (e.g., using known waveform analysis methods and/or pattern recognition algorithms), such as when the signal hits upper and/or lower limits. For example, if the signal zeros for a period of time, the fluidics system may be unable to withdraw a blood sample due to kinking of the tubing or occlusion of the catheter. In another example, the signal on the working electrode(s) may stop going back down when the tested blood sample should be re-infused into the host and the sensor should be contacted with wash/reference solution, which is indicative of a malfunction of expelling the used sample, washing the sensor, and the like. For example, if the catheter becomes occluded by a blood clot, the flow control system will be unable to meter fluid through the catheter.

In some embodiments, the fail-safe module is also configured to detect malfunctions of the analyte sensor. For example, a sensor malfunction includes but is not limited to noise on the signal, drift of sensor sensitivity and/or baseline, a broken component of the sensor, blood clotting on a portion of the sensor, and cross-talk, as described in more detail elsewhere herein.

Methods and devices that are suitable for use in conjunction with aspects of the preferred embodiments are disclosed in U.S. Pat. No. 4,994,167; U.S. Pat. No. 4,757,022; U.S. Pat. No. 6,001,067; U.S. Pat. No. 6,741,877; U.S. Pat. No. 6,702,857; U.S. Pat. No. 6,558,321; U.S. Pat. No. 6,931,327; U.S. Pat. No. 6,862,465; U.S. Pat. No. 7,074,307; U.S. Pat. No. 7,081,195; U.S. Pat. No. 7,108,778; U.S. Pat. No. 7,110,803; U.S. Pat. No. 7,192,450; U.S. Pat. No. 7,226,978; U.S. Pat. No. 7,310,544; U.S. Pat. No. 7,364,592; U.S. Pat. No. 7,366,556; and U.S. Pat. No. 7,424,318.

Methods and devices that are suitable for use in conjunction with aspects of the preferred embodiments are disclosed in U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No. US-2005-0154271-A1; U.S. Patent Publication No. US-2004-0199059-A1; U.S. Patent Publication No. US-2005-0054909-A1; U.S. Patent Publication No. US-2005-0051427-A1; U.S. Patent Publication No. US-2003-0032874-A1; U.S. Patent Publication No. US-2005-0103625-A1; U.S. Patent Publication No. US-2005-0203360-A1; U.S. Patent Publication No. US-2005-0090607-A1; U.S. Patent Publication No. US-2005-0187720-A1; U.S. Patent Publication No. US-2005-0161346-A1; U.S. Patent Publication No. US-2006-0015020-A1; U.S. Patent Publication No. US-2005-0043598-A1; U.S. Patent Publication No. US-2005-0033132-A1; U.S. Patent Publication No. US-2005-0031689-A1; U.S. Patent Publication No. US-2004-0186362-A1; U.S. Patent Publication No. US-2005-0027463-A1; U.S. Patent Publication No. US-2005-0027181-A1; U.S. Patent Publication No. US-2005-0027180-A1; U.S. Patent Publication No. US-2006-0020187-A1; U.S. Patent Publication No. US-2006-0036142-A1; U.S. Patent Publication No. US-2006-0020192-A1; U.S. Patent Publication No. US-2006-0036143-A1; U.S. Patent Publication No. US-2006-0036140-A1; U.S. Patent Publication No. US-2006-0019327-A1; U.S. Patent Publication No. US-2006-0020186-A1; U.S. Patent Publication No. US-2006-0036139-A1; U.S. Patent Publication No. US-2006-0020191-A1; U.S. Patent Publication No. US-2006-0020188-A1; U.S. Patent Publication No. US-2006-0036141-A1; U.S. Patent Publication No. US-2006-0020190-A1; U.S. Patent Publication No. US-2006-0036145-A1; U.S. Patent Publication No. US-2006-0036144-A1; U.S. Patent Publication No. US-2006-0016700-A1; U.S. Patent Publication No. US-2006-0142651-A1; U.S. Patent Publication No. US-2006-0086624-A1; U.S. Patent Publication No. US-2006-0068208-A1; U.S. Patent Publication No. US-2006-0040402-A1; U.S. Patent Publication No. US-2006-0036142-A1; U.S. Patent Publication No. US-2006-0036141-A1; U.S. Patent Publication No. US-2006-0036143-A1; U.S. Patent Publication No. US-2006-0036140-A1; U.S. Patent Publication No. US-2006-0036139-A1; U.S. Patent Publication No. US-2006-0142651-A1; U.S. Patent Publication No. US-2006-0036145-A1; U.S. Patent Publication No. US-2006-0036144-A1; U.S. Patent Publication No. US-2006-0200022-A1; U.S. Patent Publication No. US-2006-0198864-A1; U.S. Patent Publication No. US-2006-0200019-A1; U.S. Patent Publication No. US-2006-0189856-A1; U.S. Patent Publication No. US-2006-0200020-A1; U.S. Patent Publication No. US-2006-0200970-A1; U.S. Patent Publication No. US-2006-0183984-A1; U.S. Patent Publication No. US-2006-0183985-A1; U.S. Patent Publication No. US-2006-0195029-A1; U.S. Patent Publication No. US-2006-0229512-A1; U.S. Patent Publication No. US-2006-0222566-A1; U.S. Patent Publication No. US-2007-0032706-A1; U.S. Patent Publication No. US-2007-0016381-A1; U.S. Patent Publication No. US-2007-0027370-A1; U.S. Patent Publication No. US-2007-0027384-A1; U.S. Patent Publication No. US-2007-0032718-A1; U.S. Patent Publication No. US-2007-0059196-A1; U.S. Patent Publication No. US-2007-0066873-A1; U.S. Patent Publication No. US-2007-0197890-A1; U.S. Patent Publication No. US-2007-0173710-A1; U.S. Patent Publication No. US-2007-0163880-A1; U.S. Patent Publication No. US-2007-0203966-A1; U.S. Patent Publication No. US-2007-0213611-A1; U.S. Patent Publication No. US-2007-0232879-A1; U.S. Patent Publication No. US-2007-0235331-A1; U.S. Patent Publication No. US-2008-0021666-A1; U.S. Patent Publication No. US-2008-0033254-A1; U.S. Patent Publication No. US-2008-0045824-A1; U.S. Patent Publication No. US-2008-0071156-A1; U.S. Patent Publication No. US-2008-0086042-A1; U.S. Patent Publication No. US-2008-0086044-A1; U.S. Patent Publication No. US-2008-0086273-A1; U.S. Patent Publication No. US-2008-0083617-A1; U.S. Patent Publication No. US-2008-0119703-A1; U.S. Patent Publication No. US-2008-0119704-A1; U.S. Patent Publication No. US-2008-0119706-A1 U.S. Patent Publication No. US-2008-0194936-A1; U.S. Patent Publication No. US-2008-0194937-A1; U.S. Patent Publication No. US-2008-0195967-A1; U.S. Patent Publication No. US-2008-0183061-A1; U.S. Patent Publication No. US-2008-0183399-A1; U.S. Patent Publication No. US-2008-0189051-A1; U.S. Patent Publication No. US-2008-0214918-A1; U.S. Patent Publication No. US-2008-0194938-A1; U.S. Patent Publication No. US-2008-0214915-A1; U.S. Patent Publication No. US-2008-0194935-A1; U.S. Patent Publication No. US-2008-

0188731-A1; U.S. Patent Publication No. US-2008-0242961-A1; U.S. Patent Publication No. US-2008-0208025-A1; U.S. Patent Publication No. US-2008-0197024-A1; U.S. Patent Publication No. US-2008-0200788-A1; U.S. Patent Publication No. US-2008-0200789-A1; U.S. Patent Publication No. US-2008-0200791-A1; U.S. Patent Publication No. US-2008-0228054-A1; U.S. Patent Publication No. US-2008-0228051-A1; and U.S. Patent Publication No. US-2008-0262469-A1.

Methods and devices that are suitable for use in conjunction with aspects of the preferred embodiments are disclosed in U.S. patent application Ser. No. 09/447,227 filed Nov. 22, 1999 and entitled "DEVICE AND METHOD FOR DETERMINING ANALYTE LEVELS"; U.S. patent application Ser. No. 11/654,135 filed Jan. 17, 2007 and entitled "POROUS MEMBRANES FOR USE WITH IMPLANTABLE DEVICES"; U.S. patent application Ser. No. 11/654,140 filed Jan. 17, 2007 and entitled "MEMBRANES FOR AN ANALYTE SENSOR"; U.S. patent application Ser. No. 11/691,426 filed Mar. 26, 2007 and entitled "ANALYTE SENSOR"; U.S. patent application Ser. No. 12/103,594 filed Apr. 15, 2008 and entitled "BIOINTERFACE WITH MACRO- AND MICRO-ARCHITECTURE"; U.S. patent application Ser. No. 12/113,724 filed May 1, 2008 and entitled "LOW OXYGEN IN VIVO ANALYTE SENSOR"; U.S. patent application Ser. No. 12/055,098 filed Mar. 25, 2008 and entitled "ANALYTE SENSOR"; U.S. patent application Ser. No. 12/054,953 filed Mar. 25, 2008 and entitled "ANALYTE SENSOR"; U.S. patent application Ser. No. 12/055,114 filed Mar. 25, 2008 and entitled "ANALYTE SENSOR"; U.S. patent application Ser. No. 12/133,789 filed Jun. 5, 2008 and entitled "INTEGRATED MEDICAMENT DELIVERY DEVICE FOR USE WITH CONTINUOUS ANALYTE SENSOR"; U.S. patent application Ser. No. 12/133,761 filed Jun. 5, 2008 and entitled "INTEGRATED MEDICAMENT DELIVERY DEVICE FOR USE WITH CONTINUOUS ANALYTE SENSOR"; U.S. patent application Ser. No. 12/133,738 filed Jun. 5, 2008 and entitled "INTEGRATED MEDICAMENT DELIVERY DEVICE FOR USE WITH CONTINUOUS ANALYTE SENSOR"; U.S. patent application Ser. No. 12/139,305 filed Jun. 13, 2008 and entitled "ELECTRODE SYSTEMS FOR ELECTROCHEMICAL SENSORS"; U.S. patent application Ser. No. 12/175,391 filed Jul. 17, 2008 and entitled "TRANSCUTANEOUS ANALYTE SENSOR"; U.S. patent application Ser. No. 12/182,008 filed Jul. 29, 2008 and entitled "INTEGRATED RECEIVER FOR CONTINUOUS ANALYTE SENSOR"; U.S. patent application Ser. No. 12/182,073 filed Jul. 29, 2008 and entitled "INTEGRATED RECEIVER FOR CONTINUOUS ANALYTE SENSOR"; U.S. patent application Ser. No. 12/182,083 filed Jul. 29, 2008 and entitled "INTEGRATED RECEIVER FOR CONTINUOUS ANALYTE SENSOR"; U.S. patent application Ser. No. 12/195,191 filed Aug. 20, 2008 and entitled "SYSTEM AND METHODS FOR PROCESSING ANALYTE SENSOR DATA"; U.S. patent application Ser. No. 12/195,773 filed Aug. 21, 2008 and entitled "SYSTEM AND METHODS FOR PROCESSING ANALYTE SENSOR DATA"; U.S. patent application Ser. No. 12/247,137 filed Oct. 7, 2008 and entitled "IMPLANTABLE ANALYTE SENSOR"; U.S. patent application Ser. No. 12/250,918 filed Oct. 14, 2008 and entitled "ANALYTE SENSOR"; U.S. patent application Ser. No. 12/253,125 filed Oct. 16, 2008 and entitled "SIGNAL PROCESSING FOR CONTINUOUS ANALYTE SENSOR"; U.S. patent application Ser. No. 12/253,120 filed Oct. 16, 2008 and entitled "SIGNAL PROCESSING FOR CONTINUOUS ANALYTE SENSOR"; U.S. patent application Ser. No. 12/253,064 filed Oct. 16, 2008 and entitled "SIGNAL PROCESSING FOR CONTINUOUS ANALYTE SENSOR"; U.S. patent application Ser. No. 12/252,996 filed Oct. 16, 2008 and entitled "SIGNAL PROCESSING FOR CONTINUOUS ANALYTE SENSOR"; U.S. patent application Ser. No. 12/252,967 filed Oct. 16, 2008 and entitled "SIGNAL PROCESSING FOR CONTINUOUS ANALYTE SENSOR"; U.S. patent application Ser. No. 12/252,952 filed Oct. 16, 2008 and entitled "SIGNAL PROCESSING FOR CONTINUOUS ANALYTE SENSOR"; U.S. patent application Ser. No. 12/260,017 filed Oct. 28, 2008 and entitled "SENSOR HEAD FOR USE WITH IMPLANTABLE DEVICES"; U.S. patent application Ser. No. 12/258,320 filed Oct. 24, 2008 and entitled "SYSTEMS AND METHODS FOR PROCESSING SENSOR DATA"; U.S. patent application Ser. No. 12/263,993 filed Nov. 3, 2008 and entitled "SIGNAL PROCESSING FOR CONTINUOUS ANALYTE SENSOR"; U.S. patent application Ser. No. 12/264,835 filed Nov. 4, 2008 and entitled "IMPLANTABLE ANALYTE SENSOR"; U.S. patent application Ser. No. 12/258,235 filed Oct. 24, 2008 and entitled "SYSTEMS AND METHODS FOR PROCESSING SENSOR DATA"; U.S. patent application Ser. No. 12/258,345 filed Oct. 24, 2008 and entitled "SYSTEMS AND METHODS FOR PROCESSING SENSOR DATA"; U.S. patent application Ser. No. 12/258,325 filed Oct. 24, 2008 and entitled "SYSTEMS AND METHODS FOR PROCESSING SENSOR DATA"; U.S. patent application Ser. No. 12/258,318 filed Oct. 24, 2008 and entitled "SYSTEMS AND METHODS FOR PROCESSING SENSOR DATA"; U.S. patent application Ser. No. 12/258,335 filed Oct. 24, 2008 and entitled "SYSTEMS AND METHODS FOR PROCESSING SENSOR DATA"; U.S. patent application Ser. No. 12/264,160 filed Nov. 3, 2008 and entitled "DUAL ELECTRODE SYSTEM FOR A CONTINUOUS ANALYTE SENSOR."

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A system for analyte detection in and fluid infusion into a host, comprising:
   an analyte sensor configured and arranged to generate sensor data associated with an analyte;
   a fluid coupler configured to connect an IV equipment with a vascular access device configured for fluid communication with a circulatory system of the host; and
   system electronics operably connected to the analyte sensor and configured to process the sensor data, wherein the system electronics comprise:
      a processor module configured to control a flow profile of a flow control device, wherein the flow profile is configured to intermittently control flow of a fluid through the vascular access device into the circulatory system of the host and to intermittently control a flow of a sample from the circulatory system of the host into the vascular access device when the vascular access device is in fluid communication with the circulatory system of the host and operably connected to the flow control device;
      a data storage memory configured to store the sensor data associated with the analyte of the host; and
      an output module configured and arranged to operably connect with the flow control device so as to enable the processor module to control the flow profile of the flow control device and
   a cable configured to provide a wired connection between the system electronics and the analyte sensor, wherein the cable comprises the data storage memory wherein the system electronics are configured to be powered at least in part by a flow control device.

2. The system of claim 1, wherein the cable is configured to operably connect with a flow control device.

3. The system of claim 2, wherein at least a portion of the system electronics is physically connected to the cable such that the at least a portion of the system electronics is located within a distance of about 8 feet or less of the analyte sensor.

4. The system of claim 1, wherein the system electronics are located on the electrical cable.

5. The system of claim 4, wherein the system electronics are located within a distance of about 3 feet or less of the analyte sensor.

6. The system of claim 1, wherein the system electronics are non-releasably connected with the analyte sensor.

7. The system of claim 1, wherein the system electronics are releasably connected to the analyte sensor.

8. The system of claim 1, wherein the output module is configured and arranged for wireless communication with a flow control device.

9. The system of claim 1, wherein the processor module comprises a fail-safe module.

10. The system of claim 1, wherein the system electronics are configured to process the sensor data to obtain one or more sensor analyte values, and wherein the flow profile is determined based at least in part on the one or more sensor analyte values.

11. The system of claim 1, further comprising a source of a solution comprising a medicament.

12. The system of claim 11, wherein the flow profile is configured to intermittently control flow of the solution comprising the medicament through the vascular access device into the circulatory system of the host.

13. The system of claim 1, wherein the vascular access device comprises a catheter, wherein the analyte sensor comprises an electrode, and wherein the electrode is located within or on the catheter.

14. The system of claim 1, wherein the fluid coupler comprises a first end configured for fluid communication with a catheter configured for implantation in a host's circulatory system and a second end configured for fluid communication with tubing associated with a flow control device.

15. The system of claim 1, wherein at least a portion of the analyte sensor is located within the vascular access device.

16. The system of claim 1, wherein the analyte sensor is located within a distance of about 40 mm or less of an opening in the vascular access device through which a biological sample from the circulatory system of the host is obtained when the vascular access device is in fluid communication with the circulatory system of the host.

17. The system of claim 1, wherein the analyte sensor is located such that the analyte sensor is bathed in a biological sample from the circulatory system of the host when a volume of about 300 µL or less of the biological sample is drawn back into the vascular access device when the vascular access device is in fluid communication with the circulatory system of the host.

18. The system of claim 1, wherein the analyte sensor is configured to continuously measure glucose in a host.

19. The system of claim 1, wherein the analyte sensor is configured to measure a signal associated with at least one analyte selected from the group consisting of albumin, alkaline phosphatase, alanine transaminase, aspartate aminotransferase, bilirubin, blood urea nitrogen, calcium, $CO_2$ chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker, and a drug.

20. The system of claim 1, further comprising a flow control device configured for fluid communication with the vascular access device and configured to intermittently infuse a fluid and draw back a biological sample of the circulatory system responsive to the flow profile.

21. The system of claim 20, wherein the flow control device comprises a pump.

22. The system of claim 21, wherein the pump comprises a bi-directional pump.

23. The system of claim 21, wherein the pump comprises a peristaltic pump.

24. A system for analyte detection in and fluid infusion into a host, comprising:
   an analyte sensor configured and arranged to generate sensor data associated with an analyte;
   a fluid coupler configured to connect an IV equipment with a vascular access device configured for fluid communication with a circulatory system of the host; and
   system electronics operably connected to the analyte sensor and configured to process the sensor data, wherein the system electronics comprise:
      a processor module configured to control a flow profile of a flow control device, wherein the flow profile is configured to intermittently control flow of a fluid through the vascular access device into the circulatory system of the host and to intermittently control a flow of a sample from the circulatory system of the host into the vascular access device when the vascular access device is in fluid communication with the circulatory system of the host and operably connected to the flow control device;

a data storage memory configured to store the sensor data associated with the analyte of the host; and an output module configured and arranged to operably connect with the flow control device so as to enable the processor module to control the flow profile of the flow control device; and a cable configured to provide a wired connection between the system electronics and the analyte sensor, wherein the cable comprises the data storage memory, wherein the system electronics are actuated upon engagement of the system electronics with a flow control device.

* * * * *

UNITED STATES PATENT AND TRADEMARK OFFICE
CERTIFICATE OF CORRECTION

PATENT NO. : 8,425,417 B2
APPLICATION NO. : 12/267494
DATED : April 23, 2013
INVENTOR(S) : Jacob S. Leach, Peter C. Simpson and Mark Brister It is certified that error appears in the above-identified patent and that said Letters Patent is hereby corrected as shown below:

Title Page, Item (75) Inventors: add the following inventor --Mark Brister, Encinitas, CA (US)--.

Signed and Sealed this
Twenty-fourth Day of September, 2013

Teresa Stanek Rea
*Deputy Director of the United States Patent and Trademark Office*